United States Patent
Shen et al.

(10) Patent No.: US 10,829,486 B2
(45) Date of Patent: *Nov. 10, 2020

(54) ISOXAZOLE DERIVATIVES AS FXR AGONISTS AND METHODS OF USE THEREOF

(71) Applicant: ENANTA PHARMACEUTICALS, INC., Watertown, MA (US)

(72) Inventors: Ruichao Shen, Belmont, MA (US); Jun Ma, Belmont, MA (US); Guoqiang Wang, Belmont, MA (US); Xuechao Xing, Wilmington, MA (US); Yat Sun Or, Waltham, MA (US)

(73) Assignee: Enanta Pharmacueticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/272,506

(22) Filed: Feb. 11, 2019

(65) Prior Publication Data

US 2019/0248777 A1   Aug. 15, 2019

Related U.S. Application Data

(60) Provisional application No. 62/652,579, filed on Apr. 4, 2018, provisional application No. 62/630,574, filed on Feb. 14, 2018.

(51) Int. Cl.
| | | |
|---|---|---|
| C07D 417/04 | (2006.01) | |
| A61P 1/16 | (2006.01) | |
| A61P 3/10 | (2006.01) | |
| A61P 9/10 | (2006.01) | |
| A61P 3/04 | (2006.01) | |
| A61P 13/12 | (2006.01) | |

(52) U.S. Cl.
CPC .............. *C07D 417/04* (2013.01); *A61P 1/16* (2018.01); *A61P 3/04* (2018.01); *A61P 3/10* (2018.01); *A61P 9/10* (2018.01); *A61P 13/12* (2018.01)

(58) Field of Classification Search
CPC .. C07D 261/02; C07D 261/06; C07D 261/08; A61K 31/41; A61K 31/42; A61K 31/422
USPC ........................................... 548/161; 514/367
See application file for complete search history.

(56) References Cited

U.S. PATENT DOCUMENTS

| | | |
|---|---|---|
| 5,571,809 A | 11/1996 | Hargrave et al. |
| 6,974,830 B2 | 12/2005 | Giegrich et al. |
| 7,319,109 B2 | 1/2008 | Boggs et al. |
| 7,846,960 B2 | 12/2010 | Bell et al. |
| 7,863,302 B2 | 1/2011 | Bell et al. |
| 7,897,773 B2 | 3/2011 | Aletru et al. |
| 7,902,373 B2 | 3/2011 | Blake et al. |
| 8,952,042 B2 | 2/2015 | Kremoser et al. |
| 9,751,874 B2 | 9/2017 | Gege et al. |
| 10,450,306 B2 * | 10/2019 | Ma ........................ C07D 413/12 |
| 2004/0048316 A1 | 3/2004 | Haffner et al. |
| 2007/0054902 A1 | 3/2007 | Fukui et al. |
| 2007/0142340 A1 | 6/2007 | Pellicciari et al. |
| 2008/0167356 A1 | 7/2008 | Caldwell et al. |
| 2009/0163474 A1 | 6/2009 | Zhang et al. |
| 2010/0063697 A1 | 3/2010 | Lindgren et al. |
| 2010/0099703 A1 | 4/2010 | Garcia-López et al. |
| 2010/0120775 A1 | 5/2010 | Bass, III et al. |
| 2010/0152166 A1 | 6/2010 | Genin et al. |
| 2010/0184809 A1 | 7/2010 | Kremoser et al. |
| 2010/0210660 A1 | 8/2010 | Kremoser et al. |
| 2010/0249179 A1 | 9/2010 | Deaton et al. |
| 2010/0292212 A1 | 11/2010 | Ackermann et al. |
| 2011/0034507 A1 | 2/2011 | Akwabi-Ameyaw et al. |
| 2011/0275595 A1 | 11/2011 | Eckhardt et al. |
| 2012/0004164 A1 | 1/2012 | Dales et al. |
| 2013/0261108 A1 | 10/2013 | Tully et al. |
| 2014/0038947 A1 | 2/2014 | Glick et al. |
| 2014/0221659 A1 | 8/2014 | Kinzel et al. |

(Continued)

FOREIGN PATENT DOCUMENTS

| | | |
|---|---|---|
| CN | 106588804 A | 4/2017 |
| CN | 106632294 A | 5/2017 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak R Rao
(74) *Attorney, Agent, or Firm* — Edgar W. Harlan; Carolyn S. Elmore; Elmore Patent Law Group, P.C.

(57) ABSTRACT

The present invention provides compounds of Formula (I):

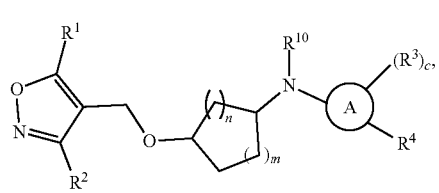

pharmaceutical compositions comprising these compounds and methods of using these compounds to treat or prevent a disease or disorder mediated by FXR. Specifically, the present invention relates to isoxazole derivatives useful as agonists for FXR, and methods for their preparation and use.

21 Claims, No Drawings

(56) References Cited

U.S. PATENT DOCUMENTS

| | | |
|---|---|---|
| 2015/0299210 A1 | 10/2015 | Bailey et al. |
| 2015/0366856 A1 | 12/2015 | Mutnick et al. |
| 2016/0130297 A1 | 5/2016 | Xing et al. |
| 2017/0298068 A1 | 10/2017 | Gege et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355685 A1 | 12/2017 | Blomgren et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2018/0030003 A1 | 2/2018 | Wang et al. |
| 2018/0099957 A1 | 4/2018 | Ma et al. |
| 2018/0141941 A1 | 5/2018 | He et al. |

FOREIGN PATENT DOCUMENTS

| | | |
|---|---|---|
| CN | 106946867 A | 7/2017 |
| CN | 106995416 A | 8/2017 |
| CN | 107021957 A | 8/2017 |
| CN | 108017636 A | 5/2018 |
| CN | 108341822 A | 7/2018 |
| CN | 109053751 A | 12/2018 |
| WO | 2004046162 A2 | 6/2004 |
| WO | 2009149795 A2 | 12/2009 |
| WO | 2011020615 A1 | 2/2011 |
| WO | 2011021645 A1 | 2/2011 |
| WO | 2012087519 A1 | 6/2012 |
| WO | 2012087520 A1 | 6/2012 |
| WO | 2012087521 A1 | 6/2012 |
| WO | 2013007387 A1 | 1/2013 |
| WO | 2013037482 A1 | 3/2013 |
| WO | 2013166176 A1 | 11/2013 |
| WO | 2015036442 A1 | 3/2015 |
| WO | 2017118294 A1 | 7/2017 |
| WO | 2017128896 A1 | 8/2017 |
| WO | 2017145041 A1 | 8/2017 |
| WO | 2017133521 A1 | 10/2017 |
| WO | 2017201150 A1 | 11/2017 |
| WO | 2018024224 A1 | 2/2018 |
| WO | 2018039386 A1 | 3/2018 |
| WO | 2018067704 A1 | 4/2018 |
| WO | 2018075207 A1 | 4/2018 |
| WO | 2018085148 A1 | 5/2018 |
| WO | 2018133730 A1 | 7/2018 |
| WO | 2018170173 A1 | 9/2018 |
| WO | 2018190643 A1 | 10/2018 |
| WO | 2018214959 A1 | 11/2018 |
| WO | 2019007418 A1 | 1/2019 |

OTHER PUBLICATIONS

Johnson et al., Relationships between drug activity in NCI preclinical in vitro and in vivo models and early clinical trials, British Journal of Cancer, 84(10): 1424-1431, 2001.*

Gura et al., Systems for identifying new drugs are often faulty, Science, 278:1041-1042, 1997.*

Simone, Oncology: Introduction, Cecil Textbook of Medicine, 20th Edition, vol. 1, pp. 1004-1010, 1996.*

Medline Plus. Hardening of the Arteries. (2018). Web: http://www.nlm.nih.gov/medlineplus/ency/article/000171.htm.

Merck Manual, Diabetes Mellitus. (2017. Web: http://www.merck.com/mmpe/print/sec12/ch_158/ch_158b.html.

Ali, et al., "Recent advances in the development of farnesoid X receptor agonists", Ann Transl Med, 3(1), 2015, 1-16.

Buijsman, et al., "Non-Steroidal Steroid Receptor Modulators", Current Medicinal Chemistry, 12, 2005, 1017-1075.

Crawley, , "Farnesoid X Receptor Modulators: a patent review", Expert Opinion on Therapeutic Patents, 20(8), 2010, 1047-1057.

Ruano, J.L. G. et al., "4-(diethoxymethyl)-3-pyridin-3-ylisoxazole-5-carboxylates: useful scaffold for highly functionalised 3-(pyridin-3-yl)isoxazole", Tetrahedron, 61(18), 2005, 4363-4371.

Sepe, et al., "Farnesoid X receptor modulators (2011-2014): a patent review", Expert Opinion on Therapeutic Patents, 25:8, 2015, 885-896.

"Pubchem CID 123486225" Create Date: Jan. 25, 2017 (Jan. 25, 2017) Date Accessed: Apr. 1, 2019 (Apr. 1, 2019).

* cited by examiner

ISOXAZOLE DERIVATIVES AS FXR AGONISTS AND METHODS OF USE THEREOF

RELATED APPLICATIONS

This application claims the benefit of U.S. Provisional Application No. 62/652,579, filed on Apr. 4, 2018 and 62/630,574 filed on Feb. 14, 2018. The entire teachings of the above applications are incorporated herein by reference.

TECHNICAL FIELD

The present invention relates generally to compounds and pharmaceutical compositions useful as FXR agonists. Specifically, the present invention relates to isoxazole compounds containing a cycloalkylamine linkage and methods for their preparation and use.

BACKGROUND OF THE INVENTION

Farnesoid X Receptor (FXR, NR1H4) is a member of the nuclear receptor family of ligand-activated transcription factors that includes receptors for the steroid, retinoid, and thyroid hormones (D. J. Mangelsdorf, et al., *Cell,* 1995, 83(6), 841-850). FXR was originally identified from a rat liver cDNA library. Farnesol and derivatives, collectively termed farnesoids, activate the rat ortholog at high concentration, but they do not modulate the human or mouse receptors. FXR is primarily expressed in the liver, kidney, and intestine (W. Seol, et al., *Mol. Endocrinol.,* 1995, 9(1), 72-85; B. M. Forman, et al., *Cell,* 1995, 81(5), 687-693). The relevant physiological ligands of FXR include the primary bile acids cholic acid (CA) and chenodeoxycholic acid (CDCA) and the secondary bile acids deoxycholic acid (DCA) and lithocholic acid (LCA) (D. Parks, et al., *Science,* 1999, 284(5418), 1362-1365). The most potent physiological ligand for FXR is CDCA, which plays a key role in regulating the expression of several genes that participate in bile acid homeostasis. FXR functions as a heterodimer with the retinoid X receptor (RXR) and binds to response elements in the promoter region of target genes to regulate gene transcription. FXR seems to be also involved in paracrine and endocrine signaling by upregulating the expression of the cytokine Fibroblast Growth Factor (J. Holt, et al., *Genes Dev.,* 2003, 17(13), 1581-1591; T. Inagaki, et al., *Cell Metab.,* 2005, 2(4), 217-225).

Small molecule compounds which act as FXR modulators have been disclosed in the following publications: WO 2000/037077, WO 2002/072598, WO 2003/015771, WO 2003/099821, WO 2004/00752, WO 2004/048349, WO 2005/009387, WO 2005/082925, US 2005/0054634, WO 2007/052843, WO 2007/070796, WO 2007/076260, WO 2007/092751, WO 2007/095174, WO 2007/140174, WO 2007/140183, US 2007/0142340, WO 2008/000643, WO 2008/002573, WO 2008/025539, WO 2008/025540, WO 2008/051942, WO 2008/073825, WO 2008/157270, US 2008/0299118, US 2008/0300235, WO 2009/005998, WO 2009/012125, WO 2009/027264, WO 2009/062874, WO 2009/127321, WO 2009/149795, US 2009/0131409, US 2009/0137554, US 2009/0163474, US 2009/0163552, US 2009/0215748, WO 2010/043513, WO 2011/020615, WO 2011/117163, WO 2012/087519, WO 2012/087520, WO 2012/087521, WO 2013/007387, WO 2013/037482, WO 2013/166176, WO 2013/192097, WO 2014/184271, US 2014/0186438, US 2014/0187633, WO 2015/017813, WO 2015/069666, WO 2016/073767, WO 2016/116054, WO 2016/103037, WO 2016/096116, WO 2016/096115, WO 2016/097933, WO 2016/081918, WO 2016/127924, WO 2016/130809, WO 2016/145295, WO 2016/173524, CN 106632294, CN 106588804, US 2017/0196893, WO 2017/062763, WO 2017/053826, CN 106518708, CN 106518946, CN 106478759, CN 106478447, CN 106478453, WO 2017/027396, WO 2017/049172, WO 2017/049173, WO 2017/049176, WO 2017/049177, WO 2017/118294, WO 2017/128896, WO 2017/129125, WO 2017/133521, WO 2017/147074, WO 2017/147174, WO 2017/145041, WO 2017/156024 A1.

Further small molecule FXR modulators have been recently reviewed (R. C. Buijsman, et al., *Curr. Med. Chem.* 2005, 12(9), 1017-1075; Crawley, M. L. *Expert Opin. Ther. Patents* 2010, 20(8), 1047-1057; V. Sepe, et al., *Expert Opin. Ther. Patents* 2015, 25(8), 885-896; Xu, Y., *J. Med. Chem.* 2016, 59 (14), 6553-6579).

There is a need for development of FXR modulators for the treatment and prevention of diseases.

SUMMARY OF THE INVENTION

In one aspect, the invention provides compounds represented by Formula I, and pharmaceutically acceptable salts thereof:

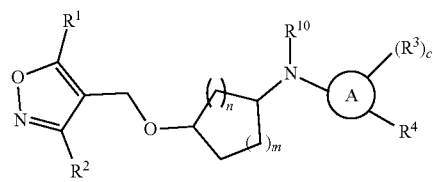

wherein:

$R^1$ is hydrogen, halogen, cyano, optionally substituted —$C_1$-$C_6$ alkyl, optionally substituted —$C_2$-$C_6$ alkenyl, optionally substituted —$C_2$-$C_6$ alkynyl, optionally substituted —$C_3$-$C_6$ cycloalkyl or optionally substituted 3- to 6-membered heterocycloalkyl. Preferably, $R^1$ is optionally substituted isopropyl, optionally substituted tert-butyl, or optionally substituted cyclopropyl.

$R^2$ is optionally substituted aryl, optionally substituted heteroaryl, optionally substituted arylalkyl, optionally substituted heteroarylalkyl, or optionally substituted cycloalkyl;

m is 0, 1, 2, or 3;

n is 0, 1, 2, or 3;

is aryl or heteroaryl;

Each $R^3$ is independently selected from the group consisting of halo, hydroxy, —OMe, —$OCH_2F$, —$OCF_3$, —$C_2$-$C_6$-alkoxy, —$C_1$-$C_6$-alkyl, —$C_1$-$C_6$ haloalkyl, —$C_2$-$C_6$ alkenyl, —$C_2$-$C_6$ alkynyl, —$C_3$-$C_6$ cycloalkyl, —O—$C_1$-$C_2$alkylphenyl, cyano, —$CH_2F$, —$CHF_2$, —$CF_3$, —$SCF_3$, —$NH_2$, —NHMe, and —$NMe_2$;

c is 0, 1 or 2;
R$^4$ is

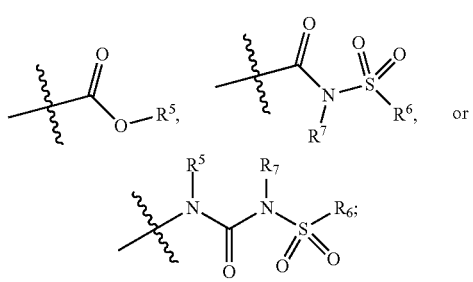

wherein
R$^5$ and R$^7$ are independently selected from the group consisting of:
1) Hydrogen;
2) Optionally substituted —C$_1$-C$_8$ alkyl;
3) Optionally substituted —C$_2$-C$_8$ alkenyl;
4) Optionally substituted —C$_2$-C$_8$ alkynyl; and
5) Optionally substituted —C$_3$-C$_8$ cycloalkyl;
R$^6$ is selected from the group consisting of:
1) Optionally substituted —C$_1$-C$_8$ alkyl;
2) Optionally substituted —C$_2$-C$_8$ alkenyl;
3) Optionally substituted —C$_2$-C$_8$ alkynyl;
4) Optionally substituted —C$_3$-C$_8$ cycloalkyl;
5) Optionally substituted aryl;
6) Optionally substituted arylalkyl;
7) Optionally substituted heterocycloalkyl;
8) Optionally substituted heteroaryl;
9) Optionally substituted heteroarylalkyl; and
10) NR$^8$R$^9$; wherein R$^8$ and R$^9$ are each independently selected from hydrogen, optionally substituted —C$_1$-C$_8$ alkyl, optionally substituted —C$_2$-C$_8$ alkenyl, optionally substituted C$_2$-C$_8$ alkynyl, optionally substituted —C$_3$-C$_8$ cycloalkyl, optionally substituted aryl, optionally substituted arylalkyl, optionally substituted heterocycloalkyl, optionally substituted heteroaryl, and optionally substituted heteroarylalkyl; alternatively, R$^8$ and R$^9$ are taken together with the nitrogen atom to which they are attached to form an optionally substituted heterocyclic ring; and
R$^{10}$ is hydrogen, optionally substituted —C$_1$-C$_6$ alkyl, optionally substituted —C$_2$-C$_6$ alkenyl, optionally substituted —C$_2$-C$_6$ alkynyl, optionally substituted —C$_3$-C$_6$ cycloalkyl, or R$^{11}$C(O)—, where R$^{11}$ is hydrogen or C$_1$-C$_4$-alkyl; preferably R$^{11}$ is hydrogen or methyl.

In another embodiment, the present invention provides a pharmaceutical composition comprising a compound or combination of compounds of the present invention, or a pharmaceutically acceptable salt thereof, and a pharmaceutically acceptable carrier or excipient.

In another embodiment, the present invention provides a method for preventing or treating an FXR mediated disease or condition in a subject in need thereof. The method comprises administering to the subject a therapeutically effective amount of a compound of Formula (I) or a pharmaceutically acceptable salt thereof. The present invention also provides the use of a compound of Formula (I) or a pharmaceutically acceptable salt thereof for the preparation of a medicament for the prevention or treatment of an FXR mediated disease or condition.

DETAILED DESCRIPTION OF THE INVENTION

In one embodiment, the present invention provides a compound of Formula (I) as described above, or a pharmaceutically acceptable salt thereof.

Compounds of Formula (I) can have the stereochemistry shown in Formula (Ia)-(Id):

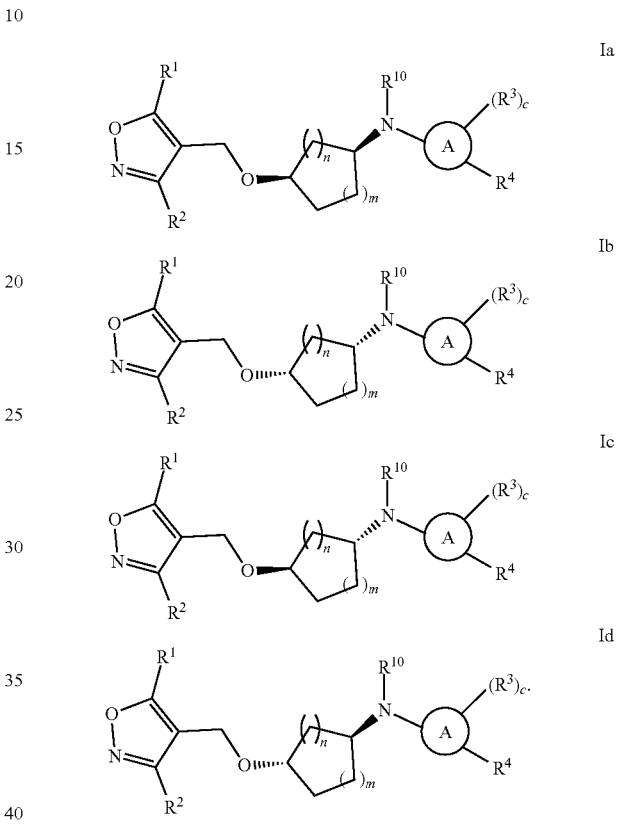

In preferred embodiments, compounds of Formula (I) have the stereochemistry shown in Formula (Ib).

In certain embodiments, the present invention relates to compounds of Formula (I), and pharmaceutically acceptable salts thereof, wherein R$^1$ is optionally substituted isopropyl, optionally substituted cyclopropyl, or optionally substituted tert-butyl.

In certain embodiments, the present invention relates to compounds of Formula (I), and pharmaceutically acceptable salts thereof, wherein R$^2$ is cyclohexyl or cyclopentyl, each of which is optionally substituted with up to 3 groups which are independently selected from halogen, optionally substituted —C$_1$-C$_6$ alkyl, optionally substituted —C$_1$-C$_6$ alkoxy, optionally substituted —C$_3$-C$_6$ cycloalkyl, optionally substituted, —C$_3$-C$_6$ cycloalkenyl, optionally substituted aryl, and optionally substituted heteroaryl.

In certain embodiments, the present invention relates to compounds of Formula (I), and pharmaceutically acceptable salts thereof, wherein R$^2$ is cyclopropyl which is optionally substituted with up to 2 groups which are independently selected from of halogen, optionally substituted —C$_1$-C$_6$ alkyl, optionally substituted —C$_1$-C$_6$ alkoxy, optionally substituted —C$_3$-C$_6$ cycloalkyl, optionally substituted —C$_3$-C$_6$ cycloalkenyl, optionally substituted aryl, and optionally substituted heteroaryl.

In certain embodiments, the present invention relates to compounds of Formula (I), and pharmaceutically acceptable salts thereof, wherein $R^2$ is optionally substituted phenyl.

In certain embodiments, the present invention relates to compounds of Formula (I), and pharmaceutically acceptable salts thereof, wherein $R^2$ is optionally substituted heteroaryl.

In certain embodiments, the present invention relates to compounds of Formula (I), and pharmaceutically acceptable salts thereof, wherein $R^2$ is selected from the groups set forth below:

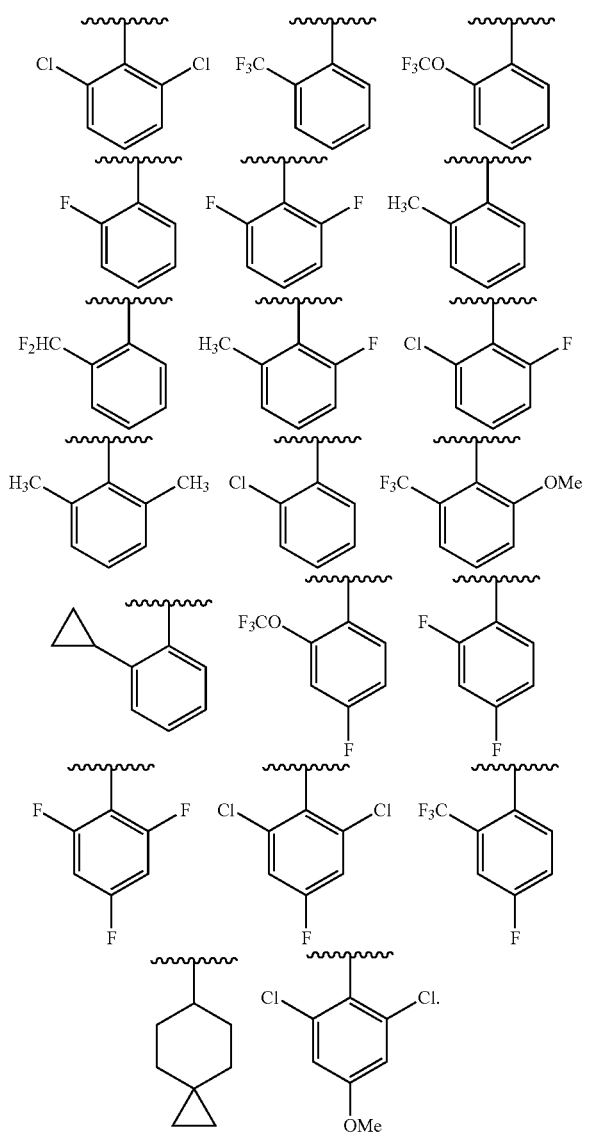

In certain embodiments, the present invention relates to compounds of Formula (I), and pharmaceutically acceptable salts thereof, wherein m is 1 and n is 1.

In certain embodiments, the present invention relates to compounds of Formula (I), and pharmaceutically acceptable salts thereof, wherein m is 1 and n is 2.

In certain embodiments, the present invention relates to compounds of Formula (I), and pharmaceutically acceptable salts thereof, wherein m is 2 and n is 1.

In certain embodiments, the present invention relates to compounds of Formula (I), and pharmaceutically acceptable salts thereof, wherein m is 2 and n is 2.

In certain embodiments, the present invention relates to compounds of Formula (I), and pharmaceutically acceptable salts thereof, wherein $R^{10}$ is hydrogen, methyl, or cyclopropyl.

In certain embodiments, the present invention relates to compounds of Formula (I), and pharmaceutically acceptable salts thereof, wherein (A)

is selected from the groups set forth below by removal of one hydrogen atom:

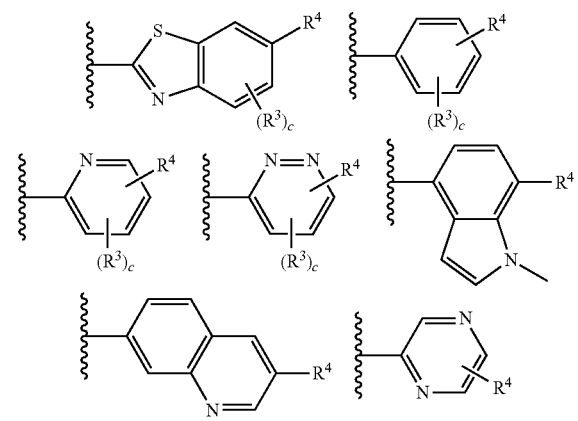

In certain embodiments, the present invention relates to compounds of Formula (I), and pharmaceutically acceptable salts thereof, wherein is selected from the groups set forth below:

wherein R³, R⁴, and c are as previously defined.

In certain embodiments, the invention provides compounds represented by Formula (II) and pharmaceutically acceptable salts thereof:

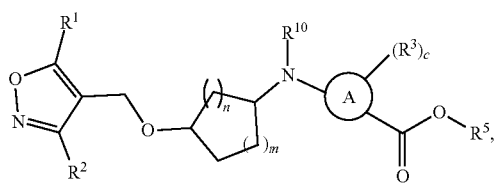

II wherein R¹, R², m, n, (A),

R³, c, R¹⁰ and R⁵ are as previously defined. Preferably, R⁵ is hydrogen.

In certain embodiments, the invention provides compounds represented by Formula (III) and pharmaceutically acceptable salts thereof:

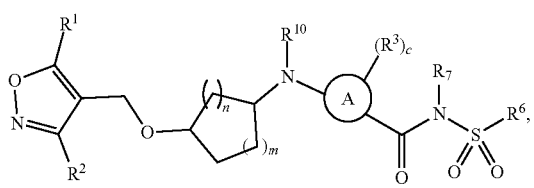

III wherein R¹, R², m, n, (A),

R¹⁰, R³, R⁷ and R⁶ are as previously defined.

In certain embodiments, the invention provides compounds represented by Formula (IV), and pharmaceutically acceptable salts thereof:

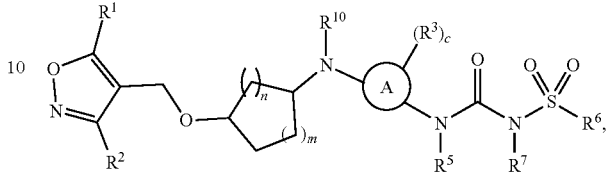

IV wherein R¹, R², m, n, (A), r¹⁰, R³, c, R⁵, R⁷ and R⁶ are as previously defined.

In certain embodiments, the invention provides compounds represented by Formula (V), and pharmaceutically acceptable salts thereof:

V wherein R², m, n, (A),

R³, c, R¹⁰ and R⁴ are as previously defined.

In certain embodiments, the invention provides compounds represented by Formula (VIa) or Formula (VIb), and pharmaceutically acceptable salts thereof:

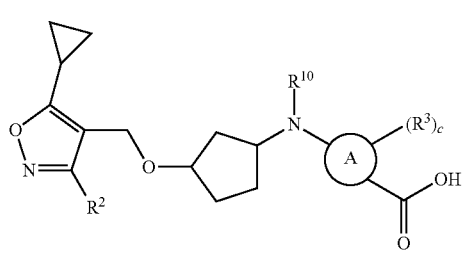

VIa

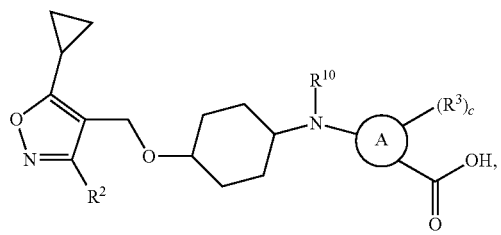

VIb wherein $R^2$,

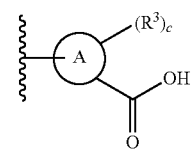

$R^3$, c, and $R^{10}$ are as previously defined. Preferably, $R^3$ is halogen, or —O—$^i$Pr; $R^{10}$ is hydrogen or methyl; and $R^2$ is selected from the groups set forth below:

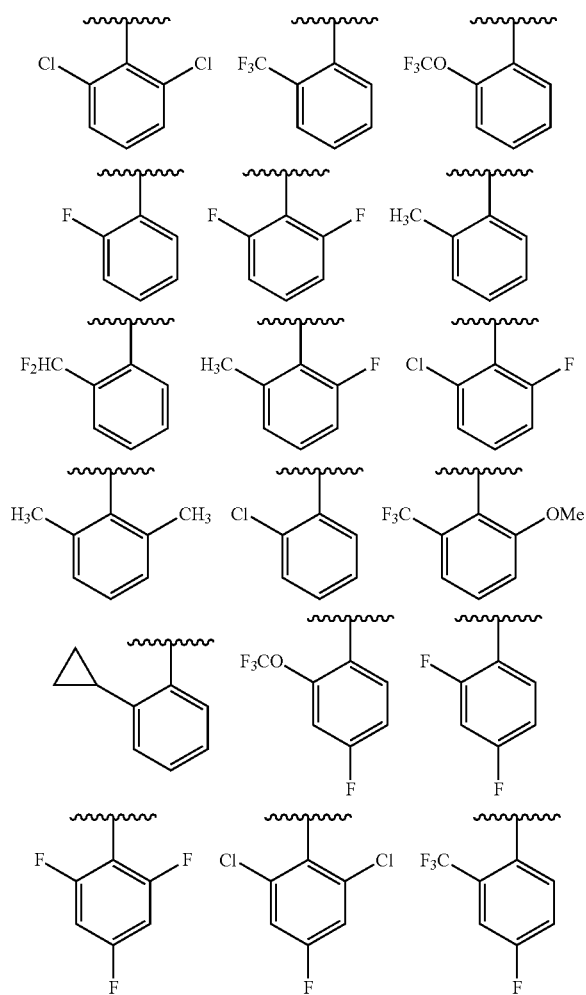

In certain embodiments, the invention provides compounds represented by Formula (VIa) or Formula (VIb), wherein $R^2$, $R^{10}$, and are delineated for each compound in Table 1.

TABLE 1

| Entry | $R^2$ | $R^{10}$ | |
|---|---|---|---|
| 1a | 2,6-dichlorophenyl | H | quinoline-5-COOH (2-linked) |
| 2a | 2,6-dichlorophenyl | H | quinoline-6-COOH (2-linked) |
| 3a | 2,6-dichlorophenyl | H | quinoxaline-5-COOH |
| 4a | 2,6-dichlorophenyl | H | quinoxaline-6-COOH |
| 5a | 2,6-dichlorophenyl | H | pyrazine-COOH |

TABLE 1-continued
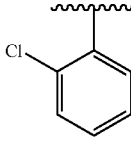
| Entry | R² | R¹⁰ | |
|---|---|---|---|
| 6a | 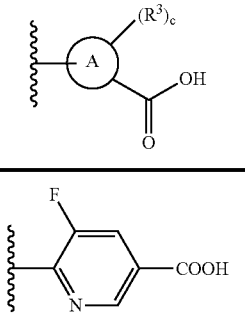 | H | 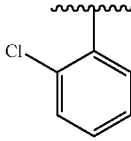 |
| 7a | 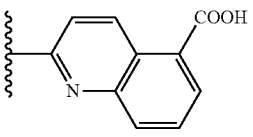 [SMILES: *c1ccc2c(C(=O)O)cccc2n1] | Me | 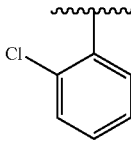 |
| 8a | 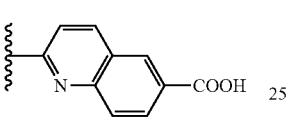 | Me | 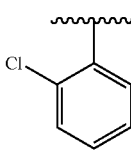 |
| 9a | 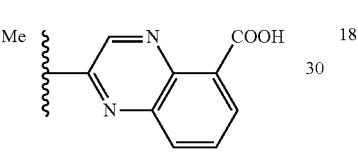 | Me | 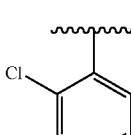 |
| 10a | 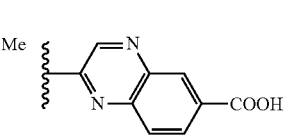 | Me | 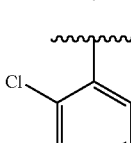 |
| 11a | 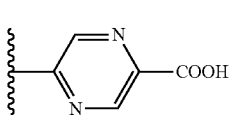 | Me | 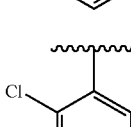 |
| 12a | 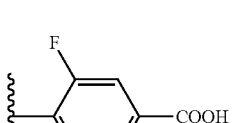 | Me | 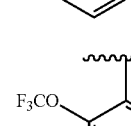 |
| 13a | 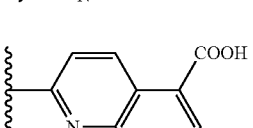 | H | 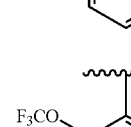 |
| 14a | 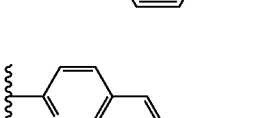 | H | 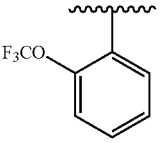 |
| 15a | 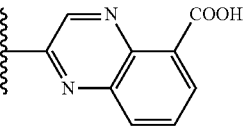 [SMILES: *c1cnc2c(C(=O)O)cccc2n1] | H | 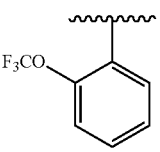 |
| 16a | 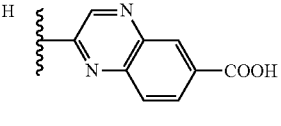 | H | 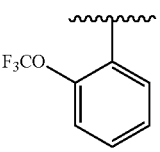 |
| 17 | 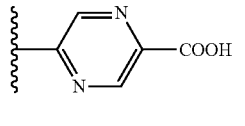 | H | 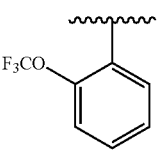 |
| 18 | 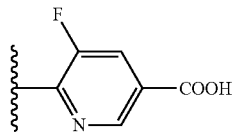 [SMILES: *c1ncc(C(=O)O)cc1F] | H | 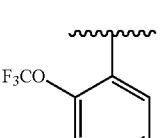 |
| 19a | 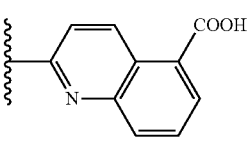 [SMILES: *c1ccc2c(C(=O)O)cccc2n1] | Me | 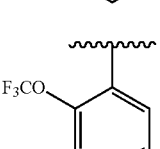 |
| 20a | 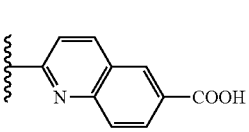 [SMILES: *c1ccc2cc(C(=O)O)ccc2n1] | Me | 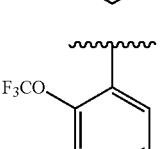 |
| 21a | 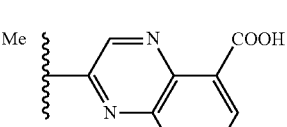 | Me | 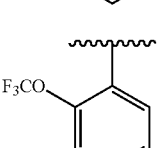 |
| 22a | 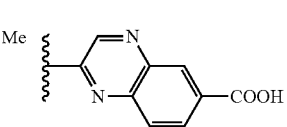 | Me | 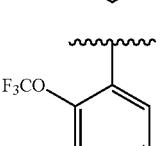 |
| 23a | 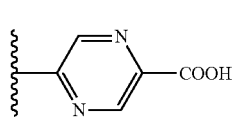 [SMILES: *c1cnc(C(=O)O)cn1] | Me | |

TABLE 1-continued

| Entry | R² | R¹⁰ | ![A-COOH structure] |
|---|---|---|---|
| 24a | 2-F₃CO-phenyl | Me | 5-F-pyridine-COOH |
| 25a | 2,6-difluorophenyl | H | quinoline-5-COOH |
| 26a | 2,6-difluorophenyl | H | quinoline-6-COOH |
| 27a | 2,6-difluorophenyl | H | quinoxaline-5-COOH |
| 28a | 2,6-difluorophenyl | H | quinoxaline-6-COOH |
| 29a | 2,6-difluorophenyl | H | pyrazine-COOH |
| 30a | 2,6-difluorophenyl | H | 3-F-pyridine-5-COOH |
| 31a | 2,6-difluorophenyl | Me | quinoline-5-COOH |
| 32a | 2,6-difluorophenyl | Me | quinoline-6-COOH |
| 33a | 2,6-difluorophenyl | Me | quinoxaline-5-COOH |
| 34a | 2,6-difluorophenyl | Me | quinoxaline-6-COOH |
| 35a | 2,6-difluorophenyl | Me | pyrazine-COOH |
| 36a | 2,6-difluorophenyl | Me | 3-F-pyridine-5-COOH |

In certain embodiments, the invention provides compounds represented by Formula (VIIa) or Formula (VIIb), or a pharmaceutically acceptable salt thereof:

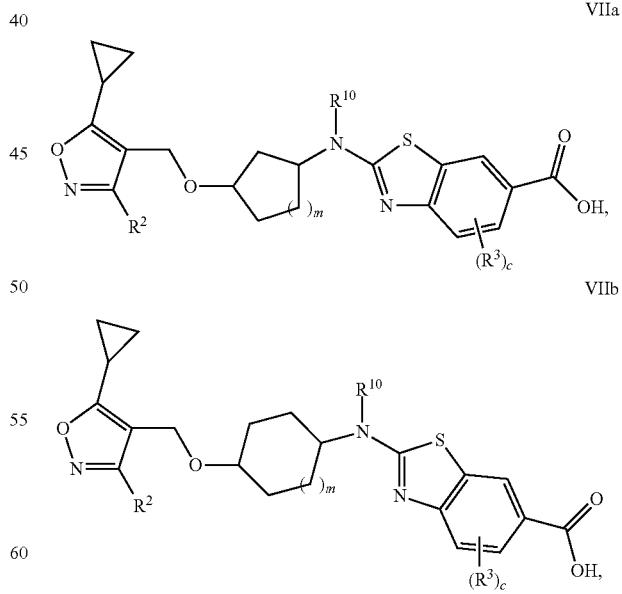

VIIa

VIIb wherein $R^2$, m, c, $R^3$, and $R^{10}$ are as previously defined.

In certain embodiments, the invention provides compounds represented by Formula (VIIa-1) or Formula (VIIb-1), or a pharmaceutically acceptable salt thereof:

VIIa-1

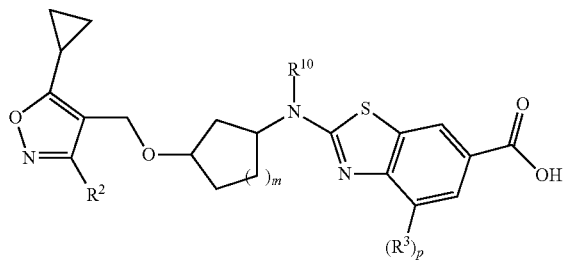

VIIb-1

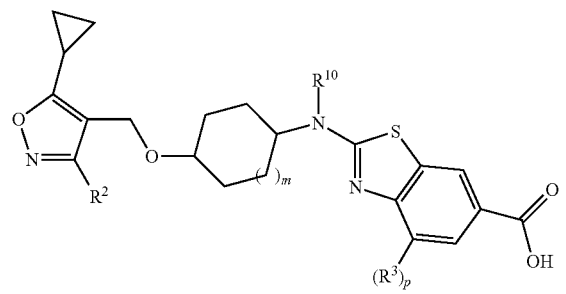

wherein p is 0 or 1; R², m, R³, and R¹⁰ are as previously defined.

In certain embodiments, the invention provides compounds represented by Formula (VIIa-b) or Formula (VIIb-b), or a pharmaceutically acceptable salt thereof:

VIIa-b

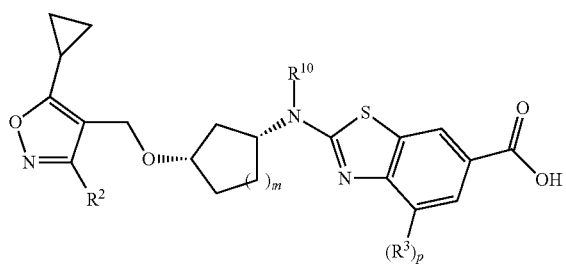

VIIb-b

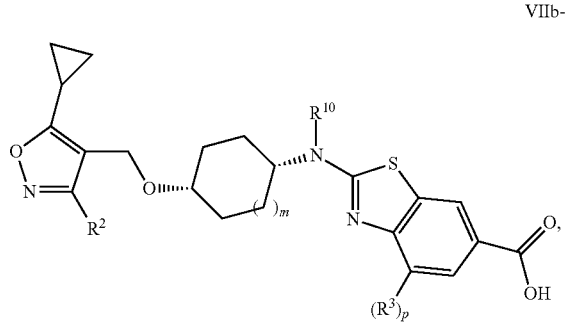

wherein p, R², m, R³, and R¹⁰ are as previously defined.

In certain embodiments, the invention provides compounds represented by Formula (VIIa-1), Formula (VIIb-1), Formula (VIIa-b), or Formula (VIIb-b), and pharmaceutically acceptable salts thereof, wherein p is 1, and R², m, R¹⁰ and R³ are delineated for each compound in Table 2.

TABLE 2

| Entry | R² | m | R¹⁰ | R³ |
|---|---|---|---|---|
| 1b | 2,6-diCl-phenyl | 0 | H | F |
| 2b | 2,6-diCl-phenyl | 0 | H | Oi-Pr |
| 3b | 2,6-diCl-phenyl | 0 | Me | F |
| 4b | 2,6-diCl-phenyl | 0 | Me | Oi-Pr |
| 5b | 2,6-diCl-phenyl | 0 | cyclopropyl | F |
| 6b | 2,6-diCl-phenyl | 0 | cyclopropyl | Oi-Pr |
| 7b | 2,6-diCl-phenyl | 1 | H | F |
| 8b | 2,6-diCl-phenyl | 1 | H | Oi-Pr |
| 9b | 2,6-diCl-phenyl | 1 | Me | F |
| 10b | 2,6-diCl-phenyl | 1 | Me | Oi-Pr |

TABLE 2-continued

| Entry | R² | m | R¹⁰ | R³ |
|---|---|---|---|---|
| 11b | 2,6-dichlorophenyl | 1 | cyclopropyl | F |
| 12b | 2,6-dichlorophenyl | 1 | cyclopropyl | Oi-Pr |
| 13b | 2,6-dichlorophenyl | 2 | H | F |
| 14b | 2,6-dichlorophenyl | 2 | H | Oi-Pr |
| 15b | 2,6-dichlorophenyl | 2 | Me | F |
| 16b | 2,6-dichlorophenyl | 2 | Me | Oi-Pr |
| 17b | 2,6-dichlorophenyl | 2 | cyclopropyl | F |
| 18b | 2,6-dichlorophenyl | 2 | cyclopropyl | Oi-Pr |
| 19b | 2-(trifluoromethoxy)phenyl | 0 | H | F |
| 20b | 2-(trifluoromethoxy)phenyl | 0 | H | Oi-Pr |
| 21b | 2-(trifluoromethoxy)phenyl | 0 | Me | F |
| 22b | 2-(trifluoromethoxy)phenyl | 0 | Me | Oi-Pr |
| 23b | 2-(trifluoromethoxy)phenyl | 0 | cyclopropyl | F |
| 24b | 2-(trifluoromethoxy)phenyl | 0 | cyclopropyl | Oi-Pr |
| 25b | 2-(trifluoromethoxy)phenyl | 1 | H | F |
| 26b | 2-(trifluoromethoxy)phenyl | 1 | H | Oi-Pr |
| 27b | 2-(trifluoromethoxy)phenyl | 1 | Me | F |
| 28b | 2-(trifluoromethoxy)phenyl | 1 | Me | Oi-Pr |
| 29b | 2-(trifluoromethoxy)phenyl | 1 | cyclopropyl | F |
| 30b | 2-(trifluoromethoxy)phenyl | 1 | cyclopropyl | Oi-Pr |

TABLE 2-continued
| Entry | R² | m | R¹⁰ | R³ |
|---|---|---|---|---|
| 31b | 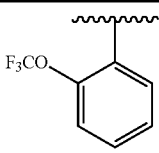 | 2 | H | F |
| 32b | 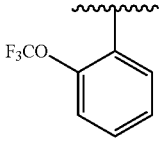 | 2 | H | Oi-Pr |
| 33b | 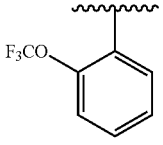 | 2 | Me | F |
| 34b | 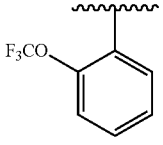 | 2 | Me | Oi-Pr |
| 35b | 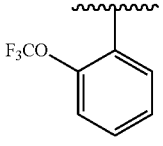 | 2 |  | F |
| 36b | 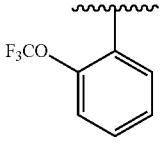 | 2 | 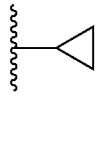 | Oi-Pr |
| 37b | 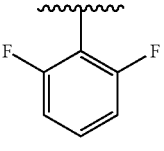 | 0 | H | F |
| 38b | 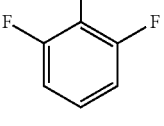 | 0 | H | Oi-Pr |
| 39b | 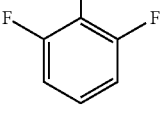 | 0 | Me | F |
| 40b | 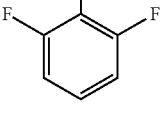 | 0 | Me | Oi-Pr |
| 41b | 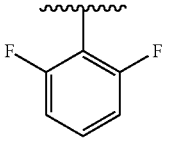 [SMILES: *c1c(F)cccc1F] | 0 | 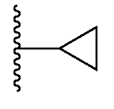 | F |
| 42b | 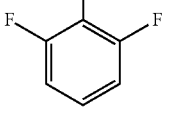 | 0 | 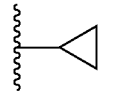 | Oi-Pr |
| 43b | 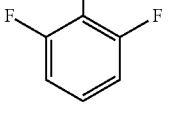 | 1 | H | F |
| 44b | 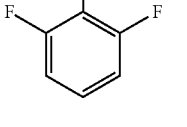 | 1 | H | Oi-Pr |
| 45b | 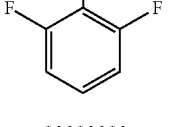 | 1 | Me | F |
| 46b | 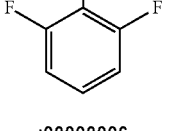 | 1 | Me | Oi-Pr |
| 47b | 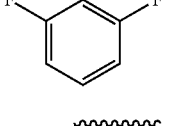 | 1 |  | F |
| 48b | 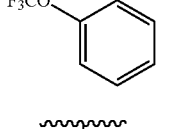 | 1 |  | Oi-Pr |
| 49b | 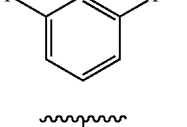 | 2 | H | F |
| 50b | 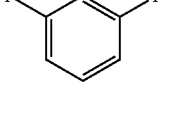 | 2 | H | Oi-Pr |

TABLE 2-continued

| Entry | R² | m | R¹⁰ | R³ |
|---|---|---|---|---|
| 51b | 2,6-difluorophenyl | 2 | Me | F |
| 52b | 2,6-difluorophenyl | 2 | Me | Oi-Pr |
| 53b | 2,6-difluorophenyl | 2 | cyclopropyl | F |
| 54b | 2,6-difluorophenyl | 2 | cyclopropyl | Oi-Pr |

In certain embodiments, the invention provides compounds represented by Formulae (VIIIa)~(VIIId), and pharmaceutically acceptable salts thereof:

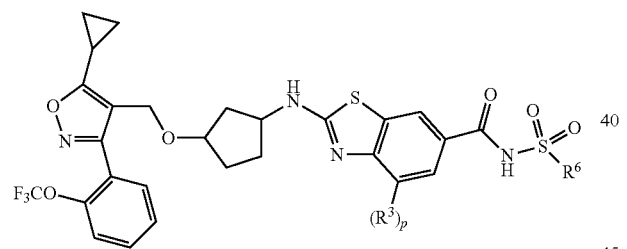

VIIIa

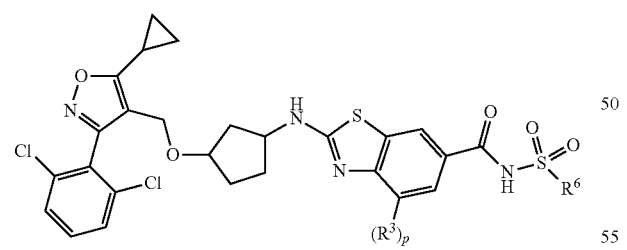

VIIIb

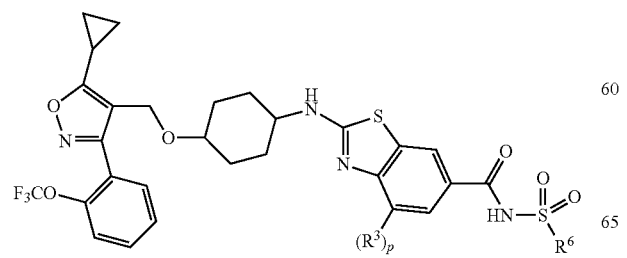

VIIIc

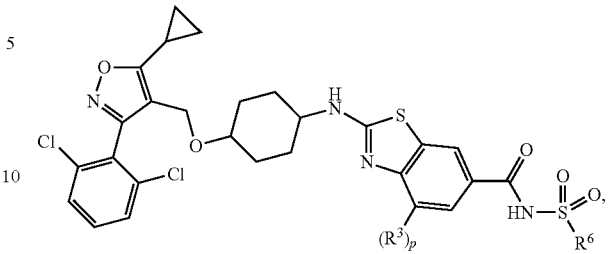

VIIId wherein p, $R^3$ and $R^6$ are as previously defined.

In certain embodiments, the invention provides compounds represented by Formulae (VIIIa)~(VIIId), and pharmaceutically acceptable salts thereof, wherein p is 1, and $R^3$ and $R^6$ are delineated for each compound in Table 3.

TABLE 3

| Entry | R³ | R⁶ |
|---|---|---|
| 1c | Oi-Pr | Methyl |
| 2c | Oi-Pr | Ethyl |
| 3c | Oi-Pr | Isopropyl |
| 4c | Oi-Pr | Butyl |
| 5c | Oi-Pr | t-Butyl |
| 6c | Oi-Pr | Propyl |
| 7c | Oi-Pr | Benzyl |
| 8c | Oi-Pr | Vinyl |
| 9c | Oi-Pr | Allyl |
| 10c | Oi-Pr | —CF₃ |
| 11c | Oi-Pr |  |
| 12c | Oi-Pr |  |
| 13c | Oi-Pr | 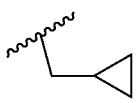 [SMILES: *CC1CC1] |
| 14c | Oi-Pr | 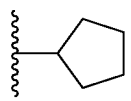 |
| 15c | Oi-Pr | 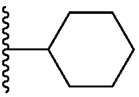 |
| 16c | Oi-Pr | 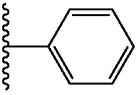 |
| 17c | Oi-Pr | 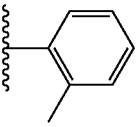 |

TABLE 3-continued

| Entry | R³ | R⁶ |
|---|---|---|
| 18c | Oi-Pr | 4-methylphenyl |
| 19c | Oi-Pr | 4-(OCF₃)phenyl |
| 20c | Oi-Pr | 4-t-butylphenyl |
| 21c | Oi-Pr | 2-(OCF₃)phenyl |
| 22c | Oi-Pr | 2-fluorophenyl |
| 23c | Oi-Pr | 2-naphthyl |
| 24c | Oi-Pr | —NH₂ |
| 25c | Oi-Pr | —NHCH₃ |
| 26c | Oi-Pr | —N(CH₃)₂ |
| 27c | Oi-Pr | pyrrolidin-1-yl |
| 28c | Oi-Pr | piperidin-1-yl |
| 29c | Oi-Pr | morpholin-4-yl |
| 30c | F | Methyl |
| 31c | F | Ethyl |
| 32c | F | Isopropyl |
| 33c | F | Butyl |
| 34c | F | t-Butyl |
| 35c | F | Propyl |
| 36c | F | Benzyl |
| 37c | F | Vinyl |
| 38c | F | Allyl |
| 39c | F | —CF₃ |
| 40c | F | cyclopropyl |
| 41c | F | 1-methylcyclopropyl |
| 42c | F | cyclopropylmethyl |
| 43c | F | cyclopentyl |
| 44c | F | cyclohexyl |
| 45c | F | phenyl |
| 46c | F | 2-methylphenyl |
| 47c | F | 4-methylphenyl |
| 48c | F | 4-(OCF₃)phenyl |
| 49c | F | 4-t-butylphenyl |
| 50c | F | 2-(OCF₃)phenyl |
| 51c | F | 2-fluorophenyl |
| 52c | F | 2-naphthyl |
| 53c | F | —NH₂ |
| 54c | F | —NHCH₃ |
| 55c | F | —N(CH₃)₂ |

TABLE 3-continued

| Entry | R³ | R⁶ |
|---|---|---|
| 56c | F | 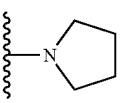 |
| 57c | F | 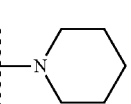 |
| 58c | F | 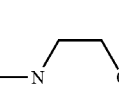 |

In certain embodiments, the invention provides compounds represented by Formulae (IXa)~(IXd), and pharmaceutically acceptable salts thereof:

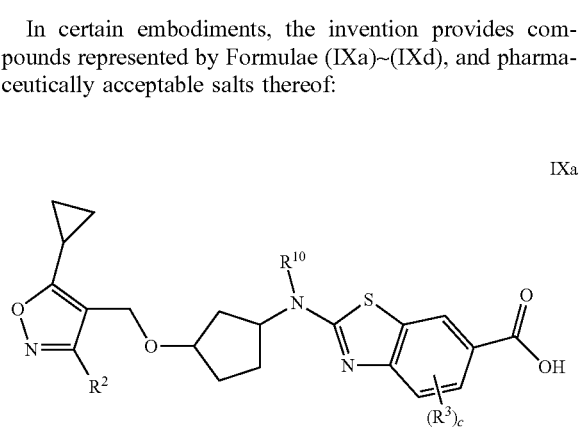

IXa

IXb

IXc

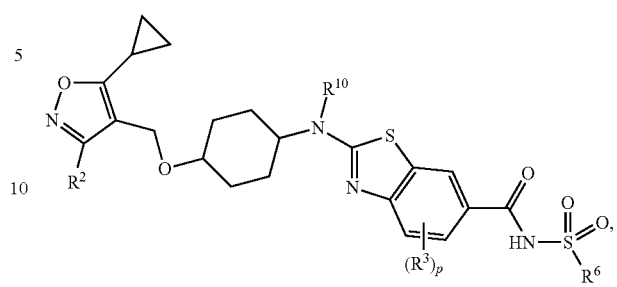

IXd wherein c, $R^2$, $R^3$, $R^6$ and $R^{10}$ are as previously defined.

In certain embodiments, the invention provides compounds represented by Formulae (IXa-b)~(IXd-b), and pharmaceutically acceptable salts thereof:

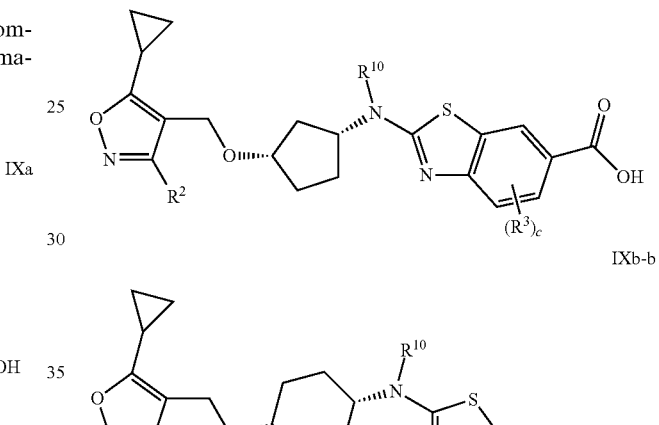

IXa-b

IXb-b

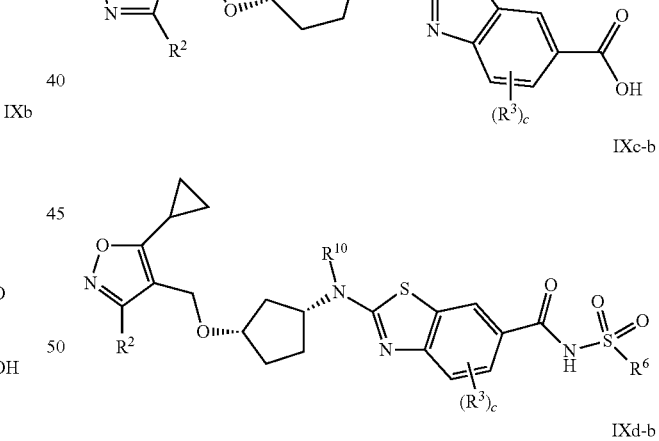

IXc-b

IXd-b wherein c, $R^2$, $R^3$, $R^6$ and $R^{10}$ are as previously defined.

In certain embodiments, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesterolemia, or hyperlipidemia chronic liver disease, gastrointestinal disease, fibrotic diseases such as primary biliary cirrhosis, primary sclerosing cholangitis, pulmonary fibrosis, renal fibrosis, liver fibrosis, renal disease, metabolic disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In one aspect, the compound is a selective FXR agonist over TGR5 activator.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted.

The term "heteroarylalkyl," as used herein, refers to a C$_1$-C$_3$ alkyl or C$_1$-C$_6$ alkyl residue attached to a heteroaryl ring. Examples include, but are not limited to, pyridinylmethyl, pyrimidinylethyl and the like.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are (C$_1$-C$_3$) alkoxy.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

It is understood that any alkyl, alkenyl, alkynyl, cycloalkyl, heterocyclic and cycloalkenyl moiety described herein can also be an aliphatic group or an alicyclic group. The term "substituted" as used herein, refers to independent replacement of one, two, three or more of the hydrogen atoms thereon with substituents including, but not limited to, deuterium, tritium, —F, —Cl, —Br, —I, —OH, C$_1$-C$_{12}$-alkyl; C$_2$-C$_{12}$-alkenyl, C$_2$-C$_{12}$-alkynyl, protected hydroxy, —NO$_2$, —CN, —NH$_2$, —N$_3$, protected amino, alkoxy, thioalkoxy, oxo, thioxo, -halo-C$_1$-C$_{12}$-alkyl, -halo-C$_2$-C$_{12}$-alkenyl, -halo-C$_2$-C$_{12}$-alkynyl, -halo-C$_3$-C$_{12}$-cycloalkyl, —NH—C$_1$-C$_{12}$-alkyl, —NH—C$_2$-C$_{12}$-alkenyl, —NH—C$_2$-C$_{12}$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-

$C_{12}$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, methylthiomethyl, or -L'-R', wherein L' is C$_1$-C$_6$alkylene, C$_2$-C$_6$alkenylene or C$_2$-C$_6$alkynylene, and R' is aryl, heteroaryl, heterocyclic, C$_3$-C$_{12}$cycloalkyl or C$_3$-C$_{12}$cycloalkenyl. In certain embodiments, the substituents are independently selected from halo, preferably Cl and F; C$_1$-C$_4$-alkyl, preferably methyl and ethyl; halo-C$_1$-C$_4$-alkyl, such as fluoromethyl, difluoromethyl, and trifluoromethyl; C$_2$-C$_4$-alkenyl; halo-C$_2$-C$_4$-alkenyl; C$_3$-C$_6$-cycloalkyl, such as cyclopropyl; C$_1$-C$_4$-alkoxy, such as methoxy and ethoxy; halo-C$_1$-C$_4$-alkoxy, such as fluoromethoxy, difluoromethoxy, and trifluoromethoxy, —CN; —OH; NH$_2$; C$_1$-C$_4$-alkylamino; di(C$_1$-C$_4$-alkyl)amino; and NO$_2$. It is understood that the aryls, heteroaryls, alkyls, and the like can be further substituted. In some cases, each substituent in a substituted moiety is additionally optionally substituted when possible with one or more groups, each group being independently selected from C$_1$-C$_4$-alkyl; —CF$_3$, —OCH$_3$, —OCF$_3$, —F, —Cl, —Br, —I, —OH, —NO$_2$, —CN, and —NH$_2$. Preferably, a substituted alkyl group, such as a substituted methyl group, is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenylmethyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2$^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water, the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
Alloc for allyloxycarbonyl;
Boc for tert-butoxycarbonyl;
Cbz for benzyloxycarbonyl;
BOP-Cl for bis(2-oxo-3-oxazolidinyl)phosphinic chloride;
CDI for carbonyldiimidazole;
DBU for 1,8-diazabicycloundec-7-ene;
DCC for N,N-dicyclohexylcarbodiimide;
DCM for dichloromethane;
DMAP for N,N-dimethylaminopyridine;
DMF for N,N-dimethyl formamide;
DPPA for diphenylphosphoryl azide;
EDC for 1-(3-diethylaminopropyl)-3-ethylcarbodiimide hydrochloride;
$Et_3N$ for triethylamine;
EtOAc for ethyl acetate;
HATU for 1-[bis(dimethylamino)methylene]-1H-1,2,3-triazolo[4,5-b]pyridinium 3-oxid hexafluorophosphate;
HCl for hydrochloric acid;
MTBE for methyl tert-butyl ether;
MeOH for methanol;
PG for protecting group;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
TBS for tert-butyl dimethyl silyl;
TBDPS for tert-butyl diphenyl silyl;
TIPS for triisopropyl silyl;
TFFH for tetramethylfluoroformamidinium hexafluorophosphate;
THF for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

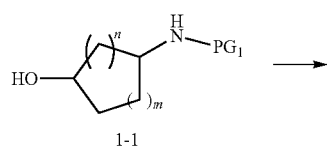

Scheme 1

As shown in Scheme 1, isoxazole carboxylate compound of Formula (II) and acylsulfonamide compound of Formula (III), wherein $R^1$, $R^2$, m, n, $R^{10}$,

$R^3$, c, $R^5$, $R^6$, and $R^7$ are as previously defined, are prepared from the compound of Formula (1-1), wherein m and n are previously defined and $PG_1$ is the protecting group of the amino group such as, but not limited to, Boc, Cbz, Bn, Alloc, etc. The free alcohol of (1-1) is protected with base-resistant protecting group $PG_2$ such as, but not limited to, TBS, TBDPS, TIPS, etc., providing compound of Formula (1-2). Under basic conditions alkylation of the amino group of compound of Formula (1-2) with $R^{10}X$, wherein $R^{10}$ is previously defined and X is Br, I, Cl, OMs, or OTf, etc., affords compound of formula (1-3). Removal of the alcohol protecting group $PG_2$ followed by alkylation with compound of formula (1-4) wherein $R^1$ and $R^2$ are previously defined and X is Br, I, Cl, OMs, or OTf, etc., gives ether compound of formula (1-5). Removal of the protecting group $PG_1$ on the amine, followed by alkylation of the amine with compound of formula (1-6) wherein $R^3$, c, and $R^5$ are previous defined and X is Br, I, Cl, OMs, or OTf, etc., provides a compound of formula (II). Hydrolysis of the ester compound of formula (II), followed by coupling the resulting carboxylic acid ($R^5$=H) with a sulfonamide compound of formula (1-7), wherein $R^6$ and $R^7$ are previously defined, gives the acylsulfonamide compound of formula (III). The coupling reagent can be selected from, but is not limited to, DCC, EDC, CDI, diisopropyl carbodiimide, BOP-Cl, PyBOP, PyAOP, TFFH, HATU and CITU.

Scheme 2

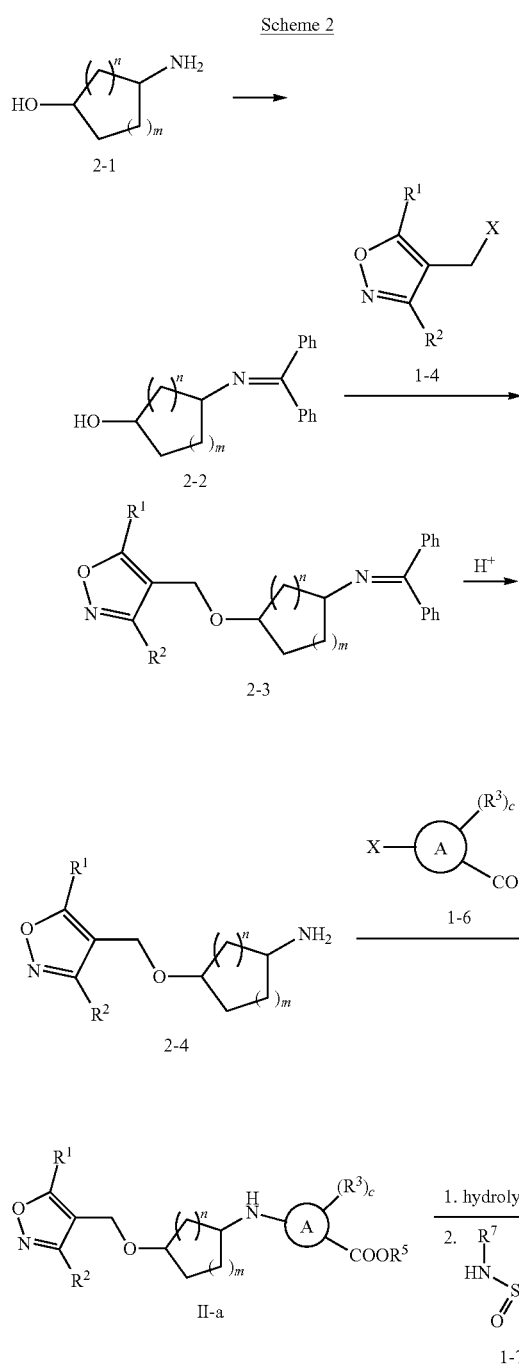

As shown in Scheme 2, isoxazole compound of Formula (II-a) and Formula (III-a) are prepared from the compound of Formula (2-1), wherein $R^1$, $R^2$, m, n,

$R^3$, c, $R^5$, $R^6$, and $R^7$ are as previously defined. Protecting of the amino group of compound of formula (2-1) with benzophenone imine provides compound of formula (2-2). Alkylation of the alcohol of (2-2) under basic conditions with compound of formula (1-4), wherein $R^1$, $R^2$ and X are previously defined, gives ether compound of formula (2-3). Hydrolysis of the benzophenone imine moiety of compound of formula (2-3) under acidic conditions affords free amine compound of formula (2-4). Alkylation of the amino group of compound of formula (2-4) under basic conditions with compound of formula (1-6), wherein $R^3$, c, $R^5$, and X are previously defined, provides compound of formula (II-a). Hydrolysis of the ester compound of formula (II-a), followed by coupling the resulted carboxylic acid ($R^5$=H) with sulfonamide compound of formula (1-7), wherein $R^6$ and $R^7$ are previously defined, gives the acylsulfonamide compound of formula (III-a).

Scheme 3

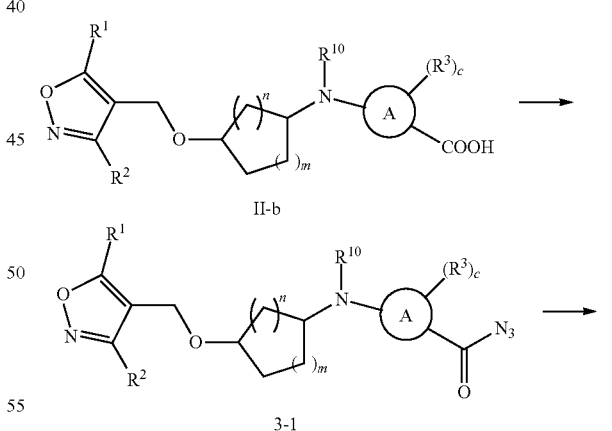

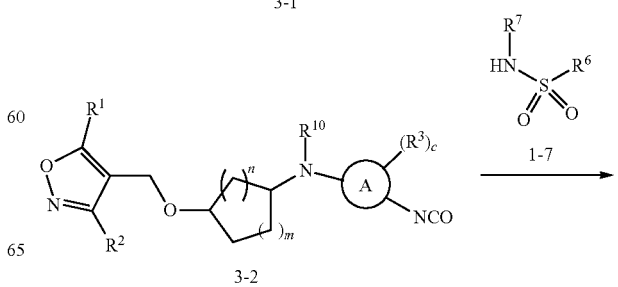

-continued

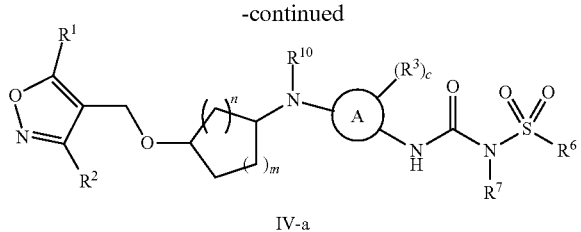

IV-a

As shown in Scheme 3, a sulfonyl urea compound of Formula (IV-a) is prepared from the carboxylic acid compound of Formula (II-b), wherein $R^1$, $R^2$, m, n, $R^{10}$, (A), $R^3$, and c are as previously defined. The carboxylic acid compound of Formula (II-b) is converted to the acyl azide compound of Formula (3-1) using a suitable reagent such as, but not limited to, DPPA. Further Curtius rearrangement of the compound of Formula (3-1) at elevated temperature provides the isocyanate compound of Formula (3-2). Reacting of compound (3-2) under basic conditions with sulfonamide compound of formula (1-7), wherein $R^6$ and $R^7$ are previously defined, affords the sulfonylurea compound of Formula (IV-a), wherein $R^1$, $R^2$, m, n, $R^{10}$, (A), $R^3$, c, $R^7$, and $R^6$ are as previously defined.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Example 1

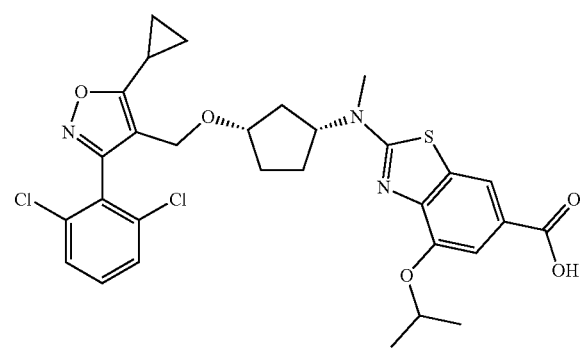 [SMILES: CC(C)Oc1cc(C(=O)O)cc2sc(N(C)[C@@H]3CC[C@H](OCc4c(-c5c(Cl)cccc5Cl)noc4C4CC4)C3)nc12]

Step 1-1:

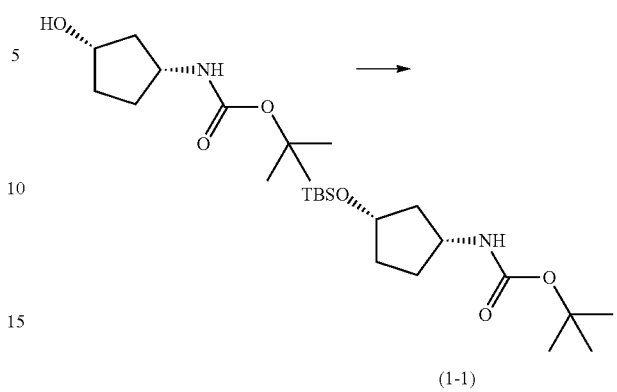

tert-Butyl ((1R,3S)-3-hydroxycyclopentyl)carbamate (372 mg, 1.848 mmol) was dissolved in DMF (6 ml). TBS-Cl (612 mg, 4.07 mmol) and imidazole (554 mg, 8.14 mmol) was added. The mixture was stirred at rt for 5 hrs, quenched with water, and extracted with MTBE. The collected organic layer was washed with water and brine, dried over $Na_2SO_4$, and concentrated in vacuo. Purification of the residue on silica gel with 0-30% EtOAc/hexane provided compound (1-1) (550 mg, 94% yield).

$^1$H NMR (400 MHz, Chloroform-d) δ 5.32 (d, J=8.2 Hz, 1H), 4.31 (dt, J=4.9, 2.3 Hz, 1H), 4.10 (d, J=8.6 Hz, 1H), 1.96 (q, J=10.8, 9.2 Hz, 1H), 1.89-1.78 (m, 1H), 1.78-1.64 (m, 3H), 1.42 (s, 9H), 0.89 (s, 9H), 0.06 (s, 6H).

Step 1-2:

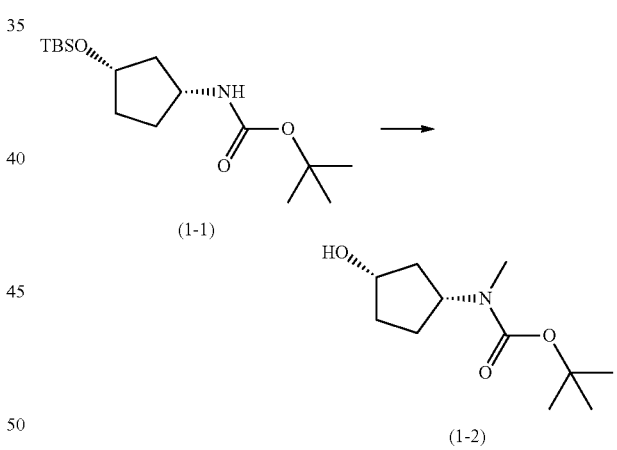

Compound (1-1) (260 mg, 0.824 mmol) was dissolved in DMF (2747 μl). Sodium tert-butoxide (158 mg, 1.648 mmol) and iodomethane (77 μl, 1.236 mmol) was added. The mixture was stirred at rt for 2 h, quenched with water, and extracted with hexane. The organic layer was dried over $Na_2SO_4$ and concentrated in vacuo. The crude product (239 mg, 0.725 mmol) was dissolved in MeOH (7.2 mL) and 37% HCl (6 μl, 0.073 mmol) was added. The mixture was stirred at rt for 30 min and concentrated in vacuo. Purification of the residue on silica gel with 0-50% EtOAc/hexane provided compound (1-2) (132 mg, 0.613 mmol, 85% yield).

$^1$H NMR (400 MHz, Chloroform-d) δ 4.33-4.16 (m, 2H), 2.83 (s, 3H), 2.18 (ddd, J=14.2, 9.9, 5.9 Hz, 1H), 2.00-1.86 (m, 1H), 1.86-1.69 (m, 2H), 1.63 (dtd, J=17.7, 8.9, 8.1, 4.1 Hz, 2H), 1.45 (s, 9H).

Step 1-3:

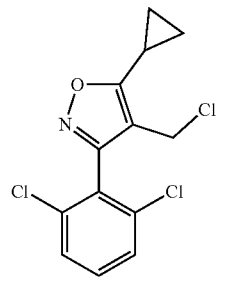

+

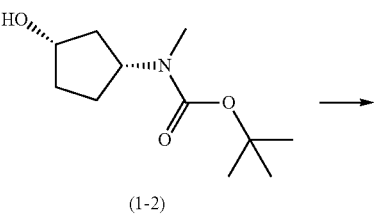

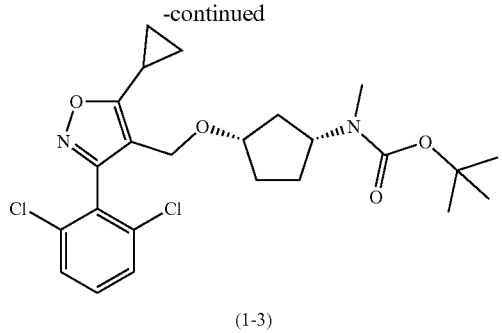

To a solution of compound (1-2) (72 mg, 0.334 mmol) and 4-(chloromethyl)-5-cyclopropyl-3-(2,6-dichlorophenyl)isoxazole (152 mg, 0.50 mmol) in DMSO (2.2 mL) was added KOt-Bu (113 mg, 1.003 mmol). The mixture was stirred at rt for 1 h, quenched with sat. NH$_4$Cl, and extracted with MTBE (2×). The combined organic layer was dried over Na$_2$SO$_4$ and concentrated. Purification of the residue on silica gel with 0-20% EtOAc/hexane provided compound (1-3) (69 mg, 0.143 mmol, 42.9% yield).

$^1$H NMR (400 MHz, Chloroform-d) δ 7.51-7.32 (m, 3H), 4.42 (s, 1H), 4.25 (s, 2H), 3.86-3.69 (m, 1H), 2.65 (s, 3H), 2.15 (tt, J=8.4, 5.1 Hz, 1H), 2.00 (ddd, J=15.0, 8.9, 6.3 Hz, 1H), 1.46 (s, 9H), 1.32-1.24 (m, 2H), 1.18-1.09 (m, 2H).

Step 1-4:

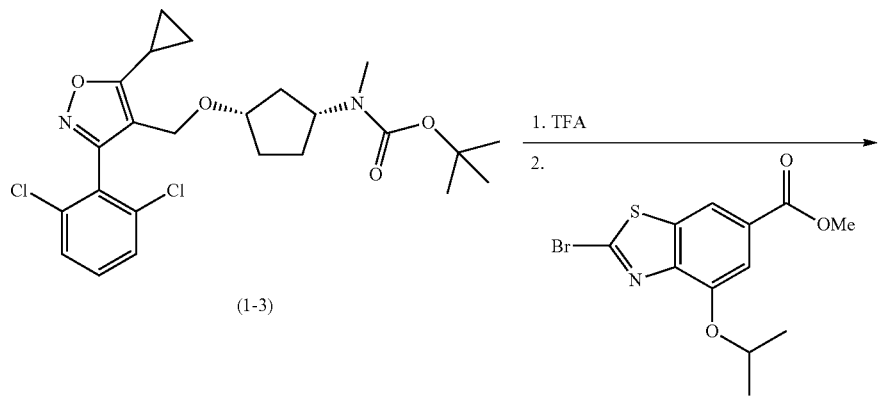

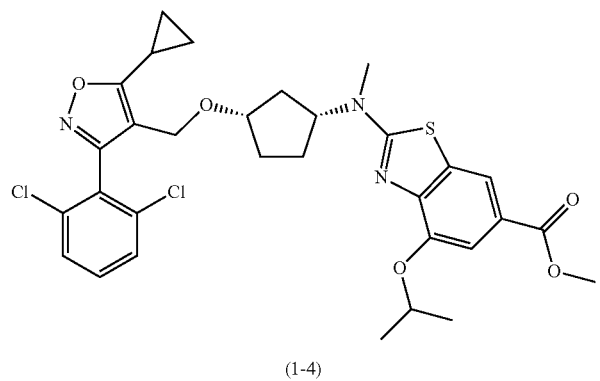

To a solution of compound (1-3) (69 mg, 0.143 mmol) in CH$_2$Cl$_2$ (0.44 ml) was added trifluoroacetic acid (0.221 ml, 2.87 mmol). The mixture was stirred at rt for 30 min and concentrated in vacuo, and dried under vacuum overnight. The crude product (M+1, 383) was and dissolved in DMA (778 μl). Methyl 2-bromo-4-isopropoxybenzo[d]thiazole-6-carboxylate (61.7 mg, 0.187 mmol) and cesium carbonate (152 mg, 0.467 mmol) was added. The mixture was stirred at 65° C. for 3.5 h, quenched with water, and extracted with EtOAc. The organic layer was dried and concentrated in vacuo. Purification of the residue on silica gel with 0-30% EtOAc/hexane provided compound (1-4) (48 mg, 0.076 mmol, 48.9% yield). $^1$H NMR (400 MHz, Chloroform-d) δ 7.95 (d, J=1.6 Hz, 1H), 7.53 (d, J=1.5 Hz, 1H), 7.47-7.41 (m, 2H), 7.39-7.32 (m, 1H), 4.84 (hept, J=6.1 Hz, 1H), 4.65 (s, 1H), 4.29 (s, 2H), 3.92 (s, 3H), 3.87 (dt, J=5.9, 3.6 Hz, 1H), 3.03 (d, J=2.8 Hz, 3H), 2.27-2.11 (m, 2H), 1.96-1.81 (m, 1H), 1.79-1.63 (m, 2H), 1.63-1.48 (m, 2H), 1.45 (d, J=6.1 Hz, 6H), 1.20-1.10 (m, 2H). [M+H]$^+$ m/z 630.17.

Step 1-5:

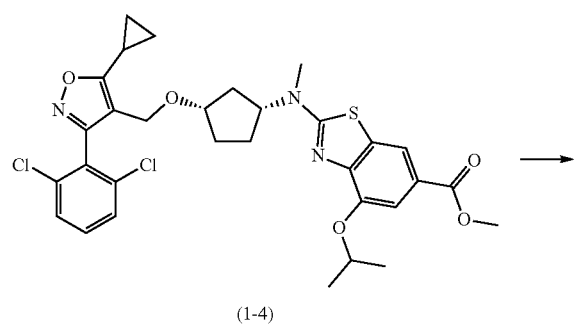

(1-4)

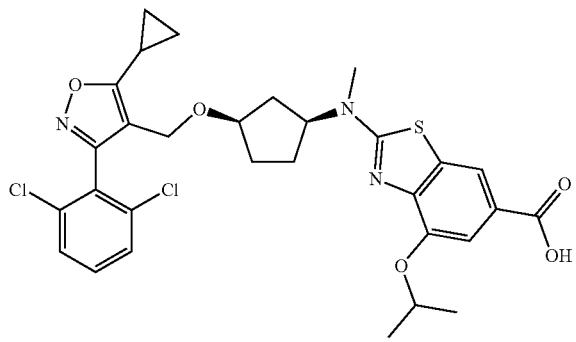 [SMILES: CC(C)Oc1cc(C(=O)O)cc2sc(N(C)[C@H]3CC[C@@H](OCc4c(-c5c(Cl)cccc5Cl)noc4C4CC4)C3)nc12]

Example 1

Compound (1-4) (48 mg, 0.076 mmol) was dissolved in THF (507 μl), MeOH (507 μl), and Water (507 μl). A 10 M aq. solution of sodium hydroxide (152 μl, 1.522 mmol) was added. The mixture was stirred at 50° C. for 1 h, cooled to rt, quenched with 1 M HCl (1.5 mL), and extracted with EtOAc. Purification of the organic layer on silica gel with 0-50% acetone/hexane provided Example 1 (35 mg, 0.057 mmol, 74.6% yield).

1H NMR (500 MHz, Chloroform-d) δ 8.02 (d, J=1.5 Hz, 1H), 7.59 (d, J=1.6 Hz, 1H), 7.50-7.40 (m, 2H), 7.36 (dd, J=8.6, 7.6 Hz, 1H), 4.85 (hept, J=6.1 Hz, 1H), 4.68 (s, 1H), 4.30 (s, 2H), 3.87 (dt, J=6.0, 3.3 Hz, 1H), 3.05 (s, 3H), 2.31-2.06 (m, 2H), 1.99-1.82 (m, 1H), 1.79-1.66 (m, 2H), 1.64-1.52 (m, 2H), 1.47 (d, J=6.1 Hz, 6H), 1.38-1.25 (m, 2H), 1.25-1.11 (m, 2H). [M+H]$^+$ m/z 616.15.

Example 2

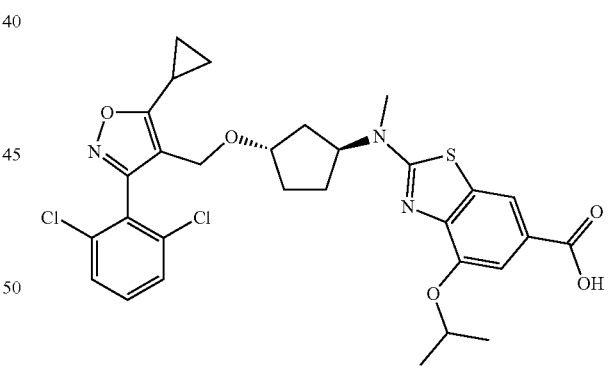

Example 2 was synthesized from tert-butyl ((1S,3R)-3-hydroxycyclopentyl)carbamate following the same procedure of preparation of Example 1. 1H NMR (500 MHz, Chloroform-d) δ 8.01 (d, J=1.5 Hz, 1H), 7.59 (d, J=1.6 Hz, 1H), 7.45 (d, J=7.9 Hz, 2H), 7.36 (dd, J=8.7, 7.5 Hz, 1H), 4.85 (hept, J=6.1 Hz, 1H), 4.73 (s, 1H), 4.30 (s, 2H), 3.88 (dq, J=5.9, 3.7, 2.7 Hz, 1H), 3.06 (s, 3H), 2.31-2.23 (m, 1H), 2.18-2.10 (m, 1H), 1.91 (dd, J=11.4, 6.2 Hz, 1H), 1.79-1.65 (m, 2H), 1.64-1.53 (m, 2H), 1.53-1.40 (m, 6H), 1.22-1.09 (m, 2H). [M+H]$^+$ m/z 616.15.

Example 3

Example 3 was synthesized from tert-butyl ((1S,3S)-3-hydroxycyclopentyl)carbamate following the same procedure of preparation of Example 1. 1H NMR (400 MHz, Chloroform-d) δ 8.04 (d, J=1.6 Hz, 1H), 7.59 (d, J=1.6 Hz, 1H), 7.49 (ddd, J=9.2, 8.1, 1.2 Hz, 2H), 7.37 (t, J=8.1 Hz, 1H), 4.86 (hept, J=6.0 Hz, 1H), 4.61-4.42 (m, 1H), 4.28 (d, J=1.3 Hz, 2H), 3.97 (dd, J=5.6, 3.1 Hz, 1H), 3.12 (s, 3H), 2.16 (dt, J=8.4, 5.0 Hz, 1H), 2.04-1.84 (m, 3H), 1.80-1.55 (m, 3H), 1.47 (dd, J=6.1, 0.9 Hz, 6H), 1.37-1.23 (m, 2H), 1.20-1.10 (m, 2H). [M+H]$^+$ m/z 616.15.

Example 4

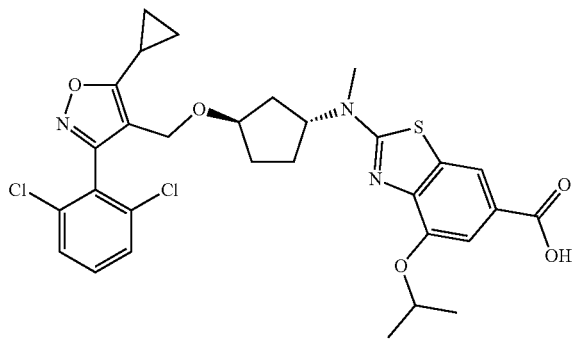 [SMILES: CC(C)Oc1cc(C(=O)O)cc2sc(N(C)[C@@H]3CC[C@@H](OCc4c(-c5c(Cl)cccc5Cl)noc4C4CC4)C3)nc12]

Example 4 was synthesized from tert-butyl ((1R,3R)-3-hydroxycyclopentyl)carbamate following the same procedure of preparation of Example 1. $^1$E NMR (400 MHz, Chloroform-d) δ 8.04 (d, J=1.6 Hz, 1H), 7.59 (d, J=1.6 Hz, 1H), 7.49 (ddd, J=9.2, 8.1, 1.2 Hz, 2H), 7.37 (t, J=8.1 Hz, 1H), 4.86 (hept, J=6.0 Hz, 1H), 4.61-4.42 (m, 1H), 4.28 (d, J=1.3 Hz, 2H), 3.97 (dd, J=5.6, 3.1 Hz, 1H), 3.12 (s, 3H), 2.16 (dt, J=8.4, 5.0 Hz, 1H), 2.04-1.84 (m, 3H), 1.80-1.55 (m, 3H), 1.47 (dd, J=6.1, 0.9 Hz, 6H), 1.37-1.23 (m, 2H), 1.20-1.10 (m, 2H). [M+H]$^+$ m/z 616.15.

Example 5

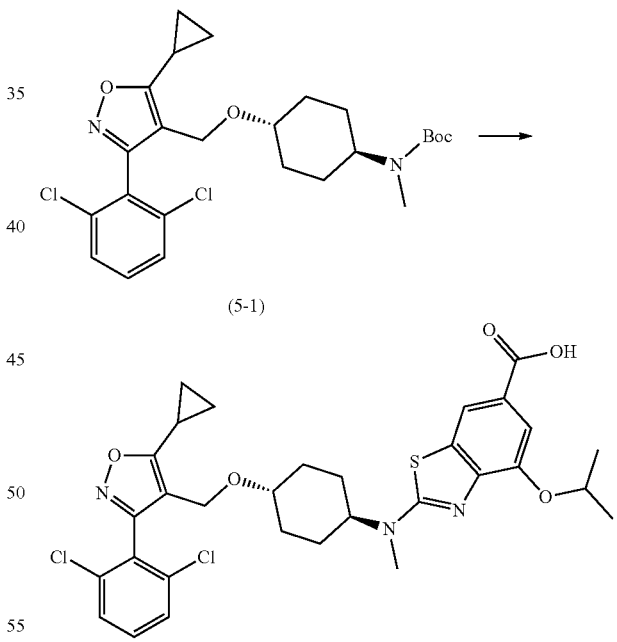

Step 5-1:

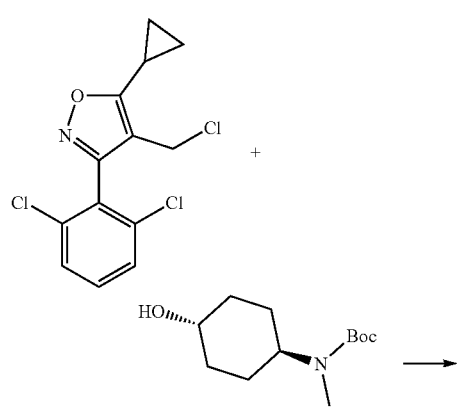

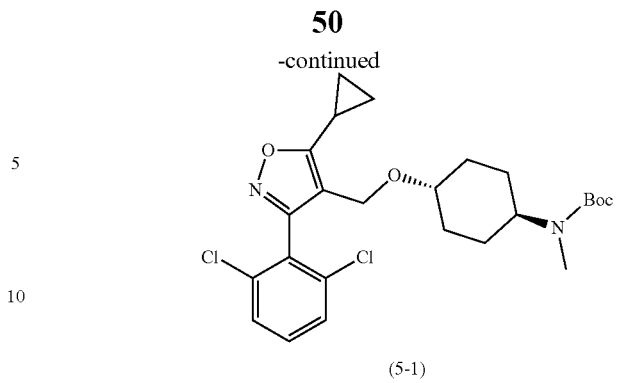

(5-1)

To a solution of tert-butyl ((trans)-4-hydroxycyclohexyl)(methyl)carbamate (150 mg, 0.654 mmol) in DMF (3271 μl) was added sodium tert-butoxide (189 mg, 1.962 mmol) and 4-(chloromethyl)-5-cyclopropyl-3-(2,6-dichlorophenyl)isoxazole (198 mg, 0.654 mmol). The mixture was stirred at rt for 1 h, quenched with sat. NH$_4$Cl, and extracted with MTBE (2×). The combined organic layer was concentrated in vacuo. Purification of the residue on 20 g of silica gel with 0-50% EtOAc/hexane provided compound (5-1) (75 mg, 0.151 mmol, 23.14% yield). $^1$H NMR (400 MHz, Chloroform-d) δ 7.46-7.30 (m, 3H), 4.30 (s, 2H), 3.85 (br s, 1H), 3.05 (tt, J=10.8, 4.2 Hz, 1H), 2.66 (s, 3H), 2.15 (tt, J=8.4, 5.1 Hz, 1H), 1.84 (d, J=12.5 Hz, 2H), 1.71-1.53 (m, 3H), 1.44 (s, 9H), 1.40-1.05 (m, 7H).

Step 5-2:

Example 5 was synthesized from compound (5-1) following same protocol as shown in Step 1-4 and 1-5. $^1$H NMR (400 MHz, Chloroform-d) δ 8.03 (t, J=1.7 Hz, 1H), 7.59 (d, J=1.5 Hz, 1H), 7.51-7.43 (m, 2H), 7.38 (dd, J=9.1, 6.9 Hz, 1H), 4.84 (hept, J=6.4 Hz, 1H), 4.36 (s, 2H), 3.98 (s, 1H), 3.25-3.00 (m, 4H), 2.19 (tt, J=8.4, 5.1 Hz, 1H), 2.07-1.79 (m, 4H), 1.69-1.51 (m, 2H), 1.46 (dd, J=6.1, 1.6 Hz, 6H), 1.40-1.23 (m, 4H), 1.16 (dt, J=8.4, 3.4 Hz, 2H). [M+H]$^+$ m/z 630.17.

Example 6

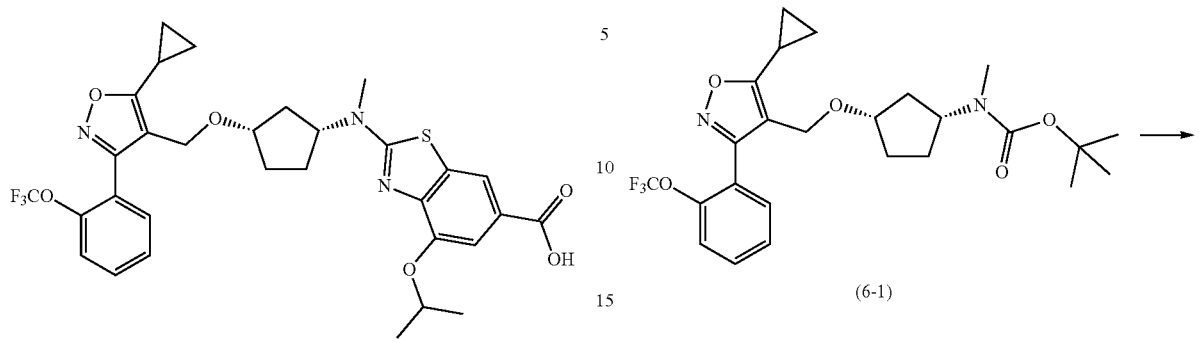

Step 6-1:

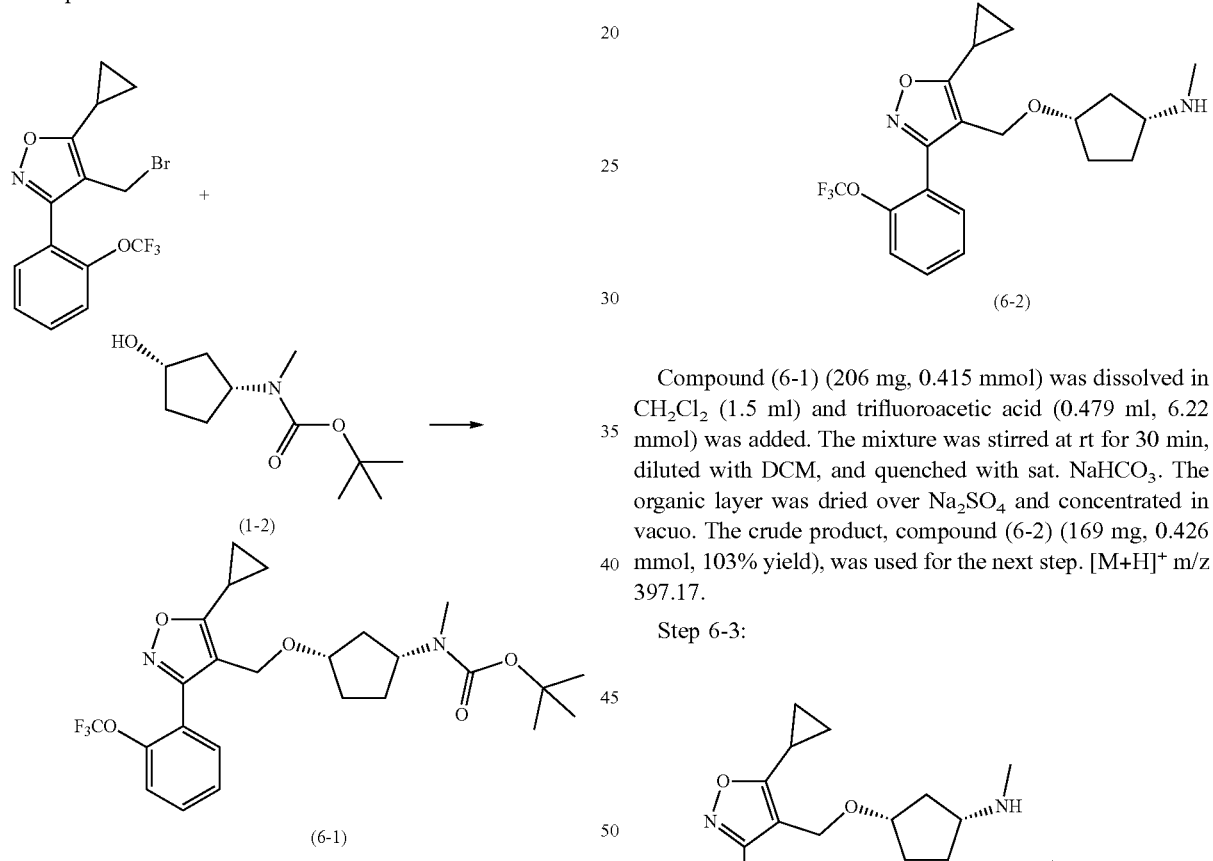

Compound (1-2) (132 mg, 0.613 mmol) and 4-(bromomethyl)-5-cyclopropyl-3-(2-(trifluoromethoxy)phenyl)isoxazole (274 mg, 0.757 mmol) was dissolved in DMF (1.5 ml) and NaOt-Bu (118 mg, 1.226 mmol) was added. The mixture was stirred at rt for 1 h, quenched with water, and extracted with MTBE (2×). The combined organic layer was dried over Na$_2$SO$_4$, and concentrated in vacuo. Purification of the residue on silica gel with 0-30% EtOAc/hexane provided compound (6-1) (206 mg, 0.415 mmol, 67.7% yield). $^1$H NMR (400 MHz, Chloroform-d) δ 7.64-7.48 (m, 2H), 7.46-7.35 (m, 2H), 4.46 (s, 1H), 4.39-4.22 (m, 2H), 3.91-3.72 (m, 1H), 2.63 (s, 3H), 2.22-2.11 (m, 1H), 2.07-1.97 (m, 1H), 1.75-1.52 (m, 5H), 1.46 (s, 9H), 1.35-1.20 (m, 4H), 1.16-1.05 (m, 2H).

Step 6-2:

Compound (6-1) (206 mg, 0.415 mmol) was dissolved in CH$_2$Cl$_2$ (1.5 ml) and trifluoroacetic acid (0.479 ml, 6.22 mmol) was added. The mixture was stirred at rt for 30 min, diluted with DCM, and quenched with sat. NaHCO$_3$. The organic layer was dried over Na$_2$SO$_4$ and concentrated in vacuo. The crude product, compound (6-2) (169 mg, 0.426 mmol, 103% yield), was used for the next step. [M+H]$^+$ m/z 397.17.

Step 6-3:

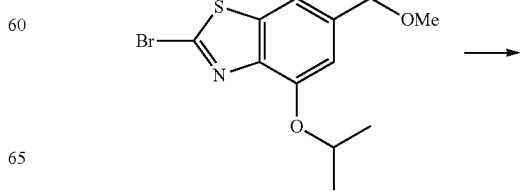

-continued

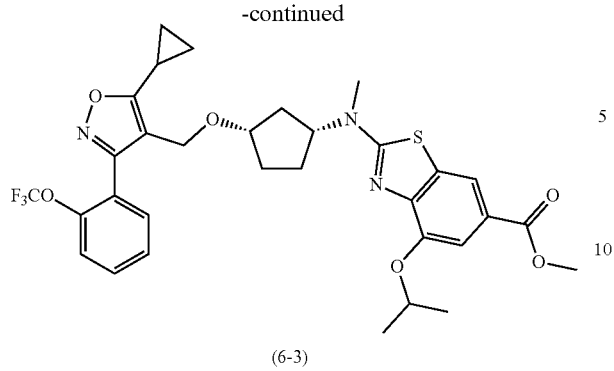

(6-3)

Compound (6-2) (50 mg, 0.126 mmol) and methyl 2-bromo-4-isopropoxybenzo[d]thiazole-6-carboxylate (45.8 mg, 0.139 mmol) was dissolved in DMA (631 µl) and cesium carbonate (82 mg, 0.252 mmol) was added. The mixture was stirred at 80° C. for 2.5 h, cooled to rt, quenched with water, and extracted with MTBE (2×). The combined organic layer was dried over $Na_2SO_4$ and concentrated in vacuo. Purification of the residue on silica gel with 0-50% EtOAc/hexane provided compound (6-3) (18 mg, 0.028 mmol, 22.10% yield). $[M+H]^+$ m/z 646.22.

Step 6-4:

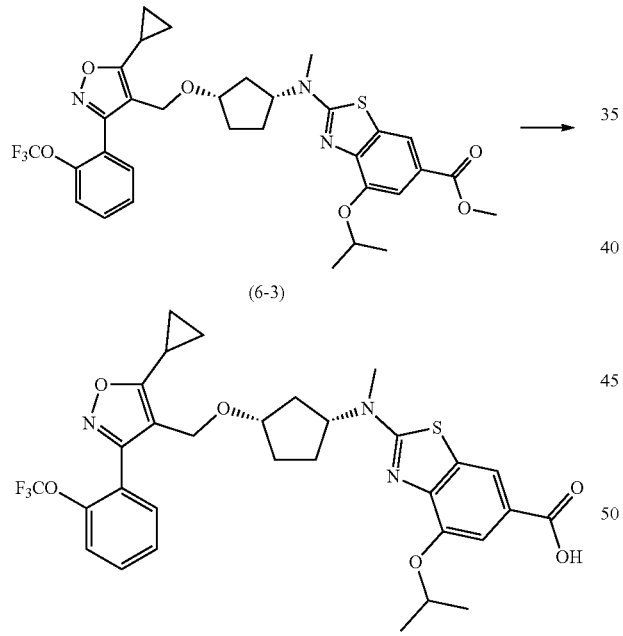

Example 6

Compound (6-3) (18 mg, 0.028 mmol) was dissolved in THF (0.5 ml), MeOH (0.5 ml), and water (0.5 ml). A 10 M aq. solution of sodium hydroxide (0.167 ml, 1.673 mmol) was added. The mixture was stirred at 65° C. for 1 h, quenched with 1 M HCl (1.7 mL), and extracted with EtOAc. The organic layer was concentrated in vacuo. Purification of the residue on silica with 0-50% acetone/hexane provided Example 6 (7 mg, 0.011 mmol, 39.8% yield). $^1$H NMR (400 MHz, Chloroform-d) δ 7.97 (d, J=1.3 Hz, 1H), 7.64-7.49 (m, 3H), 7.47-7.36 (m, 2H), 4.85 (m, 2H), 4.48-4.24 (m, 2H), 3.91 (br s, 1H), 3.04 (s, 3H), 2.42-1.54 (m, 7H), 1.49 (d, J=6.1 Hz, 6H), 1.31-1.23 (m, 2H), 1.19-1.09 (m, 2H). $[M+H]^+$ m/z 632.20.

Example 7

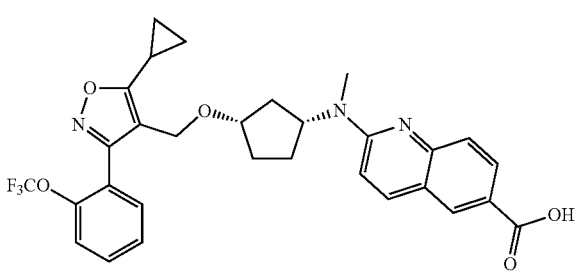 [SMILES: CN(c1ccc2cc(C(=O)O)ccc2n1)[C@@H]1CC[C@H](OCc2c(-c3ccccc3OC(F)(F)F)noc2C2CC2)C1]

Step 7-1.

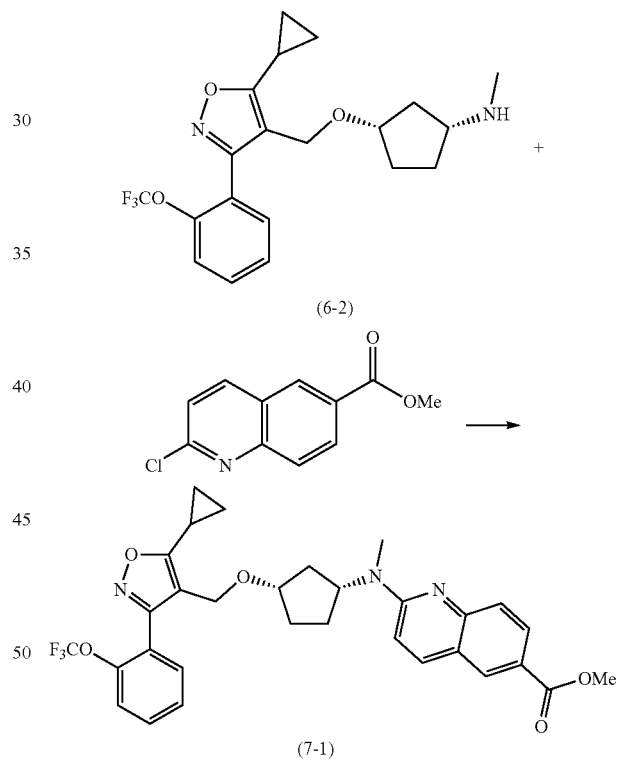

(7-1)

Compound (6-2) (63 mg, 0.159 mmol) and methyl 2-chloroquinoline-6-carboxylate (70.4 mg, 0.318 mmol) was dissolved in DMA (795 µl). Cesium carbonate (104 mg, 0.318 mmol) was added. The mixture was stirred at 90° C. for 16 h, cooled to rt, quenched with water, and extracted with EtOAc (2×). The combined organic layer was dried and concentrated in vacuo. Purification of the residue on silica gel with 0-30% EtOAc/hexane provided compound (7-1) (26 mg, 0.045 mmol, 28.1% yield). $[M+H]^+$ m/z 582.22.

Step 7-2.

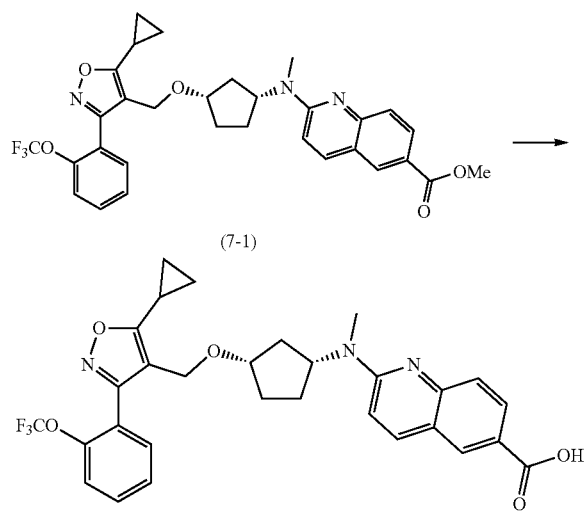

(7-1)

Example 7

Compound (7-1) (26 mg, 0.045 mmol) was dissolved in THF (298 µl), MeOH (298 µl), and water (298 µl). A 10 M aq. solution of sodium hydroxide (89 µl, 0.894 mmol) was added. The mixture was stirred at 50° C. for 1 h, quenched with 1 M HCl (0.9 mL), and extracted with EtOAc. Purification of the organic layer on 12 g of silica gel with 0-50% acetone/hexane provided Example 7 (12.6 mg, 0.022 mmol, 49.7% yield). $^1$H NMR (400 MHz, Methanol-d4) δ 8.38 (d, J=2.0 Hz, 1H), 8.20-8.00 (m, 2H), 7.73-7.59 (m, 3H), 7.59-7.42 (m, 2H), 7.15 (d, J=9.4 Hz, 1H), 5.30-5.09 (m, 1H), 4.55-4.30 (m, 2H), 3.96 (tt, J=5.5, 2.8 Hz, 1H), 2.99 (s, 3H), 2.40-2.13 (m, 2H), 1.92-1.50 (m, 5H), 1.26-1.08 (m, 4H). [M+H]$^+$ m/z 568.21.

Example 8

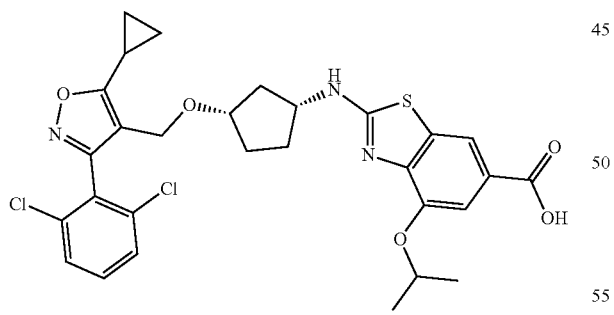

Step 8-1.

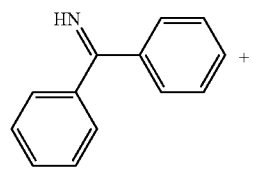
+

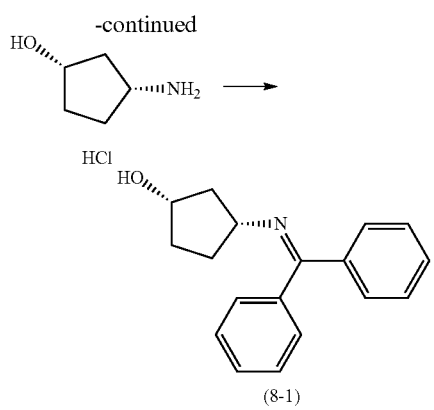

-continued

To a solution of benzophenone imine (366 µl, 2.180 mmol) in CH$_2$Cl$_2$ (2180 µl) was added triethylamine (395 µl, 2.83 mmol) and (1S,3R)-3-aminocyclopentan-1-ol hydrochloride (300 mg, 2.180 mmol). The mixture was stirred at rt for 24 h, diluted with DCM, and washed with water. The organic layer was dried over Na$_2$SO$_4$, and concentrated in vacuo. Purification of the residue on slica gel with 0-40% EtOAc/hexane provided compound (8-1) (463 mg, 1.745 mmol, 80% yield). $^1$H NMR (400 MHz, Chloroform-d) δ 7.61-7.45 (m, 5H), 7.45-7.32 (m, 3H), 7.25-7.17 (m, 2H), 4.63 (s, 1H), 4.41 (s, 1H), 4.09-3.97 (m, 1H), 2.18-2.09 (m, 1H), 2.03-1.69 (m, 5H). [M+H]$^+$ m/z 266.15.

Step 8-2.

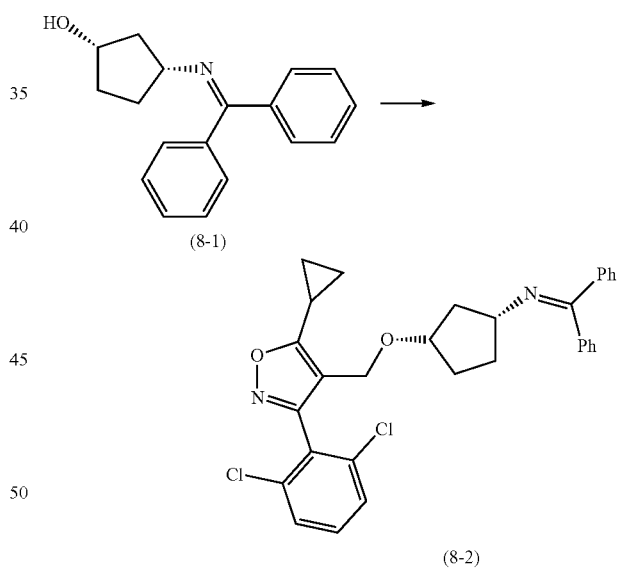

Compound (8-1) (230 mg, 0.867 mmol) was dissolved in THF (5.8 mL). At 0° C. 18-crown-6 (252 mg, 0.953 mmol) and potassium tert-butoxide (117 mg, 1.040 mmol) was added. The mixture was stirred at 0° C. for 5 min and a solution of 4-(chloromethyl)-5-cyclopropyl-3-(2,6-dichlorophenyl)isoxazole (262 mg, 0.867 mmol) in THF (1 mL) was added dropwise. The reaction was stirred at 0° C. for 30 min, warmed to rt, and stirred for 30 min. The reaction was quenched with sat. NH$_4$Cl and extracted with MTBE. The organic layer was dried over Na$_2$SO$_4$ and concentrated in vacuo. Purification of the residue on silica with 0-50% EtOAc/hexane provided compound (8-2) (285 mg, 0.536 mmol, 61.9% yield). [M+H]$^+$ m/z 531.16.

Step 8-3.

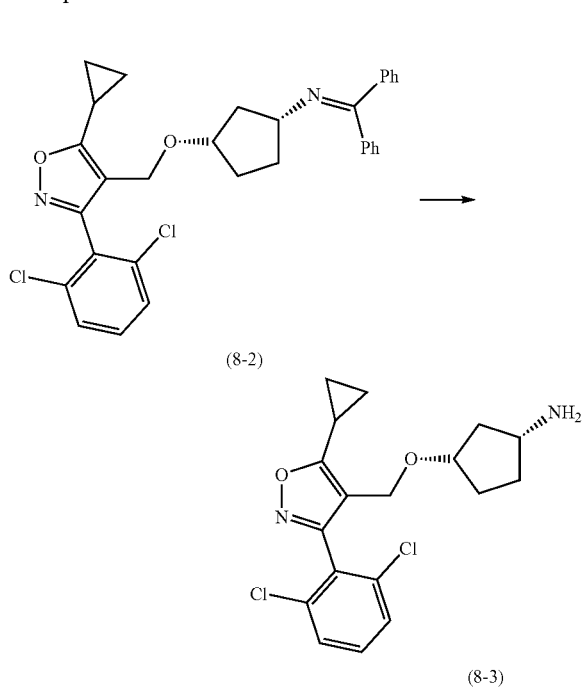

(8-2)

(8-3)

Compound (8-2) (109 mg, 0.205 mmol) was dissolved in THF (684 μl) and 37% aq. hydrochloric acid (33.7 μl, 0.410 mmol) was added. The mixture was stirred at rt for 16 h, quenched with sat. NaHCO$_3$, and extracted with EtOAc (2×). The organic layer was loaded on a 2.5 g of silica plug, and eluted with 0-20% MeOH/DCM. The desired fractions were combined and concentrated to provide compound (8-3) (60 mg, 0.163 mmol, 80% yield) as an oil. $^1$H NMR (400 MHz, Chloroform-d) δ 7.50-7.32 (m, 3H), 4.26 (s, 2H), 3.85 (tt, J=6.0, 3.2 Hz, 1H), 3.32 (p, J=6.1 Hz, 1H), 2.16 (tt, J=8.3, 5.0 Hz, 1H), 2.02-1.77 (m, 2H), 1.77-1.52 (m, 2H), 1.43 (dt, J=13.1, 3.8 Hz, 2H), 1.28 (q, J=2.9, 2.5 Hz, 2H), 1.21-1.05 (m, 2H). [M+H]$^+$ m/z 367.10.

Step 8-4.

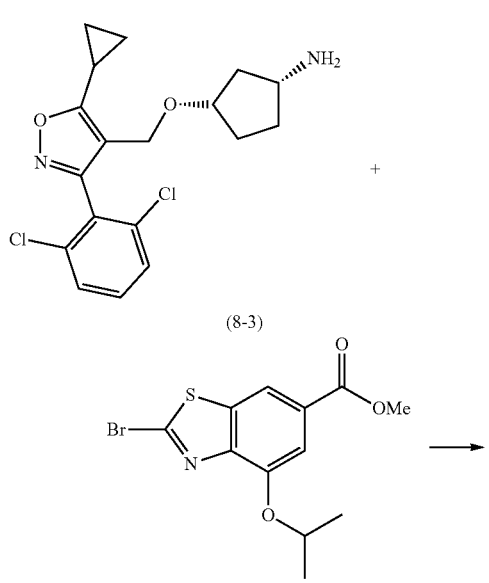

(8-3)

+

-continued

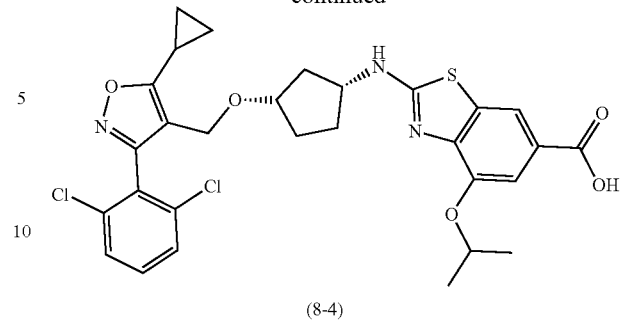

(8-4)

Compound (8-3) (73 mg, 0.181 mmol) was dissolved in DMA (904 μl). Methyl 2-bromo-4-isopropoxybenzo[d]thiazole-6-carboxylate (59.7 mg, 0.181 mmol) and cesium carbonate (236 mg, 0.723 mmol) was added. The mixture was stirred at rt for 17 h, quenched with water, and extracted with MTBE (2×). The combined organic layer was dried over Na$_2$SO$_4$ and concentrated in vacuo. Purification of the residue on silica gel with 0-50% EtOAc/hexane provided compound (8-4) (21 mg, 0.034 mmol, 18.84% yield). [M+H]$^+$ m/z 616.15.

Step 8-5.

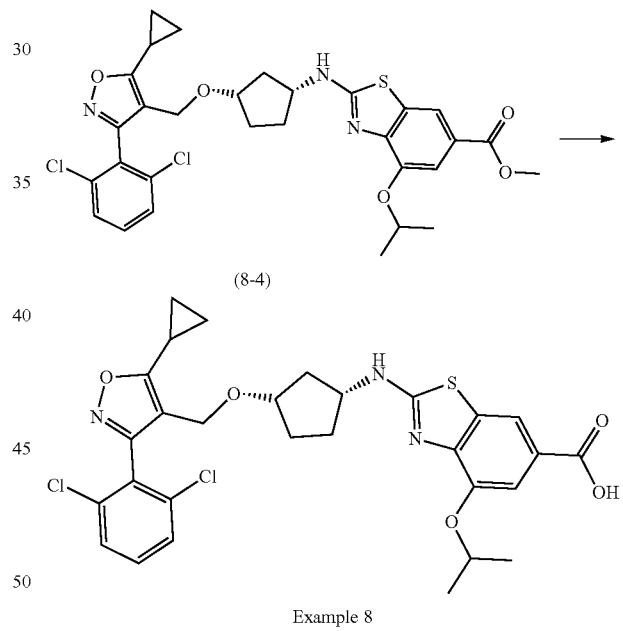

(8-4)

Example 8

Compound (8-4) (21 mg, 0.034 mmol) was dissolved in THF (227 μl), MeOH (227 μl), water (227 μl). A 10 M aq. solution of sodium hydroxide (68.1 μl, 0.681 mmol) was added. The mixture was stirred at 50° C. for 35 min, quenched with 1 M HCl (0.68 mL), and extracted with EtOAc. Purification of the organic layer on silica gel with 0-10% MeOH/DCM provided Example 8 (15 mg, 0.025 mmol, 73.1% yield). $^1$H NMR (400 MHz, Chloroform-d) δ 8.01 (d, J=1.4 Hz, 1H), 7.60 (d, J=1.5 Hz, 1H), 7.47-7.40 (m, 2H), 7.38-7.30 (m, 1H), 4.84 (hept, J=6.1 Hz, 1H), 4.31 (s, 2H), 4.02-3.78 (m, 2H), 2.27-2.16 (m, 1H), 2.12-1.99 (m, 2H), 1.89-1.62 (m, 4H), 1.50 (d, J=6.0 Hz, 6H), 1.37-1.23 (m, 2H), 1.16 (ddd, J=8.6, 4.8, 2.0 Hz, 2H). [M+H]$^+$ m/z 602.13.

Example 9

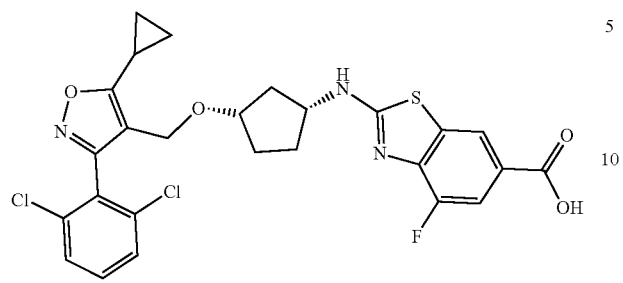

Example 9 was prepared using same protocol shown in example 8. ¹H NMR (400 MHz, Methanol-d4) δ 8.10 (d, J=1.5 Hz, 1H), 7.66 (dd, J=11.5, 1.5 Hz, 1H), 7.52 (ddd, J=8.3, 6.7, 1.3 Hz, 2H), 7.49-7.37 (m, 1H), 4.61 (s, 1H), 4.31 (s, 2H), 4.28-4.14 (m, 1H), 3.98-3.82 (m, 1H), 2.36-2.19 (m, 2H), 2.16-1.99 (m, 1H), 1.82-1.60 (m, 3H), 1.55 (dt, J=14.0, 4.8 Hz, 1H), 1.19 (d, J=6.4 Hz, 4H). [M+H]⁺ m/z 562.08.

Example 10

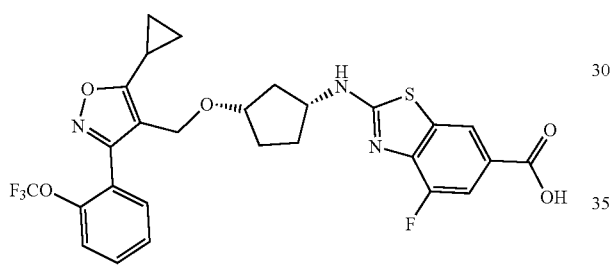

Step 10-1.

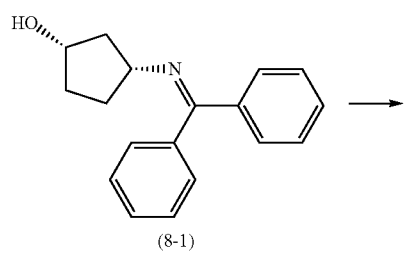

(8-1)

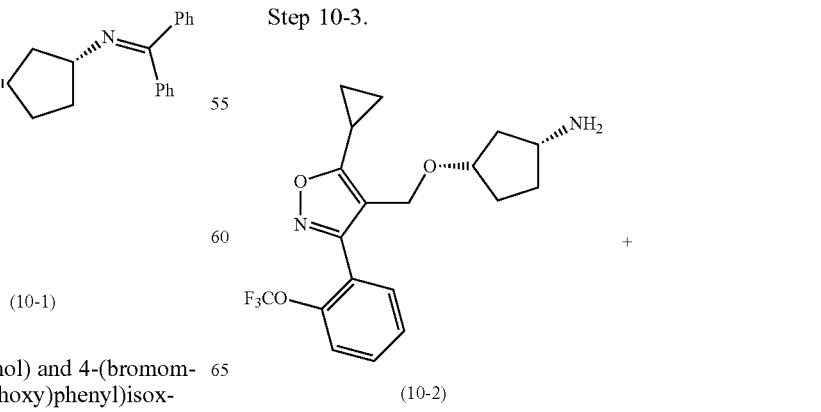

(10-1)

Compound (8-1) (218 mg, 0.822 mmol) and 4-(bromomethyl)-5-cyclopropyl-3-(2-(trifluoromethoxy)phenyl)isoxazole (350 mg, 0.966 mmol) was dissolved in DMSO (3 mL). Sodium tert-butoxide (87 mg, 0.904 mmol) was added and the mixture was stirred at rt for 2 h 30 min. The reaction was quenched with water and extracted with MTBE (3×). The combined organic layer was dried over Na₂SO₄ and concentrated in vacuo. Purification of the residue on silica gel with 0-30% EtOAc/hexane provided compound (10-1) (287 mg, 0.525 mmol, 63.9% yield). [M+H]⁺ m/z 547.22.

Step 10-2.

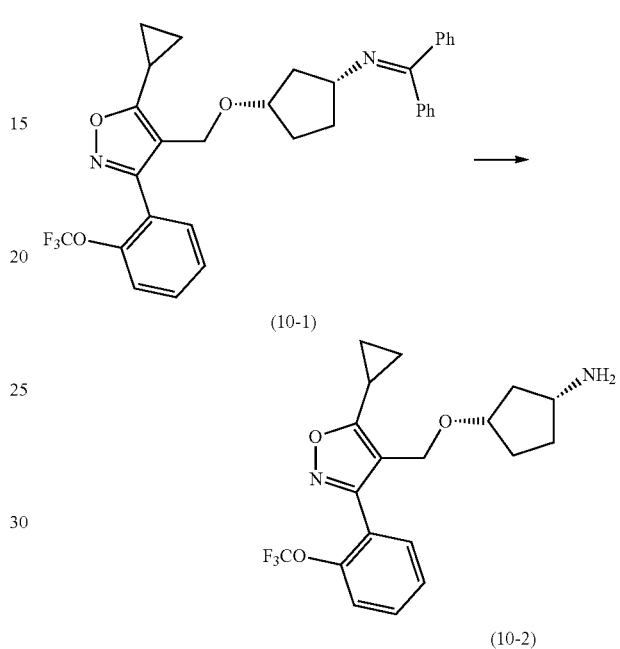

(10-1)

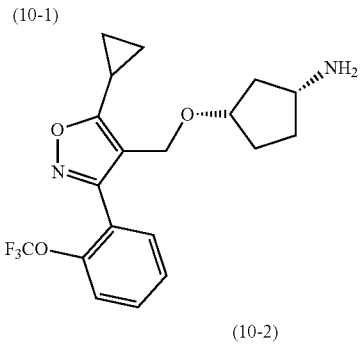

(10-2)

Compound (10-1) (287 mg, 0.525 mmol) was dissolved in THF (1750 μl) and 37% aq. hydrochloric acid (86 μl, 1.050 mmol) was added. The mixture was stirred at rt for 16 h, quenched with sat. NaHCO₃, and extracted with EtOAc (2×). The combined organic layer was dried over Na₂SO₄ and concentrated in vacuo. Purification of the residue on silica gel with 0-20% MeOH/DCM provided compound (10-2) (164 mg, 0.429 mmol, 82% yield). ¹H NMR (400 MHz, Chloroform-d) δ 7.60-7.55 (m, 1H), 7.53 (dt, J=8.1, 1.6 Hz, 1H), 7.41 (tq, J=7.6, 1.5 Hz, 2H), 4.40-4.23 (m, 2H), 3.87 (tt, J=6.3, 3.4 Hz, 1H), 3.30 (p, J=6.1 Hz, 1H), 2.21-2.06 (m, 1H), 2.05-1.81 (m, 2H), 1.80-1.57 (m, 2H), 1.44 (dd, J=13.3, 5.6 Hz, 2H), 1.34-1.18 (m, 2H), 1.13 (tdd, J=7.5, 4.3, 2.3 Hz, 2H). [M+H]⁺ m/z 383.17.

Step 10-3.

+

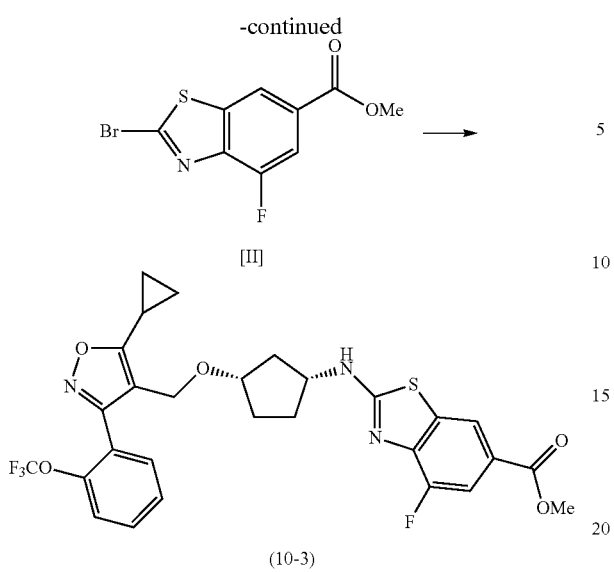

(10-3)

Compound (10-2) (85 mg, 0.222 mmol) was dissolved in DMA (1.1 mL) and methyl 2-bromo-4-fluorobenzo[d]thiazole-6-carboxylate (64.5 mg, 0.222 mmol) and cesium carbonate (72.4 mg, 0.222 mmol) was added. The mixture was stirred at rt for 16 h, quenched with water, and extracted with MTBE (2×). The combined organic layer was dried over $Na_2SO_4$ and concentrated in vacuo. Purification of the residue on silica gel with 0-30% EtOAc/hexane provided compound (10-3) (98 mg, 0.166 mmol, 74.5% yield). $^1$H NMR (400 MHz, Chloroform-d) δ 8.10 (d, J=1.5 Hz, 1H), 7.73 (dd, J=11.2, 1.5 Hz, 1H), 7.59 (dd, J=7.6, 1.8 Hz, 1H), 7.52 (ddd, J=8.4, 7.4, 1.8 Hz, 1H), 7.45-7.32 (m, 2H), 6.15 (s, 1H), 4.46-4.29 (m, 2H), 4.21 (s, 1H), 3.98 (ddt, J=5.0, 3.7, 1.8 Hz, 1H), 3.94 (s, 3H), 2.14 (tt, J=8.4, 5.0 Hz, 1H), 1.96 (ddd, J=14.3, 7.1, 5.3 Hz, 1H), 1.87-1.66 (m, 5H), 1.34-1.21 (m, 2H), 1.22-1.12 (m, 2H). [M+H]$^+$ m/z 592.15.

Step 10-4.

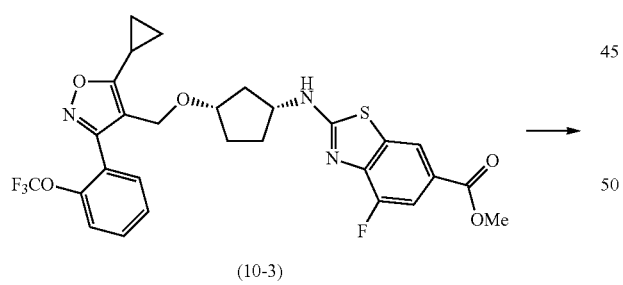

(10-3)

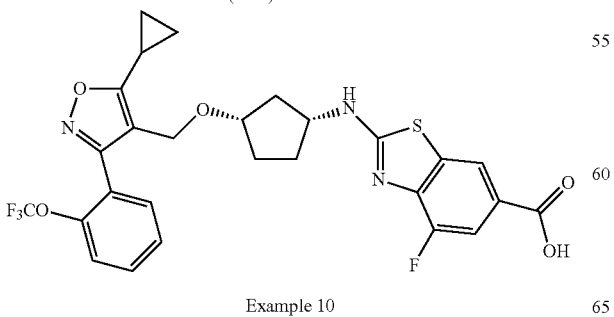

Example 10

Compound (10-3) (98 mg, 0.166 mmol) was dissolved in THF (1104 μl), MeOH (1104 μl) and Water (1104 μl). A 10 M aq. solution of sodium hydroxide (331 μl, 3.31 mmol) was added. The mixture was stirred at 50° C. for 2 h 30 min, cooled to rt, quenched with 1 M HCl (3.3 mL), and extracted with EtOAc. Purification of the organic layer on silica gel with 0-80% acetone/hexane provided Example 10 (69 mg, 0.119 mmol, 72.1% yield).

1H NMR (400 MHz, Methanol-d4) δ 8.10 (d, J=1.5 Hz, 1H), 7.78-7.54 (m, 3H), 7.45 (q, J=7.7 Hz, 2H), 4.37 (s, 2H), 4.30-4.12 (m, 1H), 3.96 (t, J=5.1 Hz, 1H), 2.28 (h, J=6.9 Hz, 2H), 2.08 (dt, J=12.9, 6.7 Hz, 1H), 1.76 (dt, J=10.8, 5.3 Hz, 2H), 1.72-1.53 (m, 2H), 1.17 (d, J=7.0 Hz, 4H). [M+H]$^+$ m/z 578.13.

Example 11

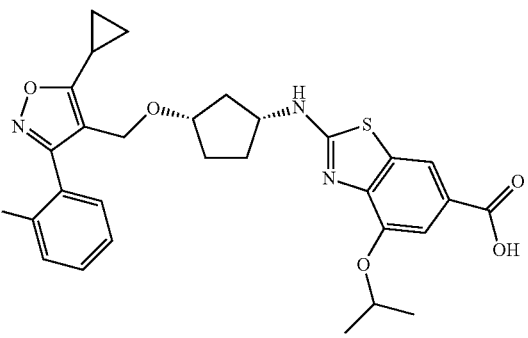

Example 11 was prepared using same protocol as shown in Example 10. $^1$H NMR (400 MHz, Methanol-d4) δ 7.93 (d, J=1.5 Hz, 1H), 7.59 (ddd, J=15.2, 7.5, 1.8 Hz, 2H), 7.52 (d, J=1.5 Hz, 1H), 7.50-7.39 (m, 2H), 4.37 (s, 2H), 4.21 (t, J=6.7 Hz, 1H), 3.96 (dt, J=8.5, 4.3 Hz, 1H), 2.34-2.21 (m, 2H), 2.07 (dq, J=12.9, 6.5 Hz, 1H), 1.76 (td, J=7.4, 6.4, 4.8 Hz, 2H), 1.72-1.55 (m, 2H), 1.41 (d, J=6.1 Hz, 6H), 1.23-1.10 (m, 4H). [M+H]$^+$ m/z 618.18.

Example 12

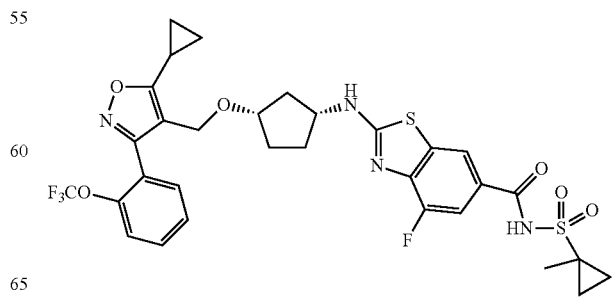

Step 12-1

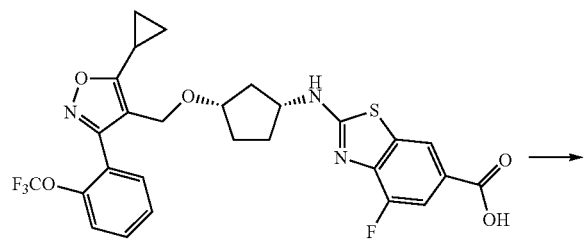

Example 10

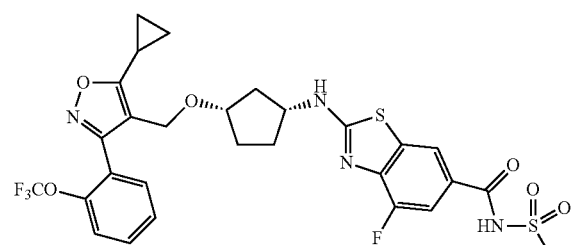

Example 12

Step 13-1

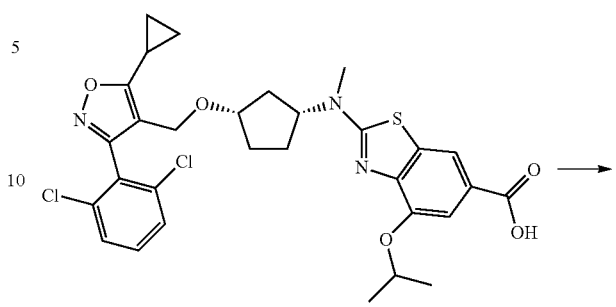

Example 1

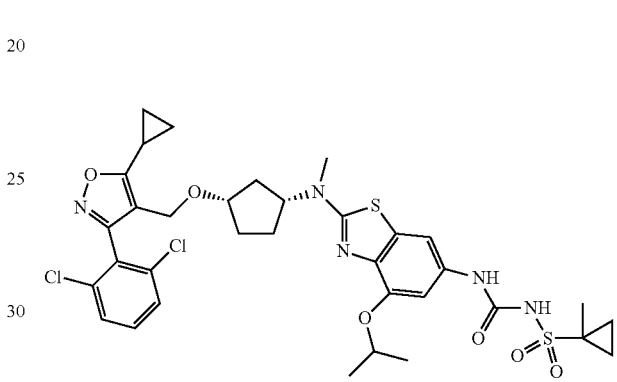

Example 13

Example 10 (50 mg, 0.087 mmol) is dissolved in CH$_2$Cl$_2$ (0.6 ml). DMAP (10.58 mg, 0.087 mmol), 1-methyl cyclopropane-1-sulfonamide (11.70 mg, 0.087 mmol), and EDC (16.60 mg, 0.087 mmol) are added. The resulting mixture is stirred at rt for 14 h, quenched with water, and extracted with DCM (2×). The combined organic layer is dried over Na$_2$SO$_4$ and concentrated in vacuo. Purification of the residue on silica gel with 0-50% acetone/hexane provides Example 12.

Example 13

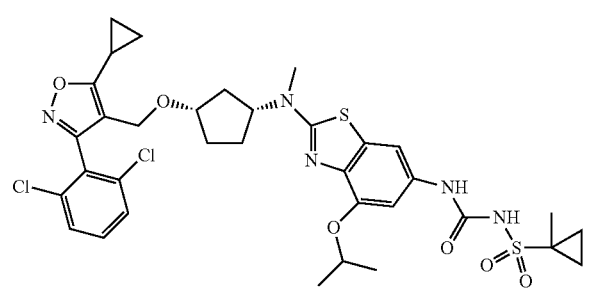 [SMILES: CC(C)Oc1cc(NC(=O)NS(=O)(=O)C2(C)CC2)cc2sc(N(C)[C@@H]3CC[C@H](OCc4c(-c5c(Cl)cccc5Cl)noc4C4CC4)C3)nc12]

To a solution of Example 1 (50 mg, 0.081 mmol) in toluene (1.0 ml) is added triethylamine (13 μl, 0.096 mmol) and diphenylphosphoryl azide (19 μl, 0.087 mmol) dropwise. The mixture is stirred at 23° C. for 1 h, at 85° C. for 3.5 h, and cooled to 23° C. A solution of 1-methylcyclopropane-1-sulfonamide (22 mg, 0.162 mmol) and DBU (24 μl, 0.162 mmol) in THF (0.5 mL) is added. The mixture is stirred at 23° C. for 14 h, quenched with 1 M HCl, and extracted with EtOAc (2×). The combined organic layer is dried over Na$_2$SO$_4$, and concentrated in vacuo. Purification of the residue on silica gel column with 0-50% acetone provides Example 13.

Example 14

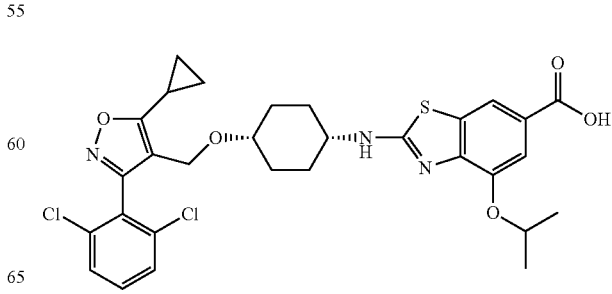

Step 14-1

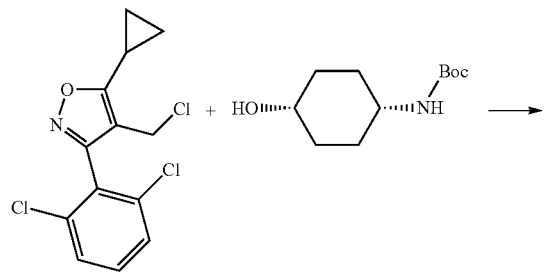

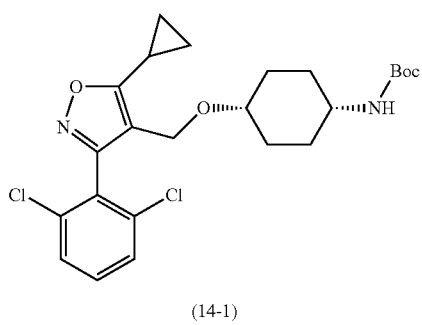

(14-1)

To a solution of tert-butyl ((1s,4s)-4-hydroxycyclohexyl) carbamate (800 mg, 3.72 mmol), 4-(chloromethyl)-5-cyclopropyl-3-(2,6-dichlorophenyl)isoxazole (1126 mg, 3.72 mmol) and 18-crown-6 (1375 mg, 5.20 mmol) in THF (7 ml) at 0° C. under N₂ was added slowly potassium tert-butoxide (584 mg, 5.20 mmol) (5.2 ml of 1.0 M THF solution). The mixture was stirred at 0° C. for 10 min and at RT for 1 h under N₂ (brown). The solvent was removed in vacuo and the residue was diluted with brine and extracted with EtOAc. The combined organic layers were concentrated and the residue was purified by CombiFlash on silica gel eluting with 0 to 35% EtOAc/hexane to give tert-butyl ((1s,4s)-4-((5-cyclopropyl-3-(2,6-dichlorophenyl)isoxazol-4-yl)methoxy)cyclohexyl)carbamate (compound 14-1) as pale yellow oil (1.3 g, 2.70 mmol).

Step 14-2.

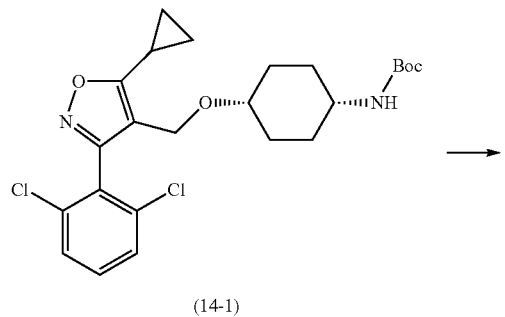

(14-1)

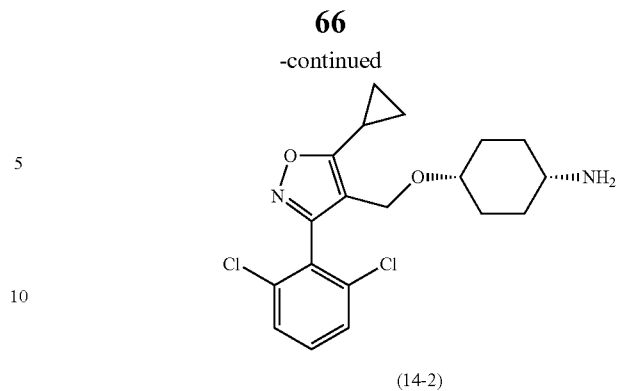

(14-2)

(tert-Butyl ((1s,4s)-4-((5-cyclopropyl-3-(2,6-dichlorophenyl)isoxazol-4-yl)methoxy)cyclohexyl) carbamate (compound 14-1) (1.3 g, 2.70 mmol) was dissolved in DCM (4 ml) and treated with TFA (1.248 ml, 16.20 mmol). The reaction mixture was stirred at rt for 2 h and quenched slowly with sat. NaHCO₃. The mixture was extracted with EtOAc and the organic layer was washed with brine and concentrated. The residue was purified by CombiFlash on silica gel eluting with 0 to 15% MeOH/DCM to give (1s,4s)-4-((5-cyclopropyl-3-(2,6-dichlorophenyl)isoxazol-4-yl)methoxy)cyclohexan-1-amine (compound 14-2) (0.7 g, 68%) as a white foam. ¹H NMR (500 MHz, Methanol-d4) δ 7.63-7.42 (m, 3H), 4.33 (s, 2H), 3.46 (p, J=3.0 Hz, 1H), 3.05 (tt, J=11.3, 4.1 Hz, 1H), 2.29 (tt, J=7.2, 6.3 Hz, 1H), 1.89-1.76 (m, 2H), 1.70 (dq, J=13.0, 3.5 Hz, 2H), 1.61 (qd, J=12.5, 3.6 Hz, 2H), 1.50-1.35 (m, 2H), 1.24-1.13 (m, 4H).). LC/MS observed [M+H], 381.28.

Step 14-3.

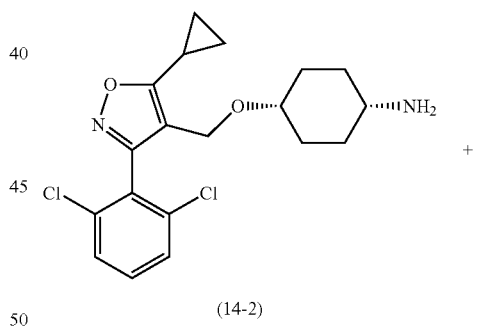

(14-2)

+

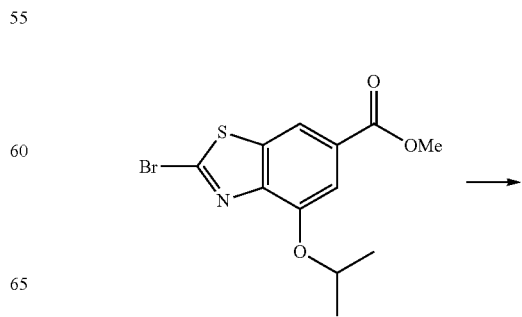

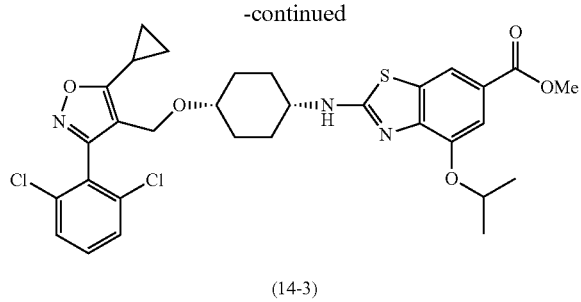

(14-3)

To (1s,4s)-4-((5-cyclopropyl-3-(2,6-dichlorophenyl)isoxazol-4-yl)methoxy)cyclohexan-1-amine (compound 14-2) (33 mg, 0.087 mmol) in acetonitrile (1 ml) and DMA (1.000 ml) was added methyl 2-bromo-4-isopropoxybenzo[d]thiazole-6-carboxylate (34.3 mg, 0.104 mmol) and cesium carbonate (85 mg, 0.260 mmol). The resulting mixture was stirred at 80° C. for 6 h, then rt for 16 h. The mixture was diluted with EtOAc, washed with water, brine, dried, filtered and concentrated. The residue was purified by CombiFlash on silica gel eluting with 0 to 60% EtOAc/hexane to give methyl 2-(((1s,4s)-4-((5-cyclopropyl-3-(2,6-dichlorophenyl) isoxazol-4-yl)methoxy)cyclohexyl)amino)-4-isopropoxybenzo[d]thiazole-6-carboxylate (compound 14-3) (11 mg, 0.017 mmol, 20.16% yield). $^1$H NMR (400 MHz, Chloroform-d) δ 7.85 (d, J=1.5 Hz, 1H), 7.43 (d, J=1.4 Hz, 1H), 7.41-7.23 (m, 3H), 4.74 (hept, J=6.1 Hz, 1H), 4.20 (s, 2H), 3.84 (s, 3H), 3.36 (b, 1H), 3.23 (b, 1H), 2.06 (ddd, J=8.5, 5.1, 3.4 Hz, 1H), 1.73-1.54 (m, 4H), 1.48-1.26 (m, 10H), 1.26-1.13 (m, 2H), 1.13-0.96 (m, 2H). LC/MS observed [M+H], 630.16.

Step 14-4.

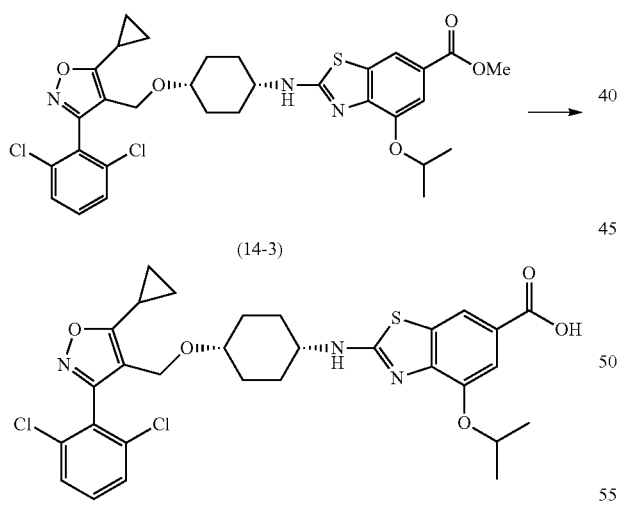

Example 14

To methyl 2-(((1s,4s)-4-((5-cyclopropyl-3-(2,6-dichlorophenyl)isoxazol-4-yl)methoxy)cyclohexyl)amino)-4-isopropoxybenzo[d]thiazole-6-carboxylate (compound 14-3) (11 mg, 0.017 mmol) in MeOH (0.8 ml) and THF (0.8 ml) was added LiOH (0.052 ml, 0.052 mmol) and the mixture was stirred at rt for 4 h. Another portion of LiOH (0.052 ml, 0.052 mmol) was added and the mixture was stirred at RT for 16 h. The mixture was acidified with 1N HCl and concentrated. The residue was purified by HPLC eluting with 0.1% TFA in ACN/water to give 2-(((1s,4s)-4-((5-cyclopropyl-3-(2,6-dichlorophenyl)isoxazol-4-yl)methoxy) cyclohexyl)amino)-4-isopropoxybenzo[d]thiazole-6-carboxylic acid (Example 14) (9.5 mg, 0.015 mmol, 88% yield). $^1$H NMR (400 MHz, Chloroform-d) δ 11.92 (s, 1H), 7.84 (d, J=1.2 Hz, 1H), 7.54 (d, J=1.3 Hz, 1H), 7.46-7.23 (m, 3H), 4.68 (hept, J=6.1 Hz, 1H), 4.19 (s, 2H), 3.37 (q, J=3.4 Hz, 1H), 3.05 (s, 1H), 2.25-2.00 (m, 2H), 1.90-1.58 (m, 6H), 1.38 (d, J=6.0 Hz, 6H), 1.18 (d, J=6.2 Hz, 3H), 1.07 (dt, J=8.7, 3.4 Hz, 2H). LC/MS observed [M+H], 616.14.

Example 15

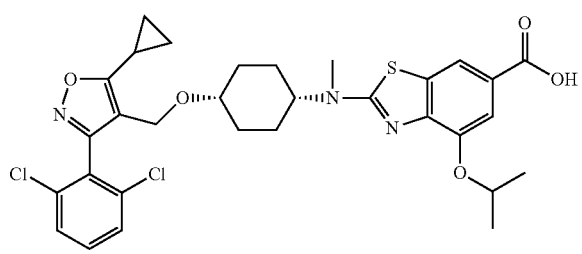 [SMILES: CC(C)Oc1cc(C(=O)O)cc2sc(N(C)[C@H]3CC[C@@H](OCc4c(-c5c(Cl)cccc5Cl)noc4C4CC4)CC3)nc12]

Step 15-1.

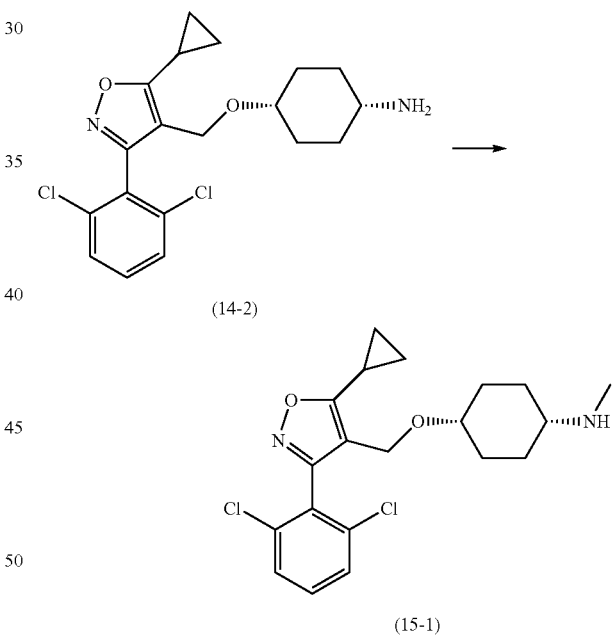

(15-1)

To (1s,4s)-4-((5-cyclopropyl-3-(2,6-dichlorophenyl)isoxazol-4-yl)methoxy)cyclohexan-1-amine (compound 14-2) (50 mg, 0.131 mmol) and paraformaldehyde (4.3 mg, 0.144 mmol) was added trifluoroethanol (2 ml) and the mixture was stirred at 45° C. for 16 h. The mixture was concentrated and then dissolved in trifluoroethanol (2 ml) and sodium borohydride (9.9 mg, 0.262 mmol) was added. The mixture was stirred at 45° C. for 1 h and then quenched with water, then concentrated, chased with ACN to give (1s,4s)-4-((5-cyclopropyl-3-(2,6-dichlorophenyl)isoxazol-4-yl) methoxy)-N-methylcyclohexan-1-amine as crude product. LC/MS observed [M+H], 395.14. This material was used directly to next step.

Step 15-2.

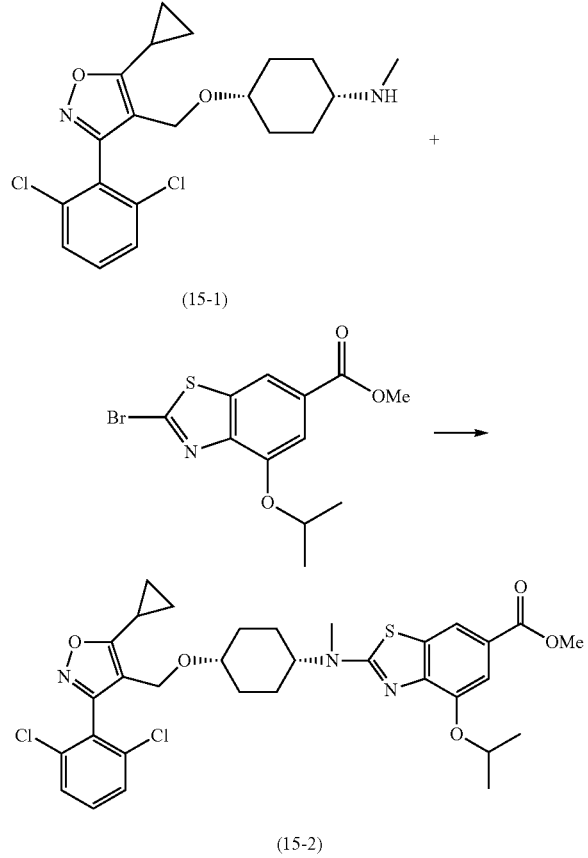

(15-1)

(15-2)

To crude (1s,4s)-4-((5-cyclopropyl-3-(2,6-dichlorophenyl)isoxazol-4-yl)methoxy)-N-methylcyclohexan-1-amine (compound 15-1) (51.8 mg, 0.131 mmol) and methyl 2-bromo-4-isopropoxybenzo[d]thiazole-6-carboxylate (51.9 mg, 0.157 mmol) in acetonitrile (1 ml) and DMA (1 ml) was added cesium carbonate (128 mg, 0.393 mmol). The resulting mixture was stirred at 80° C. for 16 h. The mixture was diluted with EtOAc, washed with water, brine, dried, filtered and concentrated. The residue was purified by CombiFlash on silica gel eluting with 0 to 60% EtOAc/hexane to give methyl 2-(((1s,4s)-4-((5-cyclopropyl-3-(2,6-dichlorophenyl)isoxazol-4-yl)methoxy)cyclohexyl)(methyl)amino)-4-isopropoxybenzo [d]thiazole-6-carboxylate (compound 15-2) (6.2 mg). LC/MS observed [M+H], 644.17.

Step 15-3.

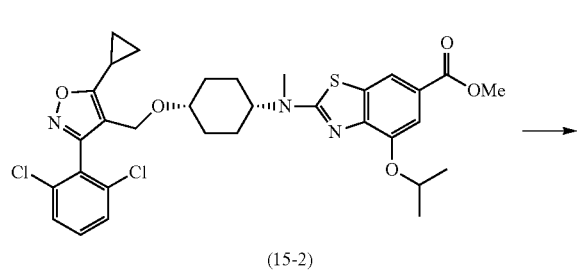

(15-2)

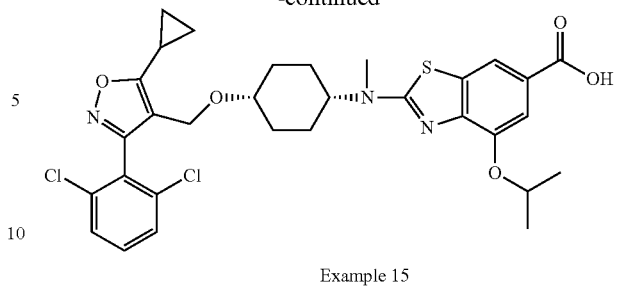

Example 15

To methyl 2-(((1s,4s)-4-((5-cyclopropyl-3-(2,6-dichlorophenyl)isoxazol-4-yl)methoxy) cyclohexyl)(methyl)amino)-4-isopropoxybenzo[d]thiazole-6-carboxylate (compound 15-2) (6.2 mg, 9.62 µmol) in MeOH (0.8 ml) and THF (0.8 ml) was added NaOH (1 N) (0.038 ml, 0.038 mmol). The mixture was stirred at RT for 16 h. The mixture was acidified with 1N HCl, and the concentrated. The residue was purified by prep. HPLC eluting with 0.1% TFA in ACN/water to give 2-(((1s,4s)-4-((5-cyclopropyl-3-(2,6-dichlorophenyl)isoxazol-4-yl)methoxy) cyclohexyl)(methyl)amino)-4-isopropoxybenzo[d]thiazole-6-carboxylic acid (Example 15). 1H NMR (500 MHz, Chloroform-d) δ 12.04 (s, 1H), 7.77 (d, J=1.3 Hz, 1H), 7.49 (d, J=1.3 Hz, 1H), 7.35 (d, J=8.0 Hz, 2H), 7.26 (dd, J=8.8, 7.4 Hz, 1H), 4.67 (p, J=6.1 Hz, 1H), 4.18 (s, 2H), 3.85 (s, 3H), 3.37 (t, J=3.8 Hz, 1H), 3.18-2.83 (m, 1H), 2.09 (tt, J=8.4, 5.1 Hz, 1H), 1.86-1.57 (m, 6H), 1.41-1.27 (m, 8H), 1.18 (dt, J=6.6, 4.5 Hz, 3H), 1.07 (dt, J=8.6, 3.4 Hz, 2H). LC/MS observed [M+H], 630.16.

Example 16

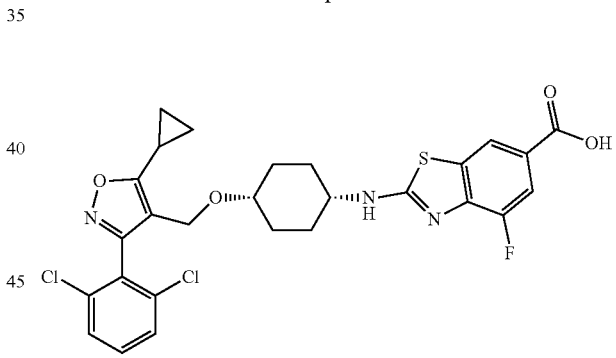

Example 16 was prepared using same protocol as shown in Example 14. [M+H], 576.09

Example 17

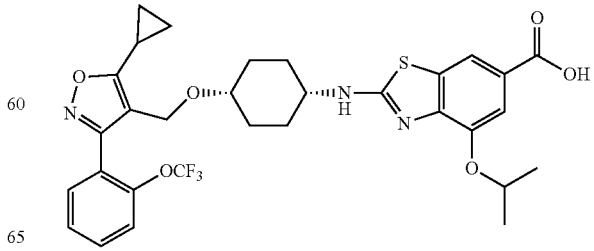

Example 17 was prepared using same protocol as shown in Example 14. ¹H NMR (400 MHz, Chloroform-d) δ 7.91 (s, 1H), 7.58-7.50 (m, 2H), 7.41 (td, J=7.8, 1.8 Hz, 1H), 7.32 (ddd, J=9.6, 7.8, 3.9 Hz, 2H), 4.71 (p, J=6.1, 5.6 Hz, 1H), 4.26 (s, 2H), 3.39 (s, 1H), 3.19 (s, 1H), 2.08 (tt, J=8.4, 5.1 Hz, 1H), 1.71 (d, J=13.4 Hz, 4H), 1.57 (d, J=10.5 Hz, 1H), 1.42 (d, J=6.0 Hz, 7H), 1.16 (td, J=4.9, 2.3 Hz, 2H), 1.04 (dt, J=8.6, 3.4 Hz, 2H). [M+H], 632.20

Example 18

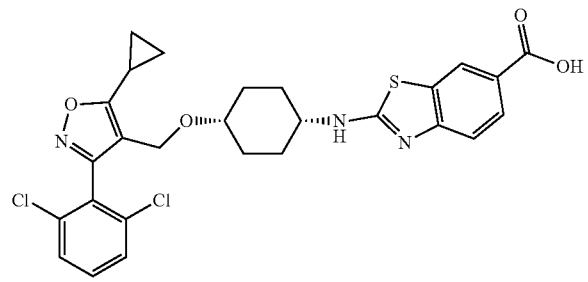 [SMILES: O=C(O)c1ccc2nc(N[C@H]3CC[C@@H](OCc4c(-c5c(Cl)cccc5Cl)noc4C4CC4)CC3)sc2c1]

Example 18 was prepared using same protocol as shown in Example 14. [M+H], 558.09

Example 19

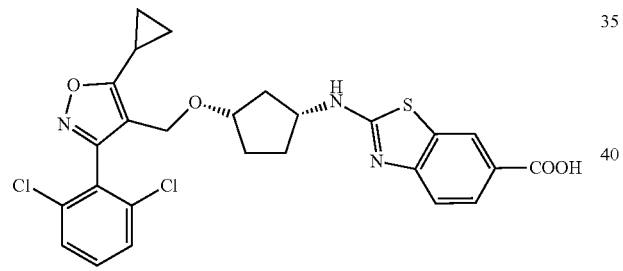

Step 19-1

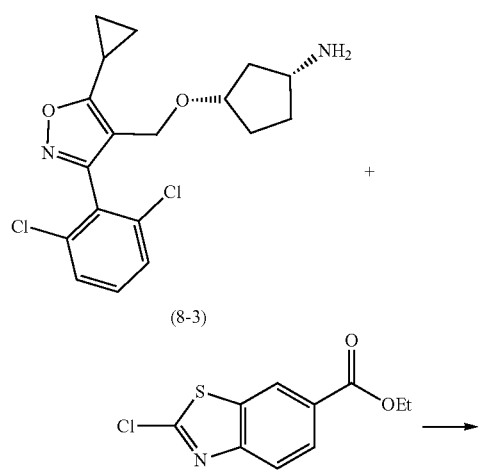

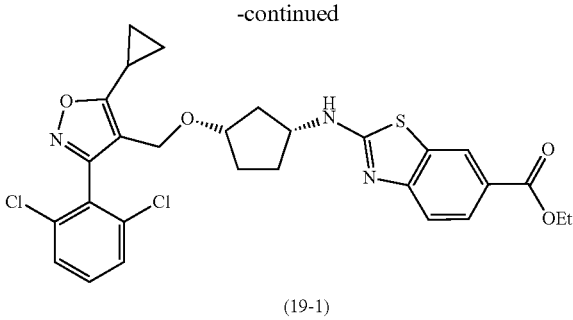

(19-1)

Compound (8-3) (129 mg, 0.351 mmol) was dissolved in DMA (1.5 ml). Ethyl 2-chlorobenzo[d]thiazole-6-carboxylate (170 mg, 0.702 mmol) and Hunig's base (0.123 ml, 0.702 mmol) was added. The mixture was heated in microwave at 170° C. for 20 min. The reaction was quenched with water and extracted with MTBE (2×). The combined organic layer was dried over Na₂SO₄ and concentrated in vacuo. Purification of the residue on silica gel with 0-50% EtOAc/hexane provided (19-1) (111 mg, 0.194 mmol, 55.2% yield). [M+H], 572.12

Step 19-2

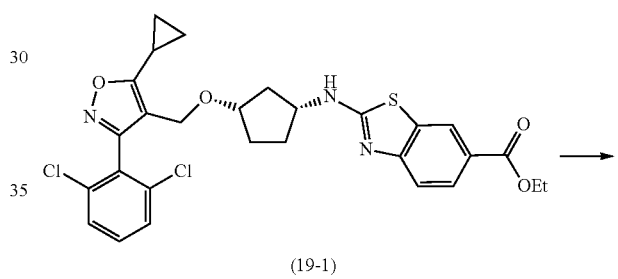

(19-1)

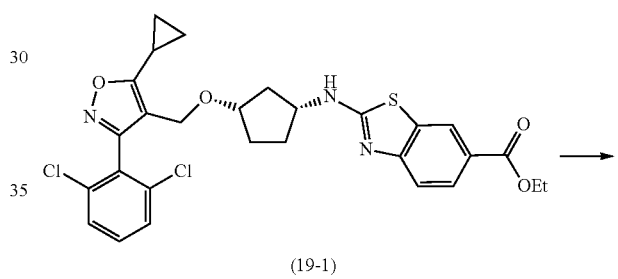

Example 19

Compound (19-1) (42 mg, 0.073 mmol) was dissolved in MeOH (489 μl), THF (489 μl), and water (489 μl). An aq. 10 M sodium hydroxide solution (147 μl, 1.467 mmol) was added. The mixture was stirred at 50° C. for 2 h, quenched with 1.5 mL of 1 M HCl, and extracted with EtOAc. The organic layer was purified on silica gel with 0-50% acetone/hexane to give Example 19 (28 mg, 0.051 mmol, 70.1% yield). [M+H], 572.12

Example 20

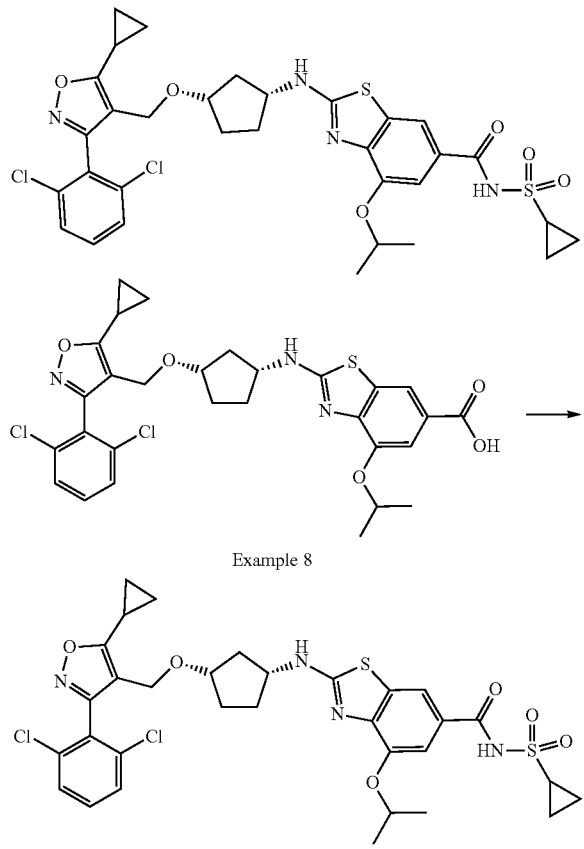

Example 8

Example 20

Example 8 (169 mg, 0.28 mmol) was dissolved in CH$_2$Cl$_2$ (1.9 ml). DMAP (68.6 mg, 0.56 mmol), cyclopropanesulfonamide (68 mg, 0.56 mmol), and EDC (108 mg, 0.56 mmol) are added. The resulting mixture is stirred at rt for 3 h, quenched with brine, and extracted with DCM. The organic layer was dried over Na$_2$SO$_4$ and concentrated in vacuo. Purification of the residue on silica gel with 0-5% MeOH/DCM provided Example 20 (125 mg, 0.18 mmol, 63% yield). 1H NMR (400 MHz, DMSO-d6) δ 11.79 (s, 1H), 8.25 (s, 1H), 7.85 (d, J=1.6 Hz, 1H), 7.61-7.51 (m, 2H), 7.51-7.42 (m, 1H), 7.34 (d, J=1.6 Hz, 1H), 4.77 (p, J=6.1 Hz, 1H), 4.24-4.03 (m, 2H), 3.90 (s, 1H), 3.70 (d, J=4.5 Hz, 1H), 3.01 (s, 1H), 2.39-2.22 (m, 1H), 2.17 (dt, J=14.0, 7.1 Hz, 1H), 1.93-1.75 (m, 1H), 1.66-1.40 (m, 3H), 1.29 (dt, J=12.6, 6.2 Hz, 1H), 1.22 (d, J=6.0 Hz, 6H), 1.13-0.81 (m, 8H). [M+H]$^+$ m/z 705.13.

Assays

Human FXR (NR1H4) Assay

Determination of a ligand mediated Gal4 promoter driven transactivati on to quantify ligand binding mediated activation of FXR. FXR Reporter Assay kit purchased from Indigo Biosciences (Catalogue number: IB00601) to determine the potency and efficacy of compound developed by Enanta that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. EC$_{50}$ and efficacy (normalize to CDCA set as 100%) is determined by XLFit. The assay is according to the manufacturer's instructions. In brief, the assay was performed in white, 96 well plates using final volume of 100 ul containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 μl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room temperature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 μl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. EC$_{50}$ and Efficacy (normalize to CDCA set as 100%) is determined by XLFit.

To assess the FXR agonistic potency of the example compounds as well as for the reference compound (1), potency ranges were determined in the Human FXR (NR1H4) Assay as listed below in Table 4. The efficacy was normalized to CDCA set as 100%. (A=EC50<0.1 μM; B=0.1 μM<EC50<1.0 μM; C=1.0 μM<EC50<10 μM; D=EC50>10 μM).

TABLE 4

| Example | EC50 (μM) | Efficacy (%) |
|---|---|---|
| 1 | A | 96 |
| 2 | A | 75 |
| 3 | B | 58 |
| 4 | B | 73 |
| 5 | A | 85 |
| 6 | A | 67 |
| 7 | A | 57 |
| 8 | A | 99 |
| 9 | A | 104 |
| 10 | A | 81 |
| 11 | A | 92 |
| 14 | A | 84 |

TABLE 4-continued

| Example | EC50 (μM) | Efficacy (%) |
|---------|-----------|--------------|
| 15 | A | 65 |
| 16 | B | 24 |
| 17 | A | 91 |
| 18 | A | 52 |
| 19 | B | 116 |
| 20 | B | 111. |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula (Ib), or a pharmaceutically acceptable salt thereof:

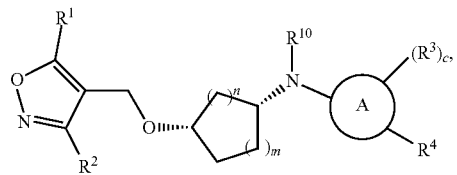

Ib wherein:

$R^1$ is hydrogen, halogen, cyano, optionally substituted —$C_1$-$C_6$ alkyl, optionally substituted —$C_2$-$C_6$ alkenyl, optionally substituted —$C_2$-$C_6$ alkynyl, optionally substituted —$C_3$-$C_6$ cycloalkyl or optionally substituted 3- to 6-membered heterocycloalkyl;

$R^2$ is an optionally substituted aryl, optionally substituted heteroaryl, optionally substituted arylalkyl, optionally substituted heteroarylalkyl, or optionally substituted cycloalkyl;

m is 0, 1 or 2;

n is 1 or 2;

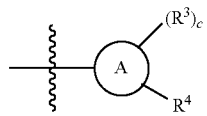

is selected from the groups set forth below:

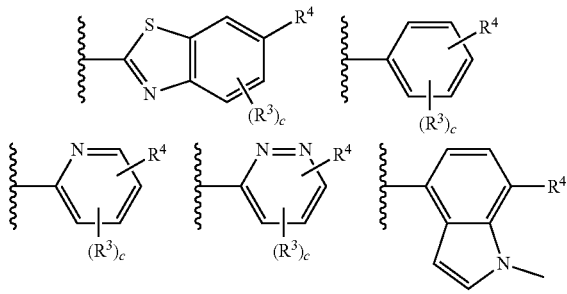

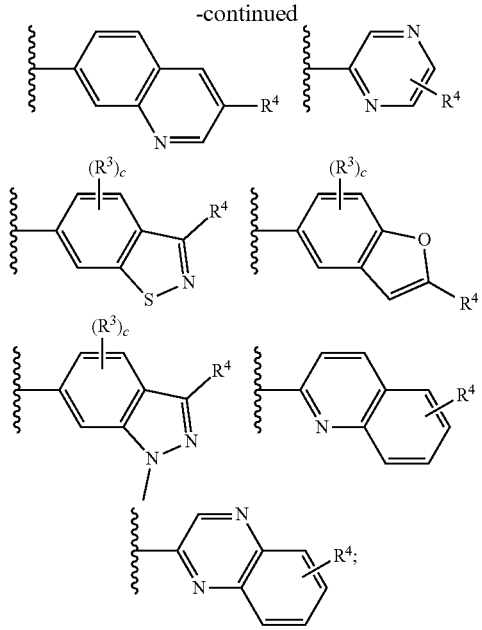

Each $R^3$ is independently selected from the group consisting of halo, hydroxy, —OMe, —$OCH_2F$, $OCF_3$, —$C_2$-$C_6$-alkoxy, —$C_1$-$C_6$-alkyl, —$C_1$-$C_6$ haloalkyl, —$C_2$-$C_6$ alkenyl, —$C_2$-$C_6$ alkynyl, —$C_3$-$C_6$ cycloalkyl, —O—$C_1$-$C_2$ alkylphenyl, cyano, —$CH_2F$, —$CHF_2$, —$CF_3$, —$SCF_3$, —$NH_2$, —NHMe, and —$NMe_2$;

c is 0, 1, or 2;

$R^4$ is

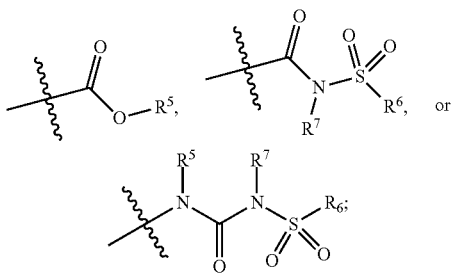

wherein $R^5$ and $R^7$ are independently selected from the group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl; and
5) Optionally substituted —$C_3$-$C_8$ cycloalkyl;

$R^6$ is selected from the group consisting of:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted aryl;
6) Optionally substituted arylalkyl;
7) Optionally substituted heterocycloalkyl;
8) Optionally substituted heteroaryl;
9) Optionally substituted heteroarylalkyl; and 10) NR⁸R⁹; wherein R⁸ and R⁹ are each independently selected from hydrogen, optionally substituted —C₁-C₈ alkyl, optionally substituted —C₂-C₈ alkenyl, optionally substituted vC₂-C₈ alkynyl, optionally substituted —C₃-C₈ cycloalkyl, optionally substituted aryl, optionally substituted arylalkyl, optionally substituted heterocycloalkyl, optionally substituted heteroaryl, optionally substituted heteroarylalkyl, alternatively, R⁸ and R⁹ are taken together with the nitrogen atom to which they are attached to form a heterocyclic ring; and R¹⁰ is hydrogen, optionally substituted —C₁-C₆ alkyl, optionally substituted —C₂-C₆ alkenyl, optionally substituted —C₂-C₆ alkynyl, optionally substituted —C₃-C₆ cycloalkyl, or R¹¹C(O)—, where R¹¹ is hydrogen or C₁-C₄-alkyl.

2. The compound of claim 1, wherein R² is selected from the groups set forth below:

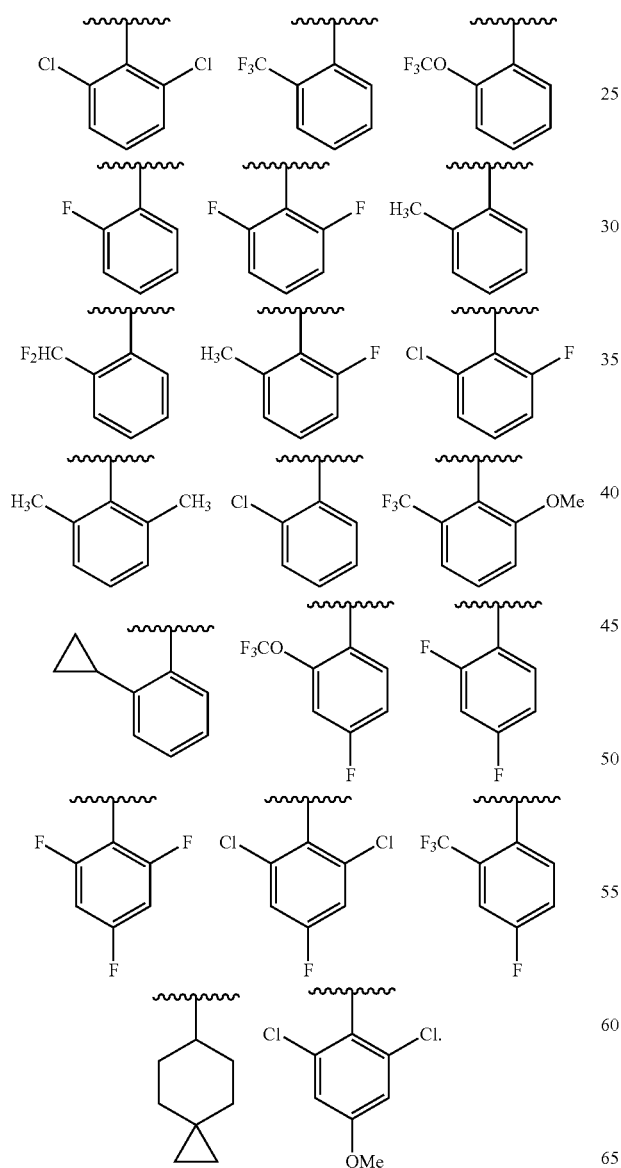

3. The compound of claim 1, wherein R⁴ is

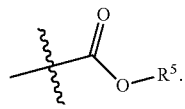

4. The compound of claim 1, wherein R⁴ is

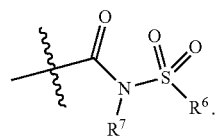

5. The compound of claim 1, wherein R⁴ is

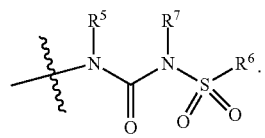

6. The compound of claim 1, wherein R¹ is cyclopropyl.

7. The compound of claim 1, represented by Formula (VIa) or Formula (VIb), or a pharmaceutically acceptable salt thereof,

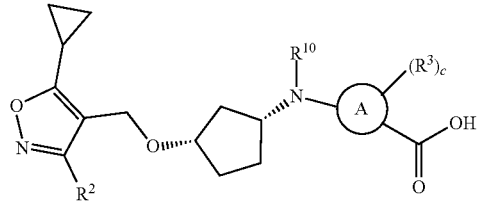

VIa

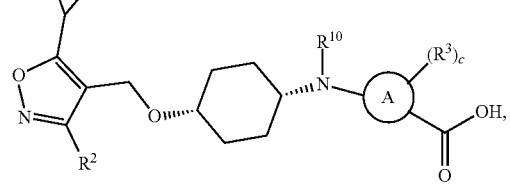

VIb wherein R²,

c, R³, and R¹⁰ are as defined in claim 1.

8. The compound of claim 7, selected from compounds according to Formula (VIa) or Formula (VIb), or a pharmaceutically acceptable salt thereof, wherein R², R¹⁰, and are delineated for each compound in Table 1:

TABLE 1

TABLE 1-continued

| Entry | R² | R¹⁰ | A ring-COOH |
|---|---|---|---|
| 17 | 2-F₃CO-phenyl | H | 5-pyrazinyl-2-COOH |
| 18 | 2-F₃CO-phenyl | H | 5-F-pyridin-2-yl-COOH |
| 19a | 2-F₃CO-phenyl | Me | quinolin-2-yl-5-COOH |
| 20a | 2-F₃CO-phenyl | Me | quinolin-2-yl-6-COOH |
| 21a | 2-F₃CO-phenyl | Me | quinoxalin-2-yl-5-COOH |
| 22a | 2-F₃CO-phenyl | Me | quinoxalin-2-yl-6-COOH |
| 23a | 2-F₃CO-phenyl | Me | pyrazin-2-yl-5-COOH |
| 24a | 2-F₃CO-phenyl | Me | 5-F-pyridin-2-yl-COOH |
| 25a | 2,6-diF-phenyl | H | quinolin-2-yl-5-COOH |
| 26a | 2,6-diF-phenyl | H | quinolin-2-yl-6-COOH |
| 27a | 2,6-diF-phenyl | H | quinoxalin-2-yl-5-COOH |
| 28a | 2,6-diF-phenyl | H | quinoxalin-2-yl-6-COOH |
| 29a | 2,6-diF-phenyl | H | pyrazin-2-yl-5-COOH |
| 30a | 2,6-diF-phenyl | H | 5-F-pyridin-2-yl-COOH |
| 31a | 2,6-diF-phenyl | Me | quinolin-2-yl-6-COOH |
| 32a | 2,6-diF-phenyl | Me | quinolin-2-yl-6-COOH |
| 33a | 2,6-diF-phenyl | Me | quinoxalin-2-yl-5-COOH |
| 34a | 2,6-diF-phenyl | Me | quinoxalin-2-yl-6-COOH |

TABLE 1-continued

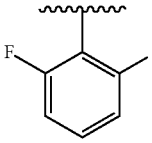

| Entry | R² | R¹⁰ | |
|---|---|---|---|
| 35a | 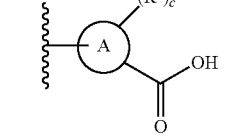 | Me | 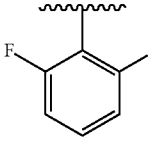 |
| 36a | 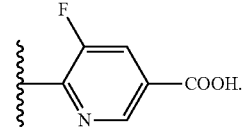 [SMILES: *c1ncc(C(=O)O)cc1F] | Me | 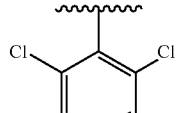 |

9. The compound of claim 1, represented by Formula (VIIa-b) or Formula (VIIb-b), or a pharmaceutically acceptable salt thereof, VIIa-b

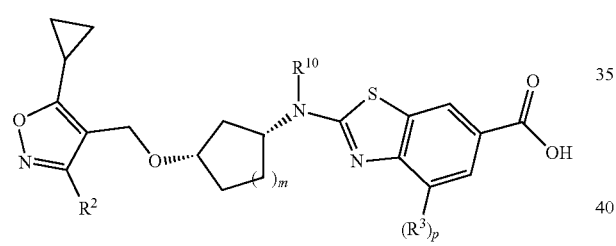

VIIb-b

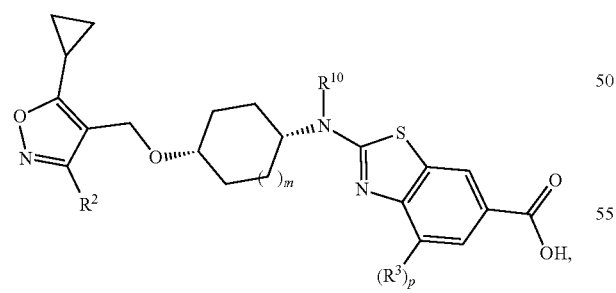

wherein p is 0 or 1; and R², m, R³, and R¹⁰ are as defined in claim 1.

10. The compound of claim 9, selected from compounds according to Formula (VIIa-b) or Formula (VIIb-b), or a pharmaceutically acceptable salt thereof, wherein p is 1, and R², m, R¹⁰ and R³ are delineated for each compound in Table 2:

TABLE 2

| Entry | R² | m | R¹⁰ | R³ |
|---|---|---|---|---|
| 1b | 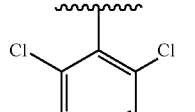 | 0 | H | F |
| 2b | 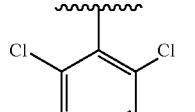 | 0 | H | Oi-Pr |
| 3b | 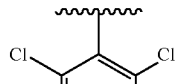 | 0 | Me | F |
| 4b | 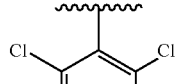 | 0 | Me | Oi-Pr |
| 5b |  | 0 | 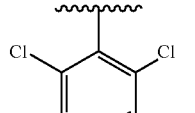 | F |
| 6b |  | 0 | 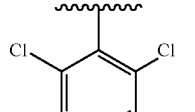 | Oi-Pr |
| 7b | 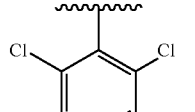 | 1 | H | F |
| 8b | 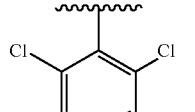 | 1 | H | Oi-Pr |
| 9b | 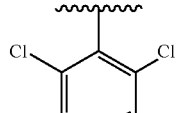 | 1 | Me | F |
| 10b | | 1 | Me | Oi-Pr |

TABLE 2-continued

| Entry | R² | m | R¹⁰ | R³ |
|---|---|---|---|---|
| 11b | 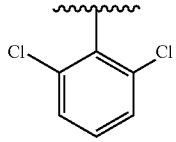 [SMILES: *c1c(Cl)cccc1Cl] 2,6-diCl-phenyl | 1 |  cyclopropyl | F |
| 12b | 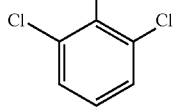 2,6-diCl-phenyl | 1 |  cyclopropyl | Oi-Pr |
| 13b | 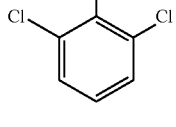 2,6-diCl-phenyl | 2 | H | F |
| 14b | 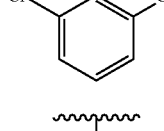 2,6-diCl-phenyl | 2 | H | Oi-Pr |
| 15b | 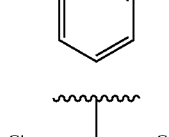 2,6-diCl-phenyl | 2 | Me | F |
| 16b | 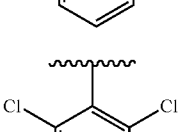 2,6-diCl-phenyl | 2 | Me | Oi-Pr |
| 17b | 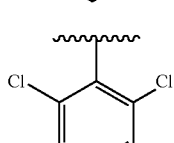 2,6-diCl-phenyl | 2 |  cyclopropyl | F |
| 18b | 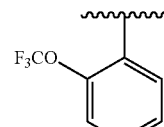 2,6-diCl-phenyl | 2 |  cyclopropyl | Oi-Pr |
| 19b | 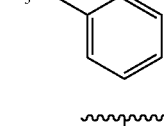 2-OCF₃-phenyl | 0 | H | F |
| 20b | 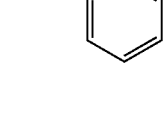 2-OCF₃-phenyl | 0 | H | Oi-Pr |
| 21b | 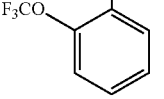 2-OCF₃-phenyl | 0 | Me | F |
| 22b | 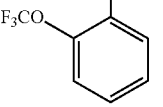 2-OCF₃-phenyl | 0 | Me | Oi-Pr |
| 23b | 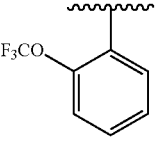 [SMILES: *c1ccccc1OC(F)(F)F] 2-OCF₃-phenyl | 0 |  cyclopropyl | F |
| 24b | 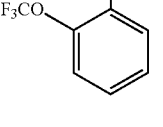 2-OCF₃-phenyl | 0 |  cyclopropyl | Oi-Pr |
| 25b | 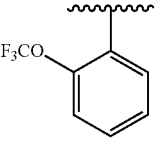 [SMILES: *c1ccccc1OC(F)(F)F] 2-OCF₃-phenyl | 1 | H | F |
| 26b | 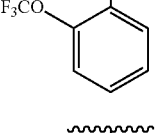 2-OCF₃-phenyl | 1 | H | Oi-Pr |
| 27b | 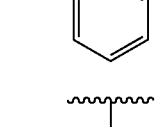 2-OCF₃-phenyl | 1 | Me | F |
| 28b | 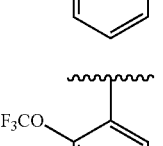 2-OCF₃-phenyl | 1 | Me | Oi-Pr |
| 29b | 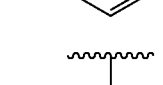 2-OCF₃-phenyl | 1 |  cyclopropyl | F |
| 30b | 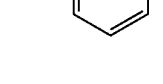 2-OCF₃-phenyl | 1 |  cyclopropyl | Oi-Pr |

TABLE 2-continued

| Entry | R² | m | R¹⁰ | R³ |
|---|---|---|---|---|
| 31b | 2-F₃CO-C₆H₄ | 2 | H | F |
| 32b | 2-F₃CO-C₆H₄ | 2 | H | Oi-Pr |
| 33b | 2-F₃CO-C₆H₄ | 2 | Me | F |
| 34b | 2-F₃CO-C₆H₄ | 2 | Me | Oi-Pr |
| 35b | 2-F₃CO-C₆H₄ | 2 | cyclopropyl | F |
| 36b | 2-F₃CO-C₆H₄ | 2 | cyclopropyl | Oi-Pr |
| 37b | 2,6-F₂-C₆H₃ | 0 | H | F |
| 38b | 2,6-F₂-C₆H₃ | 0 | H | Oi-Pr |
| 39b | 2,6-F₂-C₆H₃ | 0 | Me | F |
| 40b | 2,6-F₂-C₆H₃ | 0 | Me | Oi-Pr |
| 41b | 2,6-F₂-C₆H₃ | 0 | cyclopropyl | F |
| 42b | 2,6-F₂-C₆H₃ | 0 | cyclopropyl | Oi-Pr |
| 43b | 2,6-F₂-C₆H₃ | 1 | H | F |
| 44b | 2,6-F₂-C₆H₃ | 1 | H | Oi-Pr |
| 45b | 2,6-F₂-C₆H₃ | 1 | Me | F |
| 46b | 2,6-F₂-C₆H₃ | 1 | Me | Oi-Pr |
| 47b | 2,6-F₂-C₆H₃ | 1 | cyclopropyl | F |
| 48b | 2,6-F₂-C₆H₃ | 1 | cyclopropyl | Oi-Pr |
| 49b | 2,6-F₂-C₆H₃ | 2 | H | F |
| 50b | 2,6-F₂-C₆H₃ | 2 | H | Oi-Pr |

TABLE 2-continued

| Entry | R² | m | R¹⁰ | R³ |
|---|---|---|---|---|
| 51b | 2,6-difluorophenyl | 2 | Me | F |
| 52b | 2,6-difluorophenyl | 2 | Me | Oi-Pr |
| 53b | 2,6-difluorophenyl | 2 | (cyclopropyl) | F |
| 54b | | 2 | | Oi-Pr. |

11. The compound of claim 1, represented by Formula (VIIIa), Formula (VIIIb), Formula (VIIIc), or Formula (VIIId), or a pharmaceutically acceptable salt thereof,

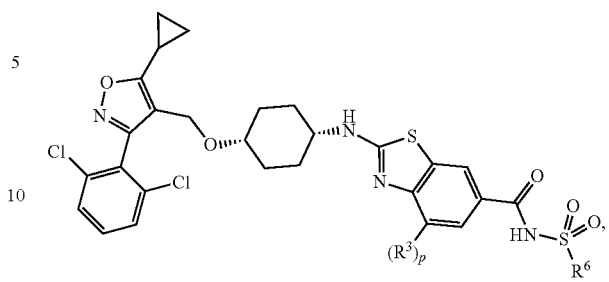

wherein p is 0 or 1; and R³ and R⁶ are as defined in claim 1.

12. The compound of claim 11, selected from compounds according to Formula (VIIIa), Formula (VIIIb), Formula (VIIIc), or Formula (VIIId), or a pharmaceutically acceptable salt thereof, wherein p is 1 and R³ and R⁶ are delineated for each compound in Table 3

TABLE 3

| Entry | R³ | R⁶ |
|---|---|---|
| 1c | Oi-Pr | Methyl |
| 2c | Oi-Pr | Ethyl |
| 3c | Oi-Pr | Isopropyl |
| 4c | Oi-Pr | Butyl |
| 5c | Oi-Pr | t-Butyl |
| 6c | Oi-Pr | Propyl |
| 7c | Oi-Pr | Benzyl |
| 8c | Oi-Pr | Vinyl |
| 9c | Oi-Pr | Allyl |
| 10c | Oi-Pr | —CF₃ |
| 11c | Oi-Pr |  |
| 12c | Oi-Pr |  |
| 13c | Oi-Pr |  |
| 14c | Oi-Pr | 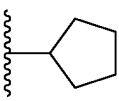 |
| 15c | Oi-Pr | 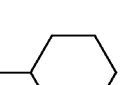 |
| 16c | Oi-Pr | 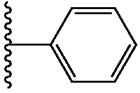 |
| 17c | Oi-Pr | 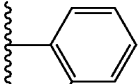 |

TABLE 3-continued

| Entry | R³ | R⁶ |
|---|---|---|
| 18c | Oi-Pr | 4-methylphenyl |
| 19c | Oi-Pr | 4-(OCF₃)phenyl |
| 20c | Oi-Pr | 4-tert-butylphenyl |
| 21c | Oi-Pr | 2-(OCF₃)phenyl |
| 22c | Oi-Pr | 2-fluorophenyl |
| 23c | Oi-Pr | 2-naphthyl |
| 24c | Oi-Pr | —NH₂ |
| 25c | Oi-Pr | —NHCH₃ |
| 26c | Oi-Pr | —N(CH₃)₂ |
| 27c | Oi-Pr | pyrrolidin-1-yl |
| 28c | Oi-Pr | piperidin-1-yl |
| 29c | Oi-Pr | morpholin-4-yl |
| 30c | F | Methyl |
| 31c | F | Ethyl |
| 32c | F | Isopropyl |
| 33c | F | Butyl |
| 34c | F | t-Butyl |
| 35c | F | Propyl |
| 36c | F | Benzyl |
| 37c | F | Vinyl |
| 38c | F | Allyl |
| 39c | F | —CF₃ |
| 40c | F | cyclopropyl |
| 41c | F | 1-methylcyclopropyl |
| 42c | F | cyclopropylmethyl |
| 43c | F | cyclopentyl |
| 44c | F | cyclohexyl |
| 45c | F | phenyl |
| 46c | F | 2-methylphenyl |
| 47c | F | 4-methylphenyl |
| 48c | F | 4-(OCF₃)phenyl |
| 49c | F | 4-tert-butylphenyl |
| 50c | F | 2-(OCF₃)phenyl |
| 51c | F | 2-fluorophenyl |
| 52c | F | 2-naphthyl |
| 53c | F | —NH₂ |
| 54c | F | —NHCH₃ |
| 55c | F | —N(CH₃)₂ |

TABLE 3-continued

| Entry | R³ | R⁶ |
|---|---|---|
| 56c | F | 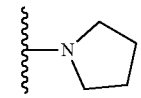 pyrrolidine |
| 57c | F | 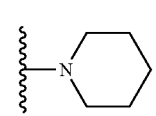 piperidine |
| 58c | F | 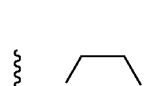 morpholine |

13. The compound of claim 1, represented by Formula (IXa-b), (IXb-b), (IXc-b) or (IXd-b), or a pharmaceutically acceptable salt thereof, IXa-b

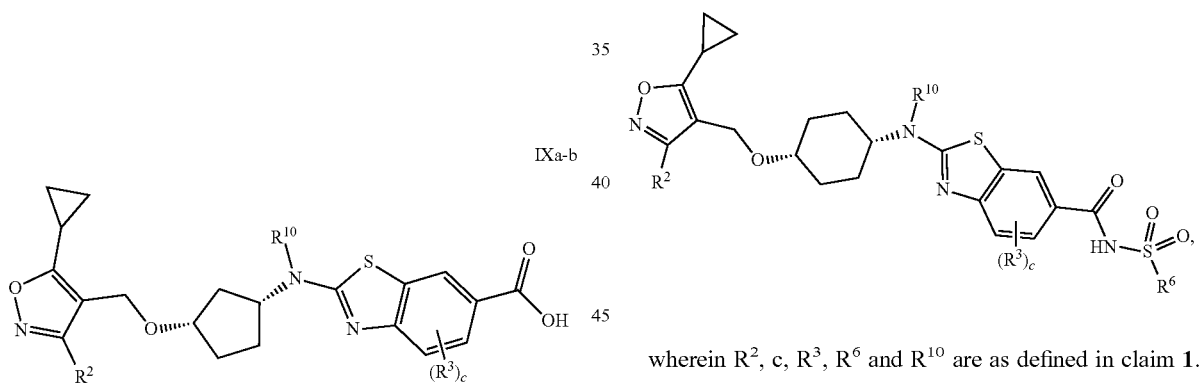

IXb-b

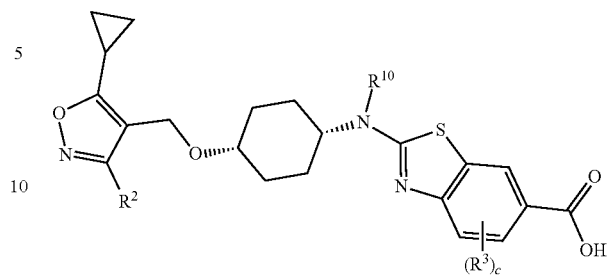

IXc-b

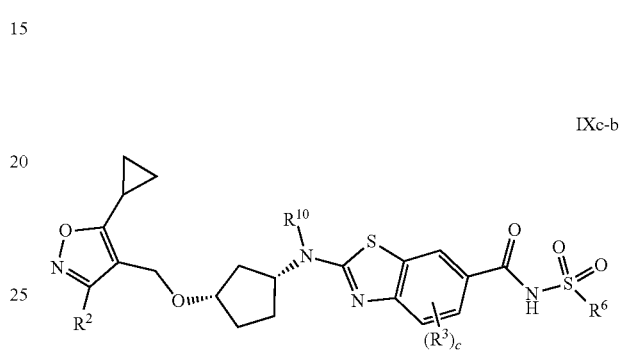

IXd-b

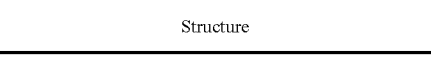

wherein $R^2$, c, $R^3$, $R^6$ and $R^{10}$ are as defined in claim 1.

14. A compound, selected from the compounds set forth below or a pharmaceutically acceptable salt thereof:

| Compound | Structure | Compound | Structure |
|---|---|---|---|
| 1 | 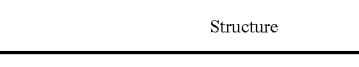 | 2 | 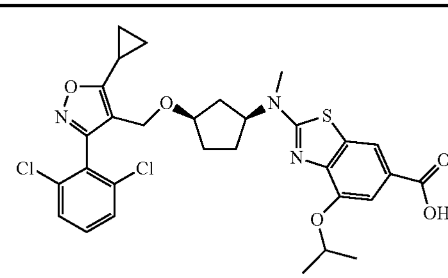 |

-continued

| Compound | Structure | Compound | Structure |
|---|---|---|---|
| 3 | 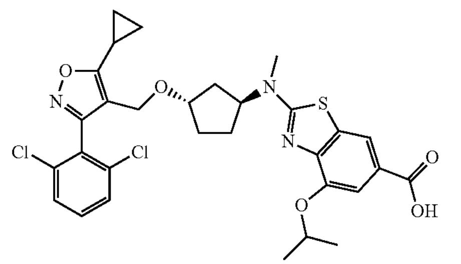 [SMILES: CC(C)Oc1cc(C(=O)O)cc2sc(N(C)[C@H]3CC[C@H](OCc4c(-c5c(Cl)cccc5Cl)noc4C4CC4)C3)nc12] | 4 | 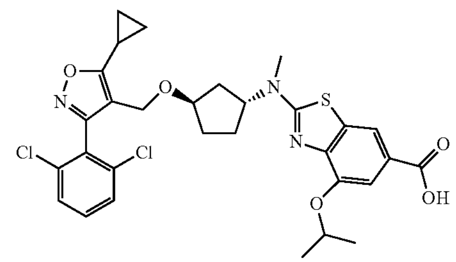 [SMILES: CC(C)Oc1cc(C(=O)O)cc2sc(N(C)[C@@H]3CC[C@@H](OCc4c(-c5c(Cl)cccc5Cl)noc4C4CC4)C3)nc12] |
| 5 | 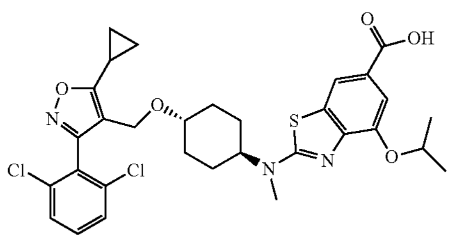 [SMILES: CC(C)Oc1cc(C(=O)O)cc2sc(N(C)[C@H]3CC[C@H](OCc4c(-c5c(Cl)cccc5Cl)noc4C4CC4)CC3)nc12] | 6 | 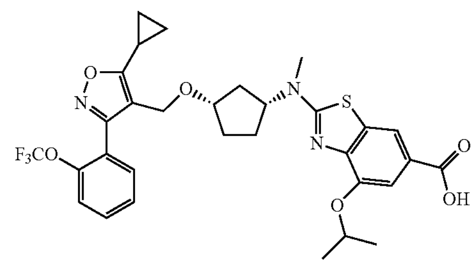 [SMILES: CC(C)Oc1cc(C(=O)O)cc2sc(N(C)[C@@H]3CC[C@H](OCc4c(-c5ccccc5OC(F)(F)F)noc4C4CC4)C3)nc12] |
| 7 | 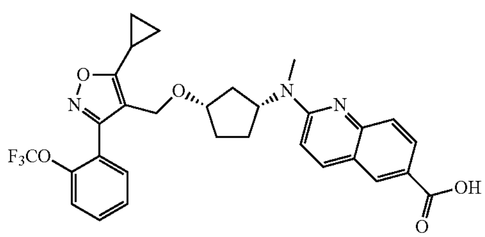 [SMILES: CN(c1ccc2cc(C(=O)O)ccc2n1)[C@@H]1CC[C@H](OCc2c(-c3ccccc3OC(F)(F)F)noc2C2CC2)C1] | 8 | 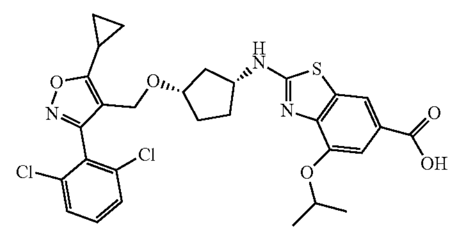 [SMILES: CC(C)Oc1cc(C(=O)O)cc2sc(N[C@@H]3CC[C@H](OCc4c(-c5c(Cl)cccc5Cl)noc4C4CC4)C3)nc12] |
| 9 | 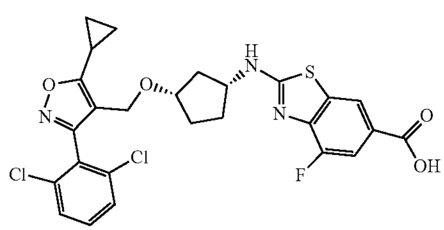 [SMILES: O=C(O)c1cc(F)c2nc(N[C@@H]3CC[C@H](OCc4c(-c5c(Cl)cccc5Cl)noc4C4CC4)C3)sc2c1] | 10 | 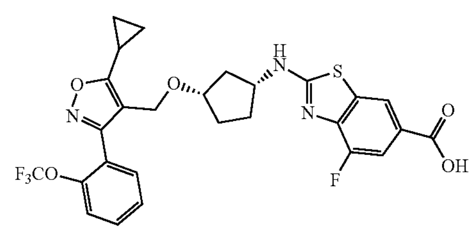 [SMILES: O=C(O)c1cc(F)c2nc(N[C@@H]3CC[C@H](OCc4c(-c5ccccc5OC(F)(F)F)noc4C4CC4)C3)sc2c1] |
| 11 | 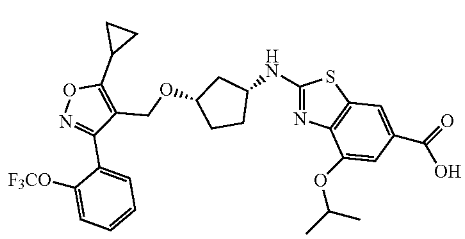 [SMILES: CC(C)Oc1cc(C(=O)O)cc2sc(N[C@@H]3CC[C@H](OCc4c(-c5ccccc5OC(F)(F)F)noc4C4CC4)C3)nc12] | 12 | 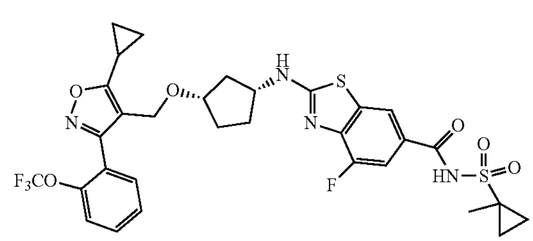 [SMILES: CC1(S(=O)(=O)NC(=O)c2cc(F)c3nc(N[C@@H]4CC[C@H](OCc5c(-c6ccccc6OC(F)(F)F)noc5C5CC5)C4)sc3c2)CC1] |
| 13 | 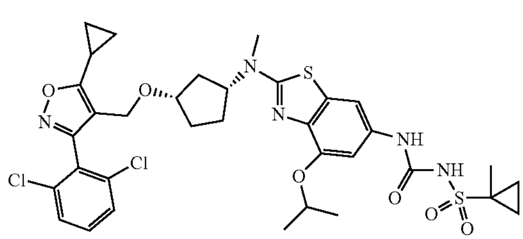 [SMILES: CC(C)Oc1cc(NC(=O)NS(=O)(=O)C2(C)CC2)cc2sc(N(C)[C@@H]3CC[C@H](OCc4c(-c5c(Cl)cccc5Cl)noc4C4CC4)C3)nc12] | 14 | 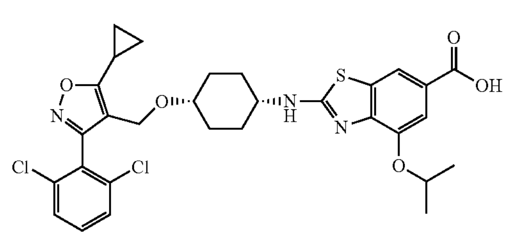 [SMILES: CC(C)Oc1cc(C(=O)O)cc2sc(N[C@H]3CC[C@@H](OCc4c(-c5c(Cl)cccc5Cl)noc4C4CC4)CC3)nc12] |

| Compound | Structure |
|---|---|
| | ![structure with cyclopropyl-isoxazole-dichlorophenyl-cyclohexyl-N(Me)-benzothiazole-COOH and isopropoxy] OH. |

15. A method for treating an FXR-mediated disease or condition selected from the group consisting of primary biliary cirrhosis, cerebrotendinous xanthomatosis, primary sclerosing cholangitis, alcoholic liver disease, nonalcoholic fatty liver disease, nonalcoholic steatohepatitis, atherosclerosis, hypercholesterolemia, hypertriglyceridemia, and Type II diabetes in a subject in need thereof, comprising administering to the subject a therapeutically effective amount of a compound according to claim 1.

16. The method according to claim 15, wherein the FXR-mediated disease or condition is selected from the group consisting of primary biliary cirrhosis, primary sclerosing cholangitis, and cerebrotendinous xanthomatosis.

17. A pharmaceutical composition comprising a compound of claim 1, and a pharmaceutically acceptable excipient or carrier.

18. A method for treating nonalcoholic steatohepatitis in a subject in need thereof, comprising administering to the subject a therapeutically effective amount of a compound according to claim 1.

19. A method for treating primary biliary cirrhosis in a subject in need thereof, comprising administering to the subject a therapeutically effective amount of a compound according to claim 1.

20. A method for treating nonalcoholic fatty liver disease in a subject in need thereof, comprising administering to the subject a therapeutically effective amount of a compound according to claim 1.

21. The compound according to claim 1 selected from compounds 16-20 set forth below, or a pharmaceutically acceptable salt thereof:

| Compound | Structure |
|---|---|
| 16 | 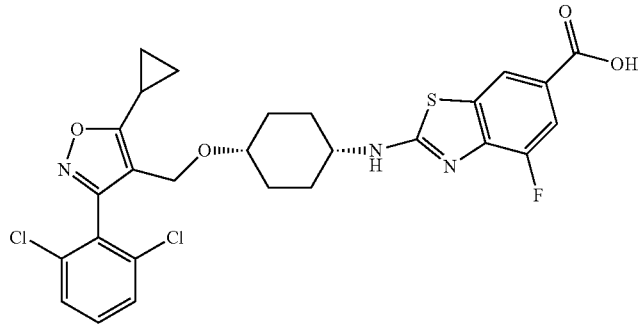 [SMILES: O=C(O)c1cc(F)c2nc(N[C@H]3CC[C@@H](OCc4c(-c5c(Cl)cccc5Cl)noc4C4CC4)CC3)sc2c1] |
| 17 | 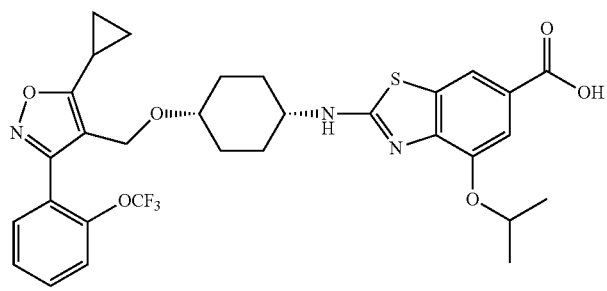 [SMILES: CC(C)Oc1cc(C(=O)O)cc2sc(N[C@H]3CC[C@@H](OCc4c(-c5ccccc5OC(F)(F)F)noc4C4CC4)CC3)nc12] |

-continued

| Compound | Structure |
|---|---|
| 18 | (structure: 5-cyclopropyl-3-(2,6-dichlorophenyl)isoxazol-4-yl)methoxy-cyclohexyl-NH-benzothiazole-6-carboxylic acid) |
| 19 | (structure: 5-cyclopropyl-3-(2,6-dichlorophenyl)isoxazol-4-yl)methoxy-cyclopentyl-NH-benzothiazole-6-COOH) |
| 20 | (structure: 5-cyclopropyl-3-(2,6-dichlorophenyl)isoxazol-4-yl)methoxy-cyclopentyl-NH-benzothiazole with isopropoxy and cyclopropanesulfonamide carboxamide) |

\* \* \* \* \*

UNITED STATES PATENT AND TRADEMARK OFFICE
CERTIFICATE OF CORRECTION

PATENT NO. : 10,829,486 B2
APPLICATION NO. : 16/272506
DATED : November 10, 2020
INVENTOR(S) : Ruichao Shen et al.

Page 1 of 1

It is certified that error appears in the above-identified patent and that said Letters Patent is hereby corrected as shown below:

In the Claims

At Column 89

In Claim 10, at Line 26 after 54b insert -- 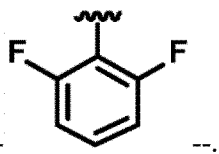 --.

Signed and Sealed this
Second Day of February, 2021

Drew Hirshfeld
*Performing the Functions and Duties of the
Under Secretary of Commerce for Intellectual Property and
Director of the United States Patent and Trademark Office*